(12) United States Patent
Jia

(10) Patent No.: US 7,674,830 B2
(45) Date of Patent: *Mar. 9, 2010

(54) FORMULATION OF A MIXTURE OF FREE-B-RING FLAVONOIDS AND FLAVANS AS A THERAPEUTIC AGENT

(75) Inventor: Qi Jia, Superior, CO (US)

(73) Assignee: Unigen Pharmaceuticals, Inc., Lacey, WA (US)

( * ) Notice: Subject to any disclaimer, the term of this patent is extended or adjusted under 35 U.S.C. 154(b) by 703 days.

This patent is subject to a terminal disclaimer.

(21) Appl. No.: 10/462,030

(22) Filed: Jun. 13, 2003

(65) Prior Publication Data

US 2003/0232763 A1    Dec. 18, 2003

Related U.S. Application Data

(63) Continuation of application No. 10/427,746, filed on Apr. 30, 2003.

(60) Provisional application No. 60/377,168, filed on Apr. 30, 2002.

(51) Int. Cl.
  *A01N 31/08* (2006.01)
  *A61K 31/05* (2006.01)

(52) U.S. Cl. .................................................. 514/732

(58) Field of Classification Search ................ 514/732
  See application file for complete search history.

(56) References Cited

U.S. PATENT DOCUMENTS

| | | | |
|---|---|---|---|
| 3,686,872 A | 8/1972 | Whitworth et al. | |
| 3,706,581 A | 12/1972 | Whitworth et al. | |
| 4,374,824 A | 2/1983 | Wahmi | |
| 4,946,684 A | 8/1990 | Blank et al. | |
| 5,443,983 A | 8/1995 | Ochoa et al. | |
| 5,470,589 A | 11/1995 | Shi | |
| 5,545,411 A | 8/1996 | Chancellor | |
| 5,605,929 A | 2/1997 | Liao et al. | |
| 5,643,598 A | 7/1997 | Maybeck | |
| 5,650,432 A | 7/1997 | Walker | |
| 5,651,987 A | 7/1997 | Fuisz | |
| 5,756,538 A | 5/1998 | Cassels et al. | |
| 5,795,911 A | 8/1998 | Cheng et al. | |
| 5,858,371 A | 1/1999 | Singh et al. | |
| 5,886,029 A | 3/1999 | Dhaliwal | |
| 5,922,756 A | 7/1999 | Chan | |
| 5,962,517 A | 10/1999 | Murad | |
| 5,968,973 A | 10/1999 | Cheng et al. | |
| 6,080,401 A | 6/2000 | Reddy et al. | |
| 6,083,921 A | 7/2000 | Xu | |
| 6,093,403 A | 7/2000 | Huo et al. | |
| 6,126,940 A | 10/2000 | Takahashi et al. | |
| 6,126,950 A | 10/2000 | Bindra et al. | |
| 6,197,808 B1 | 3/2001 | Cheng et al. | |
| 6,217,875 B1 | 4/2001 | Murai et al. | |
| 6,235,294 B1 | 5/2001 | Perrier et al. | |
| 6,248,341 B1 | 6/2001 | Anderson et al. | |
| 6,264,995 B1 | 7/2001 | Newmark et al. | |
| 6,290,995 B1 | 9/2001 | Xinxian | |
| 6,387,416 B1 | 5/2002 | Newmark et al. | |
| 6,391,346 B1 | 5/2002 | Newmark et al. | |
| 6,475,530 B1 | 11/2002 | Kuhrts | |
| 2003/0105030 A1* | 6/2003 | Liao et al. | ............ 514/27 |
| 2004/0186062 A1 | 9/2004 | Burnett et al. | |

FOREIGN PATENT DOCUMENTS

| | | |
|---|---|---|
| CN | 1096680 | 12/1994 |
| CN | 1189365 A | 8/1998 |
| CN | 1285202 | 2/2001 |
| EP | 09568674 A1 | 11/1999 |
| FR | 2651132 | 3/1991 |
| JP | 403240725 | 10/1991 |
| JP | 07233941 | 8/1995 |
| JP | 2002053484 | 2/2002 |
| WO | WO 98/40086 | 9/1998 |
| WO | WO 00/59523 | 10/2000 |

OTHER PUBLICATIONS

Kim et al. (1990) Yakhak Hoeji 34(5):348-364.
Afolayan and Meyer (1997) Journal of Ethnopharmacol. 57(3):177-181.
Agarwal et al. (1993) Photochem. Photobiol. 58:695-700.
Amos et al. (1999) Phytotherapy Research 13:683-685 (Abstract only).
Bastianetto et al. (2000) Br. J. Pharmacol. 131:711-720.
Boumendjel et al. (2001) Bioorg. Med. Chem. Lett. 11(1):75-77.
Chen et al. (2001) Biochem. Pharmacol. 61(11):1417-1427.
Chi et al. (2001) Biochem. Pharmacol. 61:1195-1203.
Commenges et al. (Apr. 2000) Eur. J. Epidemiol 16:357-363 (Abstract).

(Continued)

*Primary Examiner*—Yong S Chong
(74) *Attorney, Agent, or Firm*—Swanson & Bratschun, L.L.C.

(57) ABSTRACT

The present invention provides a novel composition of matter comprised of a mixture of two specific classes of compounds—Free-B-ring flavonoids and flavans—for use in the prevention and treatment of diseases and conditions mediated by the COX-2 and 5-LO pathways. The present invention further provides a novel method for simultaneously inhibiting the cyclooxygenase-2 (COX-2) and 5-lipoxygenase (5-LO) enzymes, and reducing cox-2 mRNA production. Finally, the present invention includes a method for weight loss and blood glucose control. The methods of this invention are comprised of administering to a host in need thereof an effective amount of the composition of this invention together with a pharmaceutically acceptable carrier. This invention relates generally to the prevention and treatment of diseases and conditions mediated by the cyclooxygenase-2 (COX-2) and 5-lipoxygenase (5-LO) pathways, including but not limited to the relief joint discomfort and pain associated with conditions such as osteoarthritis, rheumatoid arthritis, and other injuries that result from overuse.

2 Claims, 20 Drawing Sheets

OTHER PUBLICATIONS

Dafallah and Al-Mustafa (1996) American Journal of Chinese Medicine. 24:263-269 (Abstract only).
Gilani et al. (Dec. 1999) Phytotherapy Research. 13:665-669 (Abstract only).
Hagos et al. (Feb. 1987) Planta Medica. 53:27-31, 1987 (Abstract only).
Hanausek-Walaszek et al. (Mar. 2000) Proceedings American Association for Cancer Research Annual Meeting 41:663 (abstract #4216).
Haridas et al. (Mar. 2000) Proceedings American Association for Cancer Research Annual Meeting. 41:600 (abstract #3820).
Heo et al. (2001) Mutat. Res. 488(2):135-150.
Hong et al. (2001) Biochem. Pharmacol. 62:1175-1183.
Imamura et al. (2000) J. Biochem. 127(4):653-658.
Itoigawa et al. (1999) J. Ethnopharmacol. 65(3): 267-272.
Kalkbrenner et al. (1992) Pharmacology 44(1):1-12.
Kaneko and Baba (1999) Biosci Biotechnol. Biochem 63(2):323-328.
Kimura et al. (2001) Planta Med. 67:331-334.
Krakauer et al. (2001) FEBS Lett. 500:52-55.
Kubo et al. (2000) Bioorg. Med. Chem. 8(7):1749-1755.
Li et al. (2000) Immunopharmacology 49:295-306.
Liang et al. (2001) FEBS Lett. 496(1):12-18.
Meyer et al. (1997) J. Ethnopharmacol. 56(2):165-169.
Min et al. (1999) Planta Med. 65:460-462.
Mutoh et al. (Jul. 2000) Jnp. J. Cancer Res. 91:686-691 (abstract).
Nadkarni (1996) India Materia Medica, Bombay Popular Prakashan, pp. 9-17.
Nakahata et al. (1998) Am. J. Chin Med. 26:311-323 (abstract).
Nakahata et al. (1999) Nippon Yakurigaku Zasshi,114, Supp. 11:215P-219P.
Nakajima et al. (2001) Planta Med. 67(2):132-135.
Noreen et al. (1998) Planta Med. 64:520-524.
Noreen et al. (Jan. 1998) J. Nat. Prod. 61:2-7.
Noreen et al. (Jan. 1998) J. Nat. Prod. 61:8-12.
Park et al. (2001) Biochem. Biophys. Res. Commun. 286:721-725.
Raso et al. (2001) Life Sci. 68(8):921-931.
Sekine et al. (1997) Chemical and Pharmaceutical Bulletin. 45:148-11.
Shah et al. (1997) General Pharmacology. 29:251-255.
So et al. (1997) Cancer Lett. 112(2):127-133.
Tordera et al. (Mar.-Apr. 1994) Z. Naturforsch [C] 49:235-240 (abstract).
Wakabayashi and Yasui (2000) Eur. J. Pharmacol. 406(3):477-481.
Wang (Mar. 2000) Phytomedicine 7:15-19 (abstract).
Wenzel et al. (Jul. 2000) Cancer Res. 60:3823-3831.
You et al. (Feb. 1999) Arch. Pharm. Res. 22(1):18-24 (abstract).
Nakagami (Aug. 22, 1995) abstract Database WPI Week 199519 Aug. 22, 1995, Derwent Publications Ltd., London, GB; p. 2, AN 1995-325471 XP002418722 Nakagami T; Nakamura T; Tamura N: "Anti-complementary substance used as therapeutic agent—comprises gallic acid, methyl gallate, acetyl-salicylic acid, caffeic acid, catechin, epi-gallo-catechin gallate, myricetin, quercitrin and/or baicalein, or their salts" & JP 07 223941 A ((NIHA-N) NIPPON HAM KK).
Hase et al. (Mar. 19, 2002) abstract, Database WPI Week 200242, Derwent Publications Ltd., London, GB: AN 2002-388616 XP002422560 & JP 2002 080362 A (Kao Corp) "Natural products derived PPAR dependent gene activators".
Hiipakka, et al., (2002) Structure-activity relationships for inhibition of human 5α-reductases by polyphenols, Biochemical Pharmacology 63:1165-1176.
Liao and Hiipakka., (1995) Selective Inhibition of Steroid 5α-Reductase Isozymes by Tea Epicatechin-3-Gallate and Epigallocatechin-3-Gallate, Biochemial and Biophysical Research Communications, 214(3):833-838.

* cited by examiner

FORMULATION OF A MIXTURE OF FREE-B-RING FLAVONOIDS AND FLAVANS AS A THERAPEUTIC AGENT

RELATED APPLICATIONS

This application is a continuation of U.S. patent application Ser. No. 10/427,746, filed Apr. 30, 2003, entitled Formulation Of A Mixture Of Free-B-Ring Flavonoids And Flavans As A Therapeutic Agent, which application claims priority to U.S. Provisional Application Ser. No. 60/377,168, filed Apr. 30, 2002, entitled Formulation With Dual COX-2 And 5-Lipoxygenase Inhibitory Activity. Each of these references is hereby incorporated by reference in its entirety.

FIELD OF THE INVENTION

This invention relates generally to the prevention and treatment of diseases and conditions mediated by the cyclooxygenase-2 (COX-2) and 5-lipoxygenase (5-LO) pathways. Specifically, the present invention relates to a novel composition of matter comprised of a mixture of a blend of two specific classes of compounds—Free-B-ring flavonoids and flavans—for use in the prevention and treatment of diseases and conditions mediated by the COX-2 and 5-LO pathways. Included in the present invention is a method for the simultaneous inhibition of the protein function of the COX-2 and 5-LO enzymes, and a method for modulating the production of mRNA by administration of the novel composition of this invention. Also included in the present invention is a method for the prevention and treatment of COX-2 and 5-LO mediated diseases and conditions, including but not limited to joint discomfort and pain associated with conditions such as osteoarthritis, rheumatoid arthritis, and other injuries that result from overuse. Further included in the present invention is a method for reducing blood glucose levels and promoting weight loss.

BACKGROUND OF THE INVENTION

The liberation and metabolism of arachidonic acid (AA) from the cell membrane results in the generation of pro-inflammatory metabolites by several different pathways. Arguably, two of the most important pathways to inflammation are mediated by the enzymes 5-lipoxygenase (5-LO) and cyclooxygenase (COX). These parallel pathways result in the generation of leukotrienes and prostaglandins, respectively, which play important roles in the initiation and progression of the inflammatory response. These vasoactive compounds are chemotaxins, which promote infiltration of inflammatory cells into tissues and serve to prolong the inflammatory response. Consequently, the enzymes responsible for generating these mediators of inflammation have become the targets for many new drugs aimed at the treatment of inflammation that contributes to the pathogenesis of diseases such as rheumatoid arthritis, osteoarthritis, Alzheimer's disease and certain types of cancer.

Inhibition of the cyclooxygenase (COX) enzyme is the mechanism of action attributed to most nonsteroidal anti-inflammatory drugs (NSAIDS). There are two distinct isoforms of the COX enzyme (COX-1 and COX-2) that share approximately 60% sequence homology, but differ in expression profiles and function. COX-1 is a constitutive form of the enzyme that has been linked to the production of physiologically important prostaglandins involved in the regulation of normal physiological functions such as platelet aggregation, protection of cell function in the stomach and maintenance of normal kidney function (Dannhardt and Kiefer (2001) Eur. J. Med. Chem. 36:109-26). The second isoform, COX-2, is a form of the enzyme that is inducible by pro-inflammatory cytokines such as interleukin-1β (IL-1β) and other growth factors (Herschmann (1994) Cancer Metastasis Rev. 134: 241-56; Xie et al. (1992) Drugs Dev. Res. 25:249-65). This isoform catalyzes the production of prostaglandin $E_2$ ($PGE_2$) from AA. Inhibition of COX-2 is responsible for the anti-inflammatory activities of conventional NSAIDs.

Inhibitors that demonstrate dual specificity for COX-2 and 5-LO, while maintaining COX-2 selectivity relative to COX-1, would have the obvious benefit of inhibiting multiple pathways of AA metabolism. Such inhibitors would block the inflammatory effects of $PGE_2$, as well as, those of multiple leukotrienes (LT) by limiting their production. This includes the vasodilation, vasopermeability and chemotactic effects of $LTB_4$ and $LTD_4$ and the effects of $LTE_4$, also known as the slow reacting substance of anaphalaxis. Of these, $LTB_4$ has the most potent chemotactic and chemokinetic effects (Moore (1985) in *Prostanoids: Pharmacological, Physiological and Clinical Relevance*, Cambridge University Press, N.Y., pp. 229-30) and has been shown to be elevated in the gastrointestinal mucosa of patients with inflammatory bowel disease (Sharon and Stenson (1983) Gastroenterology 84:1306-13) and within the synovial fluid of patients with rheumatoid arthritis (Klicksein et al. (1980) J. Clin. Invest. 66:1166-70; Rae et al (1982) Lancet ii: 1122-4).

In addition to the above-mentioned benefits of dual COX-2/5-LO inhibitors, many dual inhibitors do not cause some of the side effects that are typical of NSAIDs or COX-2 inhibitors, including the gastrointestinal damage and discomfort caused by traditional NSAIDs. It has been suggested that NSAID-induced gastric inflammation is largely due to metabolites of 5-LO, particularly $LTB_4$, which attracts cells to the site of a gastric lesion thus causing further damage (Kircher et al (1997) Prostaglandins Leukot. Essent. Fatty Acids 56:417-23). Leukotrienes represent the primary AA metabolites within the gastric mucosa following prostanoid inhibition. It appears that these compounds contribute to a significant amount of the gastric epithelial injury resulting from the use of NSAIDs. (Celotti and Laufer (2001) Pharmacol. Res. 43:429-36). Dual inhibitors of COX-2 and 5-LO were also demonstrated to inhibit the coronary vasoconstriction in arthritic hearts in a rat model (Gok et al. (2000) Pharmacology 60:41-46). Taken together, these characteristics suggest that there may be distinct advantages to dual inhibitors of COX-2 and 5-LO over specific COX-2 inhibitors and non-specific NSAIDs with regard to both increased efficacy and reduced side effects.

Because the mechanism of action of COX inhibitors overlaps that of most conventional NSAIDs, COX inhibitors are used to treat many of the same symptoms, such as the pain and swelling associated with inflammation in transient conditions and chronic diseases in which inflammation plays a critical role. Transient conditions include the treatment of inflammation associated with minor abrasions, sunburn or contact dermatitis, as well as, the relief of pain associated with tension and migraine headaches and menstrual cramps. Chronic conditions include arthritic diseases such as rheumatoid arthritis and osteoarthritis. Although rheumatoid arthritis is largely an autoimmune disease and osteoarthritis is caused by the degradation of cartilage in joints, reducing the inflammation associated with each provides a significant increase in the quality of life for those suffering from these diseases (Wienberg (2001) Immunol. Res. 22:319-41; Wollhiem (2000) Curr. Opin. Rheum. 13:193-201). As inflammation is a component of rheumatic diseases in general, the use of COX inhibitors has been expanded to include diseases such as systemic lupus erythromatosus (SLE) (Goebel et al. (1999) Chem. Res. Tox. 12:488-500; Patrono et al. (1985) J. Clin. Invest. 76:1011-1018) and rheumatic skin conditions such as scleroderma. COX inhibitors are also used for the relief of inflammatory skin conditions that are not of rheumatic origin, such as psoriasis, in which reducing the inflammation resulting from the over production of prostaglandins could provide a direct benefit (Fogh et al. (1993) Acta Derm. Venereol (Oslo) 73:191-3).

In addition to their use as anti-inflammatory agents, another potential role for COX inhibitors is the treatment of cancer. Over-expression of COX-2 has been demonstrated in various human malignancies and inhibitors of COX-2 have been shown to be efficacious in the treatment of animals with skin, breast and bladder tumors. While the mechanism of action is not completely understood, the over-expression of COX-2 has been shown to inhibit apoptosis and increase the invasiveness of tumorgenic cell types (Dempke et al. (2001) J. Can. Res. Clin. Oncol. 127:411-17; Moore and Simmons (2000) Current Med. Chem. 7:1131-44). It is possible that enhanced production of prostaglandins, resulting from the over-expression of COX-2, promotes cellular proliferation and consequently increases angiogenesis. (Moore (1985) in *Prostanoids: Pharmacological, Physiological and Clinical Relevance*, Cambridge University Press, N.Y., pp. 229-30; Fenton et al. (2001) Am. J. Clin. Oncol. 24:453-57).

There have been a number of clinical studies evaluating COX-2 inhibitors for potential use in the prevention and treatment of different types of cancer. In 1999, 130,000 new cases of colorectal cancer were diagnosed in the United States. Aspirin, a non-specific NSAID, has been found to reduce the incidence of colorectal cancer by 40-50% (Giovannucci et al. (1995) N. Engl. J. Med. 333:609-614) and mortality by 50% (Smalley et al. (1999) Arch. Intern. Med. 159:161-166). In 1999, the FDA approved the COX-2 inhibitor celecoxib for use in FAP (Familial Ademonatous Polyposis) to reduce colorectal cancer mortality. It is believed that other cancers with evidence of COX-2 involvement may be successfully prevented and/or treated with COX-2 inhibitors including, but not limited to, esophageal cancer, head and neck cancer, breast cancer, bladder cancer, cervical cancer, prostate cancer, hepatocellular carcinoma and non-small cell lung cancer (Jaeckel et al. (2001) Arch. Otolarnygol. 127: 1253-59; Kirschenbaum et al. (2001) Urology 58:127-31; Dannhardt and Kiefer (2001) Eur. J. Med. Chem. 36:109-26). COX-2 inhibitors may also prove successful in preventing colon cancer in high-risk patients. There is also evidence that COX-2 inhibitors can prevent or even reverse several types of life-threatening cancers. To date, as many as fifty studies show that COX-2 inhibitors can prevent pre-malignant and malignant tumors in animals, and possibly prevent bladder, esophageal and skin cancers as well. COX-2 inhibition could prove to be one of the most important preventive medical accomplishments of the century.

Recent scientific progress has identified correlations between COX-2 expression, general inflammation and the pathogenesis of Alzheimer's Disease (AD) (Ho et al. (2001) Arch. Neurol. 58:487-92). In animal models, transgenic mice that over-express the COX-2 enzyme have neurons that are more susceptible to damage. The National Institute on Aging (NIA) is launching a clinical trial to determine whether NSAIDs can slow the progression of Alzheimer's disease. Naproxen (a non-selective NSAID) and rofecoxib (Vioxx, a COX-2 specific selective NSAID) will be evaluated. Previous evidence has indicated that inflammation contributes to Alzheimer's disease. According to the Alzheimer's Association and the NIA, about 4 million people suffer from AD in the United States and this is expected to increase to 14 million by mid-century.

The COX enzyme (also known as prostaglandin $H_2$ synthase) catalyzes two separate reactions. In the first reaction, AA is metabolized to form the unstable prostaglandin $G_2$ ($PGG_2$), a cyclooxygenase reaction. In the second reaction, $PGG_2$ is converted to the endoperoxide $PGH_2$, a peroxidase reaction. The short-lived $PGH_2$ non-enzymatically degrades to $PGE_2$. The compounds described herein are the result of a discovery strategy that combined an assay focused on the inhibition of COX-1 and COX-2 peroxidase activity with a chemical dereplication process to identify novel inhibitors of the COX enzymes.

The term gene expression is often used to describe the broad result of mRNA production and protein synthesis. In fact, changes in actual gene expression may never result in observable changes on the protein level. The corollary, that changes in protein level do not always result from changes in gene expression, can also be true. There are six possible points of regulation in the pathway leading from genomic DNA to a functional protein: (1) transcriptional regulation by nuclear factors and other signals leading to production of pre-mRNA; (2) pre-mRNA processing regulation involving exon splicing, the additions of a 5' cap structure and 3' polyadenylation sequence and transport of the mature mRNA from the nucleus into the cytoplasm; (3) mRNA transport regulation controlling localization of the mRNA to a specific cytoplasmic site for translation into protein; (4) mRNA degradation regulation controlling the size of the mRNA pool either prior to any protein translation or as a means of ending translation from that specific mRNA; (5) translational regulation of the specific rate of protein translation initiation and (6) post-translation processing regulation involving modifications such as glycosylation and proteolytic cleavage. In the context of genomics research it is important to use techniques that measure gene expression levels closer to the initial steps (e.g. mRNA levels) rather than later steps (e.g. protein levels) in this pathway.

Recent reports have addressed the possible involvement of flavonoids, isolated from the medicinal herb *Scutellaria baicalensis*, in alterations in cox-2 gene expression (Wakabayashi and Yasui (2000) Eur. J. Pharmacol. 406:477-481; Chen et al. (2001) Biochem. Pharmacol. 61:1417-1427; Chi et al. (2001) 61:1195-1203 and Raso et al. (2001) Life Sci. 68:921-931). Each of above cited studies on cox-2 gene expression used a Western Blot technique to evaluate putative alterations in gene expression without validation on the molecular level. Since this method only measures protein levels and not the specific transcription product, mRNA, it is possible that other mechanisms are involved leading to the observed increase in protein expression. For example, LPS has been reported to modulate mRNA half-lives via instability sequences found in the 3' untranslated region (3'UTR) of mRNAs (Watkins et al. (1999) Life Sci. 65:449-481), which could account for increased protein expression without alternations in the rate of gene transcription. Consequently, this leaves open the question of whether or not these treatment conditions resulted in a meaningful change in gene expression.

Techniques, such as RT-qPCR and DNA microarray analysis, rely on mRNA levels for analysis and can be used to evaluate levels of gene expression under different conditions, i.e. in the presence or absence of a pharmaceutical agent. There are no known reports using techniques that specifically measure the amount of mRNA, directly or indirectly, in the literature when Free-B-ring flavonoids or flavans are used as the therapeutic agents.

Flavonoids are a widely distributed group of natural products. The intake of flavonoids has been demonstrated to be inversely related to the risk of incident dementia. The mechanism of action, while not known, has been speculated as being due to the anti-oxidative effects of flavonoids (Commenges et al. (2000) Eur. J. Epidemiol. 16:357-363). Polyphenol flavones induce programmed cell death, differentiation and growth inhibition in transformed colonocytes by acting at the mRNA level on genes including cox-2, Nuclear Factor kappa B (NFκB) and bcl-X(L) (Wenzel et al. (2000) Cancer Res. 60:3823-3831). It has been reported that the number of hydroxyl groups on the B ring is important in the suppression of cox-2 transcriptional activity (Mutoh et al. (2000) Jnp. J. Cancer Res. 91:686-691).

Free-B-ring flavones and flavonols are a specific class of flavonoids, which have no substituent groups on the aromatic B ring (referred to herein as Free-B-ring flavonoids), as illustrated by the following general structure:

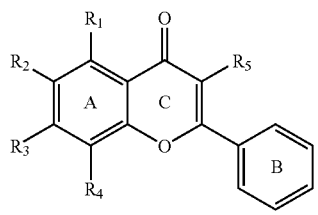

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

Free-B-ring flavonoids are relatively rare. Out of 9,396 flavonoids synthesized or isolated from natural sources, only 231 Free-B-ring flavonoids are known (*The Combined Chemical Dictionary*, Chapman & Hall/CRC, Version 5:1 June 2001). Free-B-ring flavonoids have been reported to have diverse biological activity. For example, galangin (3,5, 7-trihydroxyflavone) acts as an anti-oxidant and free radical scavenger and is believed to be a promising candidate for anti-genotoxicity and cancer chemoprevention. (Heo et al. (2001) Mutat. Res. 488:135-150). It is an inhibitor of tyrosinase monophenolase (Kubo et al. (2000) Bioorg. Med. Chem. 8:1749-1755), an inhibitor of rabbit heart carbonyl reductase (Imamura et al. (2000) J. Biochem. 127:653-658), has antimicrobial activity (Afolayan and Meyer (1997) Ethnopharmacol. 57:177-181) and antiviral activity (Meyer et al. (1997) J. Ethnopharmacol. 56:165-169). Baicalein and two other Free-B-ring flavonoids, have antiproliferative activity against human breast cancer cells. (So et al. (1997) Cancer Lett. 112:127-133).

Typically, flavonoids have been tested for activity randomly based upon their availability. Occasionally, the requirement of substitution on the B-ring has been emphasized for specific biological activity, such as the B-ring substitution required for high affinity binding to p-glycoprotein (Boumendjel et al. (2001) Bioorg. Med. Chem. Lett. 11:75-77); cardiotonic effect (Itoigawa et al. (1999) J. Ethnopharmacol. 65: 267-272), protective effect on endothelial cells against linoleic acid hydroperoxide-induced toxicity (Kaneko and Baba (1999) Biosci. Biotechnol. Biochem. 63:323-328), COX-1 inhibitory activity (Wang (2000) Phytomedicine 7:15-19) and prostaglandin endoperoxide synthase activity (Kalkbrenner et al. (1992) Pharmacology 44:1-12). Only a few publications have mentioned the significance of the unsubstituted B-ring of the Free-B-ring flavonoids. One example is the use of 2-phenyl flavones, which inhibit NADPH quinone acceptor oxidoreductase, as potential anticoagulants (Chen et al. (2001) Biochem. Pharmacol. 61:1417-1427).

The reported mechanism of action with respect to the anti-inflammatory activity of various Free-B-ring flavonoids has been controversial. The anti-inflammatory activity of the Free-B-ring flavonoids, chrysin (Liang et al. (2001) FEBS Lett. 496:12-18), wogonin (Chi et al. (2001) Biochem. Pharmacol. 61:1195-1203) and halangin (Raso et al. (2001) Life Sci. 68:921-931) has been associated with the suppression of inducible cyclooxygenase and nitric oxide synthase via activation of peroxisome-proliferator activated receptor gamma (PPARγ) and influence on degranulation and AA release (Tordera et al. (1994) Z. Naturforsch [C] 49:235-240). It has been reported that oroxylin, baicalein and wogonin inhibit 12-lipoxygenase activity without affecting cyclooxygenases (You et al. (1999) Arch. Pharm. Res. 22:18-24). More recently, the anti-inflammatory activity of wogonin, baicalin and baicalein has been reported as occurring through inhibition of inducible nitric oxide synthase and cox-2 enzyme production induced by nitric oxide inhibitors and lipopolysaccharides (Chen et al. (2001) Biochem. Pharmacol. 61:1417-1427). It has also been reported that oroxylin acts via suppression of NFκB activation (Chen et al. (2001) Biochem. Pharmacol. 61:1417-1427). Finally, wogonin reportedly inhibits inducible PGE$_2$ production in macrophages (Wakabayashi and Yasui (2000) Eur. J. Pharmacol. 406: 477-481).

Inhibition of the phosphorylation of mitogen-activated protein kinase (MAPK) and inhibition of Ca$^{2+}$ ionophore A23187 induced PGE$_2$ release by baicalein has been reported as the mechanism of anti-inflammatory activity of *Scutellariae radix* (Nakahata et al. (1999) Nippon Yakurigaku Zasshi 114, Supp. 11:215P-219P; Nakahata et al. (1998) Am. J. Chin. Med. 26:311-323). Baicalin from *Scutellaria baicalensis* reportedly inhibits superantigenic staphylococcal exotoxins stimulated T-cell proliferation and production of IL-1β, IL-6, tumor necrosis factor-α (TNF-α), and interferon-γ (IFN-γ) (Krakauer et al. (2001) FEBS Lett. 500:52-55). Thus, the anti-inflammatory activity of baicalin has been associated with inhibiting the pro-inflammatory cytokines mediated signaling pathways activated by superantigens. However, it has also been proposed that the anti-inflammatory activity of baicalin is due to the binding of a variety of chemokines, which limit their biological activity (Li et al. (2000) Immunopharmacol. 49:295-306). Recently, the effects of baicalin on adhesion molecule expression induced by thrombin and thrombin receptor agonist peptide (Kimura et al. (2001) Planta Med. 67:331-334), as well as, the inhibition of MAPK cascade (Nakahata et al. (1999) Nippon Yakurigaku Zasshi 114, Supp 11:215P-219P; Nakahata et al. (1998) Am. J. Chin Med. 26:311-323) have been reported.

The Chinese medicinal plant *Scutellaria baicalensis* contains significant amounts of Free-B-ring flavonoids, including baicalein, baicalin, wogonin and baicalenoside. Traditionally, this plant has been used to treat a number of conditions including clearing away heat, purging fire, dampness-warm and summer fever syndromes; polydipsia resulting from high fever; carbuncle, sores and other pyogenic skin infections; upper respiratory infections such as acute tonsillitis, laryngopharyngitis and scarlet fever; viral hepatitis; nephritis; pelvitis; dysentery; hematemesis and epistaxis. This plant has also traditionally been used to prevent miscarriage (see *Encyclopedia of Chinese Traditional Medicine*, ShangHai Science and Technology Press, ShangHai, China, 1998). Clinically, *Scutellaria* is now used to treat conditions such as pediatric pneumonia, pediatric bacterial diarrhea, viral hepatitis, acute gallbladder inflammation, hypertension, topical acute inflammation resulting from cuts and surgery, bronchial asthma and upper respiratory infections (*Encyclopedia of Chinese Traditional Medicine*, ShangHai Science and Technology Press, ShangHai, China, 1998). The pharmacological efficacy of *Scutellaria* roots for treating bronchial asthma is reportedly related to the presence of Free-B-ring flavonoids and their suppression of eotaxin associated recruitment of eosinophils (Nakajima et al. (2001) Planta Med. 67(2: 132-135).

To date, a number of naturally occurring Free-B-ring flavonoids have been commercialized for varying uses. For example, liposome formulations of *Scutellaria* extracts have been utilized for skin care (U.S. Pat. Nos. 5,643,598; 5,443,983). Baicalin has been used for preventing cancer due to its inhibitory effects on oncogenes (U.S. Pat. No. 6,290,995). Baicalin and other compounds have been used as antiviral, antibacterial and immunomodulating agents (U.S. Pat. No. 6,083,921) and as natural anti-oxidants (Poland Pub. No. 9,849,256). Chrysin has been used for its anxiety reducing properties (U.S. Pat. No. 5,756,538). Anti-inflammatory flavonoids are used for the control and treatment of anorectal and colonic diseases (U.S. Pat. No. 5,858,371) and inhibition of lipoxygenase (U.S. Pat. No. 6,217,875). These compounds are also formulated with glucosamine collagen and other ingredients for repair and maintenance of connective tissue (U.S. Pat. No. 6,333,304). Flavonoid esters constitute the active ingredients for cosmetic compositions (U.S. Pat. No. 6,235,294). U.S. application Ser. No. 10/091,362, filed Mar. 1, 2002, entitled "Identification of Free-B-ring Flavonoids as Potent COX-2 Inhibitors," discloses a method for inhibiting the cyclooxygenase enzyme COX-2 by administering a composition comprising a Free-B-ring flavonoid or a composition containing a mixture of Free-B-ring flavonoids to a host in need thereof. This is the first report of a link between Free-B-ring flavonoids and COX-2 inhibitory activity. This application is specifically incorporated herein by reference in its entirety.

Japanese Pat. No. 63027435, describes the extraction, and enrichment of baicalein and Japanese Pat. No. 61050921 describes the purification of baicalin.

Flavans include compounds illustrated by the following general structure:

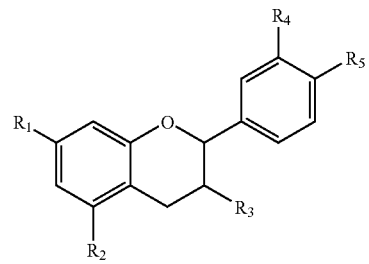

wherein $R_1$, $R_2$, $R_3$, $R_4$ and $R_5$ are independently selected from the group consisting of —H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters, and their chemical derivatives thereof, a carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, and carbonate, etc.

Catechin is a flavan, found primarily in *Acacia*, having the following structure

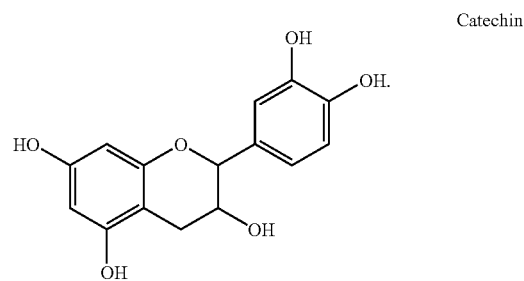

Catechin works both alone and in conjunction with other flavonoids found in tea, and has both antiviral and antioxidant activity. Catechin has been shown to be effective in the treatment of viral hepatitis. It also appears to prevent oxidative damage to the heart, kidney, lungs and spleen and has been shown to inhibit the growth of stomach cancer cells.

Catechin and its isomer epicatechin inhibit prostaglandin endoperoxide synthase with an IC$_{50}$ value of 40 μM. (Kalkbrenner et al. (1992) Pharmacol. 44:1-12). Five flavan-3-ol derivatives, including (+)-catechin and gallocatechin, isolated from the four plant species, *Atuna racemosa, Syzygium carynocarpum, Syzygium malaccense* and *Vantanea peruviana*, exhibit equal to or weaker inhibitory activity against COX-2, relative to COX-1, with IC$_{50}$ values ranging from 3.3 μM to 138 μM (Noreen et al. (1998) Planta Med. 64:520-524). (+)-Catechin, isolated from the bark of *Ceiba pentandra*, inhibits COX-1 with an IC$_{50}$ value of 80 μM (Noreen et al. (1998) J. Nat. Prod. 61:8-12). Commercially available pure (+)-catechin inhibits COX-1 with an $IC_{50}$ value of around 183 to 279 µM, depending upon the experimental conditions, with no selectivity for COX-2 (Noreen et al. (1998) J. Nat. Prod. 61:1-7).

Green tea catechin, when supplemented into the diets of Sprague dawley male rats, lowered the activity level of platelet $PLA_2$ and significantly reduced platelet cyclooxygenase levels (Yang et al. (1999) J. Nutr. Sci. Vitaminol. 45:337-346). Catechin and epicatechin reportedly weakly suppress cox-2 gene transcription in human colon cancer DLD-1 cells ($IC_{50}$=415.3 µM) (Mutoh et al. (2000) Jpn. J. Cancer Res. 91:686-691). The neuroprotective ability of (+)-catechin from red wine results from the antioxidant properties of catechin, rather than inhibitory effects on intracellular enzymes, such as cyclooxygenase, lipoxygenase or nitric oxide synthase (Bastianetto et al. (2000) Br. J. Pharmacol. 131:711-720). Catechin derivatives purified from green tea and black tea, such as epigallocatechin-3-gallate (EGCG), epigallocatechin (EGC), epicatechin-3-gallate (ECG) and theaflavins showed inhibition of cyclooxygenase- and lipoxygenase-dependent metabolism of AA in human colon mucosa and colon tumor tissues (Hong et al. (2001) Biochem. Pharmacol. 62:1175-1183) and induced cox-2 gene expression and $PGE_2$ production (Park et al. (2001) Biochem. Biophys. Res. Commun. 286:721-725). Epiafzelechin isolated from the aerial parts of *Celastrus orbiculatus* exhibited dose-dependent inhibition of COX-1 activity with an $IC_{50}$ value of 15 µM and also demonstrated anti-inflammatory activity against carrageenin-induced mouse paw edema following oral administration at a dosage of 100 mg/kg (Min et al. (1999) Planta Med. 65:460-462).

Catechin and its derivatives from various plant sources, especially from green tea leaves, have been used in the treatment of HPV infected *Condyloma acuminata* (Cheng, U.S. Pat. No. 5,795,911) and in the treatment of hyperplasia caused by papilloma virus (Cheng, U.S. Pat. Nos. 5,968,973 and 6,197,808). Catechin and its derivatives have also been used topically to inhibit angiogenesis in mammalian tissue, in conditions such as skin cancer, psoriasis, spider veins or under eye circles (Anderson, U.S. Pat. No. 6,248,341), against UVB-induced tumorigenesis in mice (Agarwal et al. (1993) Photochem. Photobiol. 58:695-700), for inhibiting nitric oxide synthase at the level of gene expression and enzyme activity (Chan, U.S. Pat. No. 5,922,756), and as hair-growing agents (Takahashi, U.S. Pat. No. 6,126,940). Catechin-based compositions have also been formulated with other extracts and vitamins for treatment of acne (Murad, U.S. Pat. No. 5,962,517), hardening the tissue of digestive organs (Shi, U.S. Pat. No. 5,470, 589) and for inhibiting 5 alpha-reductase activity in treating androgenic disorder related diseases and cancers (Liao, U.S. Pat. No. 5,605,929). Green tea extract has been formulated with seven other plant extracts for reducing inflammation by inhibiting the COX-2 enzyme, without identification of any of the specific active components (Mewmark, U.S. Pat. No. 6,264,995).

*Acacia* is a genus of leguminous trees and shrubs. The genus *Acacia* includes more than 1,000 species belonging to the family of Leguminosae and the subfamily of Mimosoideae. *Acacias* are distributed worldwide in places such as tropical and subtropical areas of Central and South America, Africa, parts of Asia, as well as, Australia, which has the largest number of endemic species. *Acacias* are present primarily in dry and arid regions where the forests are often in the nature of open thorny shrubs. The genus *Acacia* is divided into 3 subgenera based mainly on leaf morphology— *Acacia, Aculiferum* and Heterophyllum. Based on the nature of the leaves of mature trees, however, the genus *Acacia* can be divided into two "popular" groups—the typical bipinnate-leaved species and the phyllodenous species. A phyllode is a modified petiole expanded into a leaf-like structure with no leaflets, an adaptation to xerophytic conditions. The typical bipinnate-leaved species are found primarily throughout the tropics, whereas the phyllodenous species occur mainly in Australia. More than 40 species of *Acacia* have been reported in India. Gamble in his book entitled *Flora of Madras Presidency* listed 23 native species for southern India, 15 of which are found in Tamil Nadu. Since that time, however, many new *Acacia* species have been introduced to India and approximately 40 species are now found in Tamil Nadu itself. The indigenous species are primarily thorny trees or shrubs and a few are thorny stragglers, such as *A. caesia, A. pennata* and *A. sinuata*. Many species have been introduced from Africa and Australia, including *A. mearnsii, A. picnantha* and *A. dealbata*, which have bipinnate leaves and *A. auriculiformis, A. holoserecia* and *A. mangium*, which are phyllodenous species.

*Acacias* are very important economically, providing a source of tannins, gums, timber, fuel and fodder. Tannins, which are isolated primarily from the bark, are used extensively for tanning hides and skins. Some *Acacia* barks are also used for flavoring local spirits. Some indigenous species like *A. sinuata* also yield saponins, which are any of various plant glucosides that form soapy lathers when mixed and agitated with water. Saponins are used in detergents, foaming agents and emulsifiers. The flowers of some *Acacia* species are fragrant and used to make perfume. For example, cassie perfume is obtained from *A. ferrugenea*. The heartwood of many *Acacias* is used for making agricultural implements and also provides a source of firewood. *Acacia* gums find extensive use in medicine and confectionary and as sizing and finishing materials in the textile industry. Lac insects can be grown on several species, including *A. nilotica* and *A. catechu*. Some species have been used for forestation of wastelands, including *A. nilotica*, which can withstand some water inundation and a few such areas have become bird sanctuaries.

To date, approximately 330 compounds have been isolated from various *Acacia* species. Flavonoids, a type of water-soluble plant pigments, are the major class of compounds isolated from *Acacias*. Approximately 180 different flavonoids have been identified, 111 of which are flavans. Terpenoids are second largest class of compounds isolated from species of the *Acacia* genus, with 48 compounds having been identified. Other classes of compounds isolated from *Acacia* include, alkaloids (28), amino acids/peptides (20), tannins (16), carbohydrates (15), oxygen heterocycles (15) and aliphatic compounds (10). (Buckingham, in *The Combined Chemical Dictionary*, Chapman & Hall CRC, version 5:2, December 2001).

Phenolic compounds, particularly flavans are found in moderate to high concentrations in all *Acacia* species (Abdulrazak et al. (2000) J. Anim. Sci. 13:935-940). Historically, most of the plants and extracts of the *Acacia* genus have been utilized as astringents to treat gastrointestinal disorders, diarrhea, indigestion and to stop bleeding (Vautrin (1996) Universite Bourgogne (France) European abstract 58-01C:177; Saleem et al. (1998) Hamdard Midicus. 41:63-67). The bark and pods of *A. arabica* Willd. contain large quantities of tannins and have been utilized as astringents and expectorants (Nadkarni (1996) India Materia Medica, Bombay Popular Prakashan, pp. 9-17). Diarylpropanol derivatives, isolated from stem bark of *A. tortilis* from Somalia, have been reported to have smooth muscle relaxing effects (Hagos et al. (1987) Planta Med. 53:27-31, 1987). It has also been reported that terpenoid saponins isolated from *A. victoriae* have an inhibitory effect on dimethylbenz(a)anthracene-induced murine skin carcinogenesis (Hanausek et al. (2000) Proc. Am. Assoc. Can. Res. Annu. Mtg. 41:663) and induce apoptosis (Haridas et al. (2000) Proc. Am. Assoc. for Can. Res. Annu. Mtg. 41:600). Plant extracts from *A. nilotica* have been reported to have spasmogenic, vasoconstrictor and anti-hypertensive activity (Amos et al. (1999) Phytotherapy Research 13:683-685; Gilani et al. (1999) Phytotherapy Research 13:665-669), and antiplatelet aggregatory activity (Shah et al. (1997) Gen. Pharmacol. 29:251-255). Anti-inflammatory activity has been reported for *A. nilotica*. It was speculated that flavonoids, polysaccharides and organic acids were potential active components (Dafallah and Al-Mustafa (1996) Am. J. Chin. Med. 24:263-269). To date, the only reported 5-lipoxygenase inhibitor isolated from *Acacia* is a monoterpenoidal carboxamide (Seikine et al. (1997) Chem. Pharm. Bull. (Tokyo) 45:148-11).

*Acacia* gums have been formulated with other plant ingredients and used for ulcer prevention without identification of any of the active components (Fuisz, U.S. Pat. No. 5,651,987). *Acacia* gums have also been formulated with other plant ingredients and used to improve drug dissolution (Blank, U.S. Pat. No. 4,946,684), by lowering the viscosity of nutritional compositions (Chancellor, U.S. Pat. No. 5,545,411).

The extract from the bark of *Acacia* was patented in Japan for external use as a whitening agent (Abe, JP10025238), as a glucosyl transferase inhibitor for dental applications (Abe, JP07242555), as a protein synthesis inhibitor (Fukai, JP 07165598), as an active oxygen-scavenging agent for external skin preparations (Honda, J P 07017847, Bindra U.S. Pat. No. 6,1266,950), and as a hyaluronidase inhibitor for oral consumption to prevent inflammation, pollinosis and cough (Ogura, JP 07010768).

Review of the literature has revealed no human clinical applications using mixtures of Free-B-ring flavonoids and flavans for relief of pain or measuring biochemical clinical outcomes for osteoarthritis treatment. This report appears to be the first randomized, double blind, placebo controlled study of the safety and efficacy of these compounds in humans.

SUMMARY OF THE INVENTION

The present invention includes a novel composition of matter comprised of a mixture of Free-B-ring flavonoids and flavans. This novel composition of matter is referred to herein as Univestin™. The ratio of Free-B-ring flavonoids to flavans in the composition of matter can be adjusted based on the indications and the specific requirements with respect to prevention and treatment of a specific disease or condition. Generally, the ratio of Free-B-ring flavonoids to flavans can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment the Free-B-ring flavonoids are isolated from a plant or plants in the *Scutellaria* genus of plants and flavans are isolated from a plant or plants in the *Acacia* genus of plants.

The present invention further includes methods that are effective in simultaneously inhibiting both the COX-2 and 5-LO enzymes. The method for the simultaneous dual inhibition of the COX-2 and 5-LO pathways is comprised of administering a composition comprising a mixture of Free-B-ring flavonoids and flavans synthesized and/or isolated from a single plant or multiple plants to a host in need thereof. The efficacy of this method was demonstrated with purified enzymes, in different cell lines, multiple animal models and eventually in a human clinical study. The ratio of Free-B-ring flavonoids to flavans in the composition can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment, the Free-B-ring flavonoids are isolated from a plant or plants in the *Scutellaria* genus of plants and flavans are isolated from a plant or plants in the *Acacia* genus of plants.

The present invention further includes methods for the prevention and treatment of COX-2 and 5-LO mediated diseases and conditions, including but not limited to menstrual cramps, arteriosclerosis, heart attack, obesity, diabetes, syndrome X, Alzheimer's disease, respiratory allergic reaction, chronic venous insufficiency, hemorrhoids, Systemic Lupus Erythromatosis, psoriasis, chronic tension headache, migraine headaches, inflammatory bowel disease; topical infections caused by virus, bacteria and fungus, sunburn, thermal burns, contact dermatitis, melanoma and carcinoma. The method for preventing and treating COX-2 and 5-LO mediated diseases and conditions is comprised of administering to a host in need thereof an effective amount of a composition comprising a mixture of Free-B-ring flavonoids and flavans synthesized and/or isolated from a single plant or multiple plants together with a pharmaceutically acceptable carrier. The ratio of Free-B-ring flavonoids to flavans can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment, the Free-B-ring flavonoids are isolated from a plant or plants in the *Scutellaria* genus of plants and flavans are isolated from a plant or plants in the *Acacia* genus of plants.

In another embodiment, the present invention includes a method for treating general joint pain and stiffness, improving mobility and physical function and preventing and treating pathological conditions of osteoarthritis and rheumatoid arthritis. The method for preventing and treating joint pain and stiffness, improving mobility and physical function and preventing and treating pathological conditions of osteoarthritis, and rheumatoid arthritis comprises administering to a host in need thereof an effective amount of a composition comprising a mixture of Free-B-ring flavonoids and flavans synthesized and/or isolated from a single plant or multiple plants together with a pharmaceutically acceptable carrier. The ratio of Free-B-ring flavonoids to flavans can be in the range of 99:1 to 1:99 Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment, the Free-B-ring flavonoids are isolated from a plant or plants in the *Scutellaria* genus of plants and flavans are isolated from a plant or plants in the *Acacia* genus of plants.

The present invention includes methods for weight loss and blood sugar control due to increased physical activity resulting from improving mobility, flexibility and physical function said method comprising administering to a host in need thereof an effective amount of a composition comprising a mixture of Free-B-ring flavonoids and flavans synthesized and/or isolated from a single plant or multiple plants and a pharmaceutically acceptable carrier. The ratio of Free-B-ring flavonoids to flavans can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment the Free-B-ring flavonoids are isolated from a plant or plants in the *Scutellaria* genus of plants and flavans are isolated from a plant or plants in the *Acacia* genus of plants.

The present invention also includes a method for modulating the production of mRNA implicated in pain pathways said method comprising administering to a host in need thereof an effective amount of a composition comprising a mixture of Free-B-ring flavonoids and flavans synthesized and/or isolated from a single plant or multiple plants and a pharmaceutically acceptable carrier. While not limited by theory, Applicant believes that the ability to modulate the production of mRNA is accomplished via a decrease, by the active ingredients in the Free-B-ring/flavan composition, in the production of mRNA by the cox-2 gene, but not the cox-1 gene. The ratio of Free-B-ring flavonoids to flavans in the composition can be in the range of 99:1 to 1:99 Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment the Free-B-ring flavonoids are isolated from a plant or plants in the *Scutellaria* genus of plants and flavans are isolated from a plant or plants in the *Acacia* genus of plants.

The Free-B-ring flavonoids, also referred to herein as Free-B-ring flavones and flavonols, that can be used in accordance with the following invention include compounds illustrated by the following general structure:

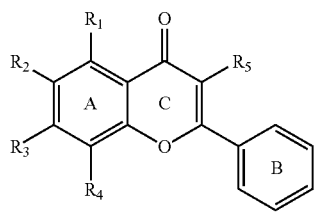

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_{3+}$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The flavans that can be used in accordance with the following invention include compounds illustrated by the following general structure:

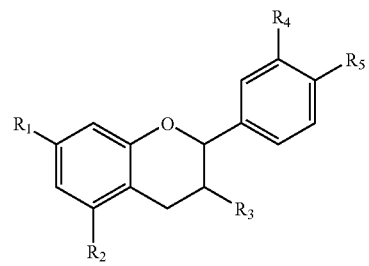

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3{}^+$X$^-$, esters of the mentioned substitution groups, including, but not limited to, gallate, acetate, cinnamoyl and hydroxyl-cinnamoyl esters, trihydroxybenzoyl esters and caffeoyl esters and their chemical derivatives thereof; carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The Free-B-ring flavonoids of this invention may be obtained by synthetic methods or extracted from the families of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberaceae. The Free-B-ring flavonoids can be extracted, concentrated, and purified from the genera of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*.

As noted above the flavans of this invention may be obtained from a plant or plants selected from the genus of *Acacia*. In a preferred embodiment, the plant is selected from the group consisting of *Acacia catechu, A. concinna, A. farnesiana, A. Senegal, A. speciosa, A. arabica, A. caesia, A. pennata, A. sinuata. A. mearnsii, A. picnantha, A. dealbata, A. auriculiformis, A. holoserecia* and *A. mangium*.

The present invention includes an evaluation of different compositions of Free-B-ring flavonoids and flavans using enzymatic and in vivo models to optimize the formulation and obtain the best potency. The efficacy and safety of this formulation is also demonstrated in human clinical studies. The present invention provides a commercially viable process for the isolation, purification and combination of *Acacia* flavans with Free-B-ring flavonoids to yield composition of matter having desirable physiological activity. The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of a mixture of Free-B-ring flavonoids and flavans synthesized and/or isolated from a single plant or multiple plants.

It is to be understood that both the foregoing general description and the following detailed description are exemplary and explanatory only and are not restrictive of the invention as claimed.

DETAILED DESCRIPTION OF THE INVENTION

Figure 1:
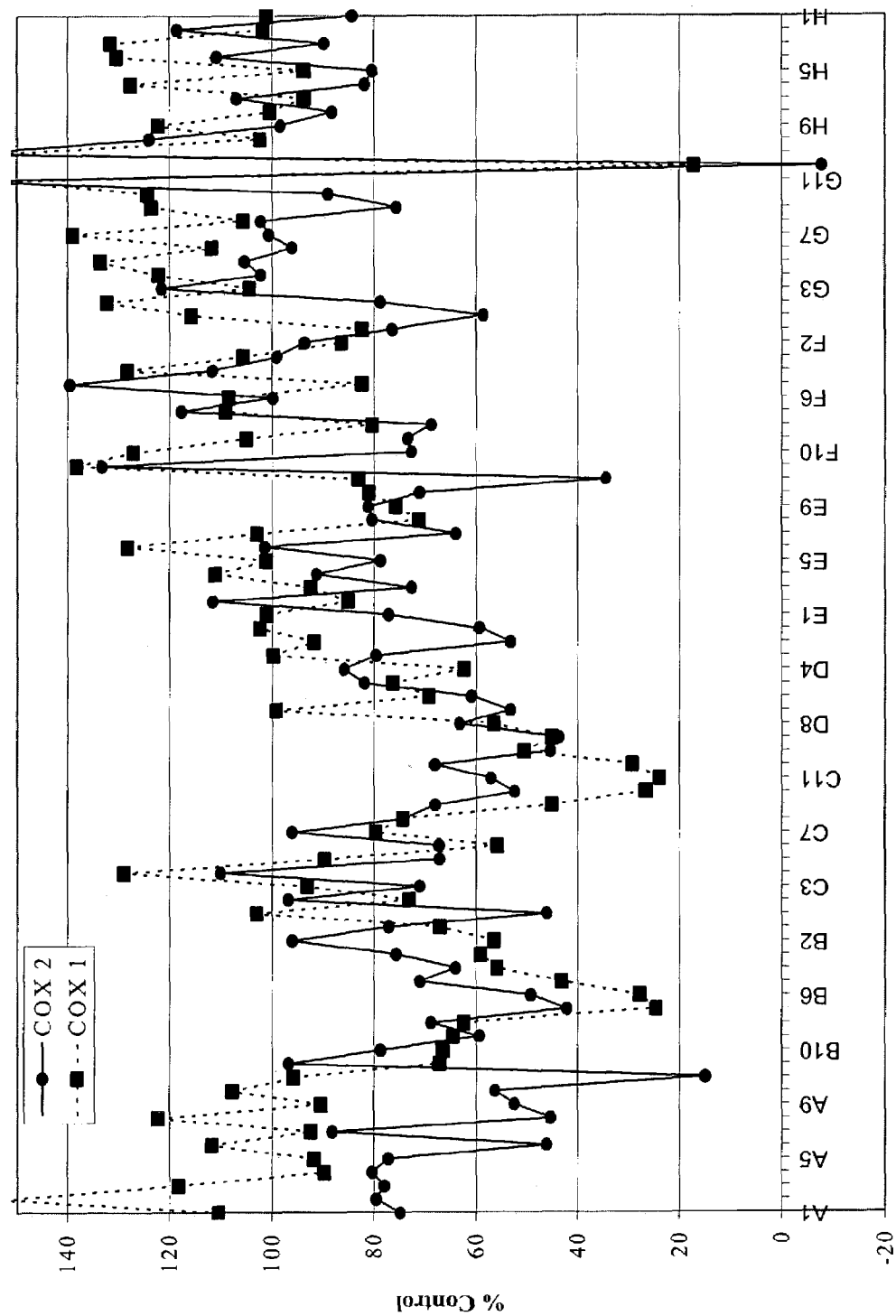
FIG. 1 depicts graphically the inhibition of COX-1 and COX-2 by HTP fractions from *Acacia catechu*. The extracts were prepared and fractionated as described in Examples 1 and 3. The extracts were examined for their inhibition of the peroxidase activity of recombinant ovine COX-1 (■) or ovine COX-2 (◆) as described in Example 2. The data is presented as percent of untreated control.

Various terms are used herein to refer to aspects of the present invention. To aid in the clarification of the description of the components of this invention, the following definitions are provided.

It is to be noted that the term "a" or "an" entity refers to one or more of that entity; for example, a flavonoid refers to one or more flavonoids. As such, the terms "a" or "an", "one or more" and "at least one" are used interchangeably herein.

"Free-B-ring Flavonoids" as used herein are a specific class of flavonoids, which have no substitute groups on the aromatic B ring, as illustrated by the following general structure:

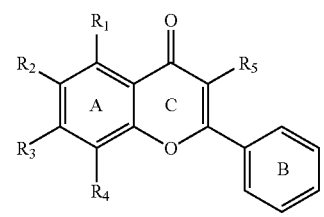

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_{3+}$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Flavans" are a specific class of flavonoids, which can be generally represented by the following general structure:

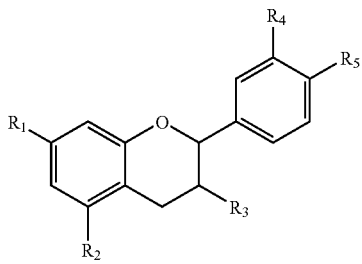

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_{3+}$X$^-$, esters of substitution groups, including, but not limited to, gallate, acetate, cinnamoyl and hydroxyl-cinnamoyl esters, trihydroxybenzoyl esters and caffeoyl esters and their chemical derivatives thereof; carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Gene expression" refers to the transcription of a gene to mRNA.

"Protein expression" refers to the translation of mRNA to a protein.

"RT-qPCR" is a method for reverse transcribing (RT) an mRNA molecule into a cDNA molecule and then quantitatively evaluating the level of gene expression using a polymerase chain reaction (PCR) coupled with a fluorescent reporter.

"Therapeutic" as used herein, includes treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired.

"Placebo" refers to the substitution of the pharmaceutically or therapeutically effective dose or amount sufficient to induce a desired biological that may alleviate the signs, symptoms or causes of a disease with a non-active substance.

A "host" or "patient" is a living subject, human or animal, into which the compositions described herein are administered.

Note that throughout this application various citations are provided. Each citation is specifically incorporated herein in its entirety by reference.

The present invention includes a novel composition of matter comprised of a mixture of Free-B-ring flavonoids and flavans. This novel composition of matter is referred to herein as Univestin™. The ratio of Free-B-ring flavonoids to flavans in the composition of matter can be adjusted based on the indications and the specific requirements with respect to prevention and treatment of a specific disease or condition. Generally, the ratio of Free-B-ring flavonoids to flavans can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment the Free-B-ring flavonoids are isolated from a plant or plants in the *Scutellaria* genus of plants and flavans are isolated from a plant or plants in the *Acacia* genus of plants.

In one embodiment of the present invention, the standardized Free-B-ring flavonoid extract is comprised of the active compounds with a purity of between 1-99% (by weight) of total Free-B-ring flavonoids as defined in examples 5, 7 and 13; Tables 5, 7, 8 and 9 and FIG. 3. Baicalin is the major active component in the extract, which accounts for approximately 50-90% (by weight) of the total Free-B-ring flavonoids. In a preferred embodiment, the standardized extract contains >70% total Free-B-ring flavonoids in which >75% of the Free-B-ring flavonoids is baicalin.

In one embodiment, the standardized flavan extract is comprised of the active compounds with a purity of between 1-99% (by weight) total flavans as defined in Example 8, 9 and 12; Tables 4, 6 and 9 and FIG. 9. Catechin is the major active component in the extract and accounts for 50-90% (by weight) of the total flavans. In a preferred embodiment, the standardized flavan extract contains >50% total flavans in which >70% of flavans is catechin.

In one embodiment Univestin™ is be produced by mixing the above two extracts or synthetic compounds in a ratio from 99:1 to 1:99. The preferred ratio of Free-B-ring flavonoids to flavans is 85:15 Free-B-ring flavonoids:flavans as defined in Example 14.

The concentration of Free-B-ring flavonoids in Univestin™ can be from about 1% to 99% and the concentration of flavans in Univestin™ can be from 99% to 1%. In a preferred embodiment of the invention, the concentration of total Free-B-ring flavonoids in Univestin™ is approximately 75% with a baicalin content of approximately 60% of total weight of the Univestin™; and the concentration of total flavans in Univestin™ is approximately 10% with a catechin content of approximately 9%. In this embodiment, the total active components (Free-B-ring flavonoids plus flavans) in Univestin™ are >80% of the total weight.

The present invention also includes methods that are effective in simultaneously inhibiting both the COX-2 and 5-LO enzymes. The method for the simultaneous dual inhibition of the COX-2 and 5-LO pathways is comprised of administering a composition comprising a mixture of Free-B-ring flavonoids and flavans synthesized and/or isolated from a single plant or multiple plants to a host in need thereof. The ratio of Free-B-ring flavonoids to flavans in the composition can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment, the Free-B-ring flavonoids are isolated from a plant or plants in the *Scutellaria* genus of plants and flavans are isolated from a plant or plants in the *Acacia* genus of plants.

The present further includes methods for the prevention and treatment of COX-2 and 5-LO mediated diseases and conditions. The method for preventing and treating COX-2 and 5-LO mediated diseases and conditions is comprised of administering to a host in need thereof an effective amount of a composition comprising a mixture of Free-B-ring flavonoids and flavans synthesized and/or isolated from a single plant or multiple plants together with a pharmaceutically acceptable carrier. The ratio of Free-B-ring flavonoids to flavans can be in the range of 99:1 Free-B-ring flavonoids:flavans to 1:99 of Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment, the Free-B-ring flavonoids are isolated from a plant or plants in the *Scutellaria* genus of plants and flavans are isolated from a plant or plants in the *Acacia* genus of plants.

In yet a further embodiment, the present includes a method for treating general joint pain and stiffness, improving mobility and physical function and preventing and treating pathological conditions of osteoarthritis and rheumatoid arthritis. The method for preventing and treating joint pain and stiffness, improving mobility and physical function and preventing and treating pathological conditions of osteoarthritis, and rheumatoid arthritis is comprised of by administering to a host in need thereof an effective amount of a composition comprising a mixture of Free-B-ring flavonoids and flavans synthesized and/or isolated from a single plant or multiple plants together with a pharmaceutically acceptable carrier. The ratio of Free-B-ring flavonoids to flavans can be in the range of 99:1 to 1:99 Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment, the Free-B-ring flavonoids are isolated from a plant or plants in the *Scutellaria* genus of plants and flavans are isolated from a plant or plants in the *Acacia* genus of plants.

The present invention also includes a method for modulating the production of mRNA implicated in pain pathways said method comprising administering to a host in need thereof an effective amount of a composition comprising a mixture of Free-B-ring flavonoids and flavans synthesized and/or isolated from a single plant or multiple plants and optionally a pharmaceutically acceptable carrier. The ratio of Free-B-ring flavonoids to flavans can be in the range of 99:1 to 1:99 Free-B-ring flavonoids:flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of the invention, the ratio of Free-B-ring flavonoids:flavans in the composition of matter is approximately 85:15. In a preferred embodiment the Free-B-ring flavonoids are isolated from a plant or plants in the *Scutellaria* genus of plants and flavans are isolated from a plant or plants in the *Acacia* genus of plants.

The Free-B-ring flavonoids that can be used in accordance with the method of this invention include compounds illustrated by the general structure set forth above. The Free-B-ring flavonoids of this invention may be obtained by synthetic methods or may be isolated from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae, and Zingiberaceae. The Free-B-ring flavonoids can also be extracted, concentrated, and purified from the genera of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus*, and *Alpinia*.

The Free-B-ring flavonoids can be found in different parts of plants, including but not limited to stems, stem barks, twigs, tubers, roots, root barks, young shoots, seeds, rhizomes, flowers and other reproductive organs, leaves and other aerial parts. Methods for the isolation and purification of Free-B-ring flavonoids are described in U.S. application Ser. No. 10/091,362, filed Mar. 1, 2002, entitled "Identification of Free-B-ring Flavonoids as Potent COX-2 Inhibitors," which is incorporated herein by reference in its entirety.

The flavans that can be used in accordance with the method of this invention include compounds illustrated by the general structure set forth above. The flavans of this invention may be obtained by synthetic methods or may be isolated from a plant or plants selected from the *Acacia* genus of plants. In a preferred embodiment, the plant is selected from the group consisting of *Acacia catechu, A. concinna, A. farnesiana, A. Senegal, A. speciosa, A. arabica, A. caesia, A. pennata, A. sinuata. A. mearnsii, A. picnantha, A. dealbata, A. auriculiformis, A. holoserecia* and *A. mangium*.

The flavans can be found in different parts of plants, including but not limited to stems, stem barks, trunks, trunk barks, twigs, tubers, roots, root barks, young shoots, seeds, rhizomes, flowers and other reproductive organs, leaves and other aerial parts. Methods for the isolation and purification of flavans are described in U.S. application Ser. No. 10/104,477, filed Mar. 22, 2002, entitled "Isolation of a Dual COX-2 and 5-Lipoxygenase Inhibitor from *Acacia*," which is incorporated herein by reference in its entirety.

The present invention implements a strategy that combines a series of in vivo studies as well as in vitro biochemical, cellular, and gene expression screens to identify active plant extracts and components that specifically inhibit COX-2 and 5-LO enzymatic activity, and impact cox-2, but not cox-1 mRNA production. The methods used herein to identify active plant extracts and components that specifically inhibit COX-2 and 5-LO pathways are described in Examples 1 to 13 (FIGS. 1-10). These methods are described in greater detail in U.S. application Ser. No. 10/091,362, filed Mar. 1, 2002, entitled "Identification of Free-B-ring Flavonoids as Potent COX-2 Inhibitors" and U.S. application Ser. No. 10/104,477, filed Mar. 22, 2002, entitled "Isolation of a Dual COX-2 and 5-Lipoxygenase Inhibitor from *Acacia*," each of which is specifically incorporated herein by reference in its entirety.

These studies resulted in the discovery of a novel composition of matter referred to herein as Univestin™, which is comprised of a proprietary blending of two standardized extracts, which contain Free-B-ring flavonoids and flavans, respectively. A general example for preparing such a composition is provided in Example 14 using two standardized extracts isolated from *Acacia* and *Scutellaria*, respectively, together with one or more excipients. The *Acacia* extract used in Example 14 contained >60% total flavans, as catechin and epicatechin, and the *Scutellaria* extract contained >70% Free-B-ring flavonoids, which was primarily baicalin. The *Scutellaria* extract contained other minor amounts of Free-B-ring flavonoids as set forth in Table 11. One or more excipients are optionally added to the composition of matter. The amount of excipient added can be adjusted based on the actual active content of each ingredient desired. A blending table for each individual batch of product must be generated based on the product specification and QC results for individual batch of ingredients. Additional amounts of active ingredients in the range of 2-5% are recommended to meet the product specification. Example 14 illustrates a blending table that was generated for one batch of Univestin™ (Lot#G1702-COX-2). Different blending ratios of the formulated Univestin™ product were tested for their ability to inhibit COX-2 and 5-LO enzyme activities, and to reduce cox mRNA production as described in Examples 15-17.

The COX-2 inhibition assay relied on the activity of the enzyme peroxidase in the presence of heme and arachidonic acid. In order to screen for compounds that inhibited COX-1 and COX-2 activity, a high throughput, in vitro assay was developed that utilized inhibition of the peroxidase activity of both enzymes as illustrated in Examples 2 and 6. After isolating plant fractions that inhibited COX-2 activity in the screening process, the two individual standardized extracts, one composed primarily of Free-B-ring flavonoids (isolated from *Scutellaria*) and the other of flavans (isolated from *Acacia*), were compared, as well as, purified components from each extract and different ratios of the combined extracts by titrating against a fixed amount of the COX-1 and COX-2 enzymes. This study revealed that the purified Free-B-ring flavonoids, baicalin and baicalein isolated from *Scutellaria baicalensis* and the purified flavan, catechin isolated from *Acacia catechu*, inhibited COX-2 and 5-LO activity. Additionally, each of the individual standardized extracts, which contained concentrations of Free-B-ring flavonoids in the range of 10-90% (based on HPLC) and flavans in the range of 10-90% (based on HPLC), also inhibited COX-2 and 5-LO activity. Finally, the study revealed that compositions containing mixtures of each of the individual standardized extracts having ratios of Free-B-ring flavonoids to flavans of approximately 80:20, 50:50, and 20:80, were also all highly effective at inhibiting COX-2 enzymatic activity in vitro. The results are set forth in FIGS. 11-13).

Figure 14:
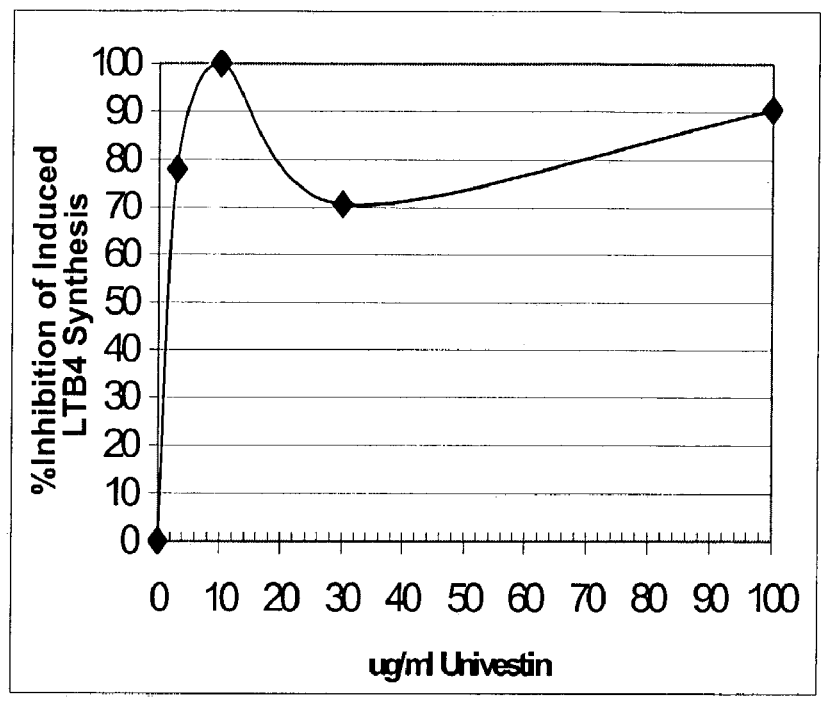
FIG. 14 depicts the effect of increasing concentrations of Univestin™ on the amount of LPS-induced newly synthesized $LTB_4$ (♦) as determined by ELISA in THP-1 or HT-29 cells (ATCC). The activity of the combination extract is expressed as % inhibition of induced $LTB_4$ synthesis.

Example 16 describes cell assays performed that targeted inhibition of compounds in the breakdown of arachidonic acid in the 5-LO pathway, namely $LTB_4$. The results are set forth in FIGS. 14 and 15.

Figure 16:
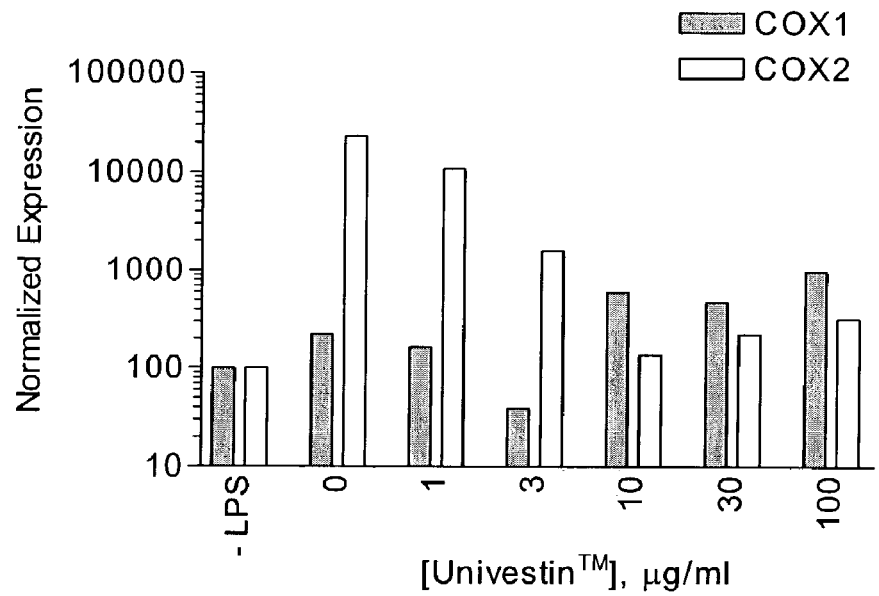
FIG. 16 compares the effect of various concentrations of Univestin™ on cox-1 and cox-2 gene expression. The expression levels are standardized to 18S rRNA expression levels (internal control) and then normalized to the no-treatment, no-LPS condition. This Figure demonstrates a decrease in cox-2, but not cox-1 gene expression following LPS-stimulation and exposure to Univestin™.
Figure 17:
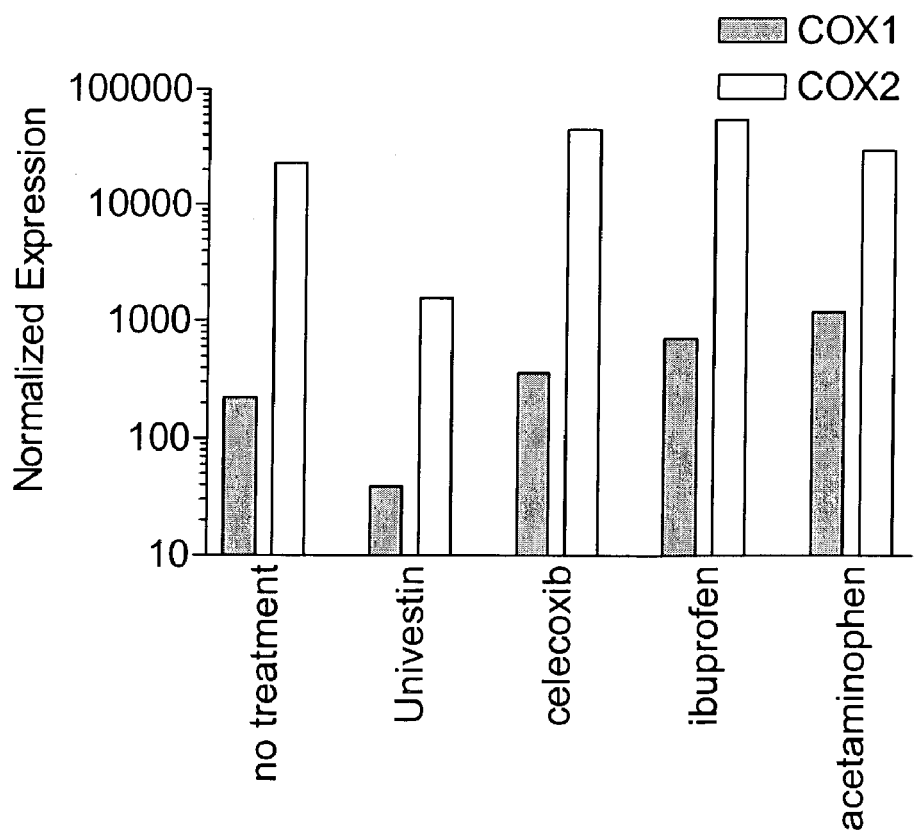
FIG. 17 compares the effect of 3 μg/mL Univestin™ on cox-1 and cox-2 gene expression with the equivalent concentration of other NSAIDs. The expression levels are standardized to 18S rRNA expression levels (internal control) and then normalized to the no-treatment, no-LPS condition.

Example 17 describes an experiment performed to determine differential inhibition of the cox-2 gene by Univestin™. Gene expression data was obtained for the inhibition of cox-1 and cox-2 mRNA production in a semi-quantitative RT-qPCR assay. The results are set forth in FIGS. 16 and 17. With reference to FIG. 16 it can be seen that Univestin™ inhibited cox-2 mRNA production without effecting cox-1 gene expression. In addition, when compared with other COX-2 inhibitor drugs, Univestin™ was able to decrease LPS-stimulated increases in cox-1 and cox-2 gene expression. Importantly, celecoxib and ibuprofen both increased cox-2 gene expression (FIG. 17).

In vivo efficacy was demonstrated by the application of skin irritating substances, such as AA, to the ears of mice and measuring the reduction of swelling in mice treated with Univestin™ as described in Example 18. The results are set forth in FIG. 18. Additionally, efficacy at the site of inflammation and pain, was determined by the injection of an irritant into the ankle joints of mice and measuring the reduction of swelling in mice treated with Univestin™, as described in Example 19. The results are set forth in FIG. 19.

Individual standardized extracts containing concentrations of Free-B-ring flavonoids in the range of 10-99% (based on HPLC) and flavans in the range of 10-99% (based on HPLC) as well as the product Univestin™ were tested for toxicity in mice with chronic and acute administration (data not shown). In the chronic administration protocol, mice were fed the test articles by oral gavage with daily doses of 90 mg/kg (equivalent to the human daily dose of 500 mg), 450 mg/kg (five times the daily-dose equivalent) and 900 mg/kg (ten times the daily-dose equivalent). Mice showed no adverse effects in terms of weight gain, physical appearance or behavior. Gross necropsy results showed no organ abnormalities and histology of the stomach, kidney, and liver showed no differences compared to untreated control mice. Full blood work measuring electrolytes, blood proteins, blood enzymes, and liver enzymes showed no abnormalities compared to the untreated control mice. In the acute protocol, individual standardized extracts containing concentrations of Free-B-ring flavonoids in the range of 10-99% (based on HPLC) and flavans in the range of 10-99% (based on HPLC) as well as the product Univestin™ given at 2 grams/kg (20 times the daily-dose equivalent) showed no abnormalities in weight gain, appearance, behavior, gross necropsy appearance of organs, histology of stomach, kidney, and liver or blood work.

Example 20 describes a clinical study performed to evaluate the efficacy of Univestin™ on the relief of pain caused by rheumatoid arthritis or osteoarthritis of the knee and/or hip. The study was a single-center, randomized, double-blind, placebo-controlled study. Sixty subjects (n=60) with rheumatoid arthritis or osteoarthritis of the knee and/or hip were randomly placed into four groups and treated for 90 days with a placebo, Univestin™ (250 mg/day or 500 mg/day) or Celebrex™ (also known as celecoxib) (200 mg/day). The Univestin™, as illustrated in Example 14, Table 11, consisted of a proprietary blend of standardized extract of *Scutellaria baicalensis Georgi* with a baicalin content of 82.2% (w/w) and total Free-B-ring Flavonoids >90% (w/w) and a standardized extract of *Acacia catechu* with a total flavan content of 77.2% (w/w) in a ratio of 85:15. Celebrex™ is a trade name for a prescription drug that is a COX-2 selective inhibitor. Table 12 sets forth the WOMAC index scores for pain, stiffness and function before treatment (baseline scores) and at 30, 60 and 90 days. Table 13 sets forth the absolute changes in WOMAC index scores for pain, stiffness and function after treatment for 30, 60 and 90 days. FIGS. 20-31 illustrate the results of this study graphically plotting the 95% confidence intervals for all data.

As shown in the FIGS. 20 to 31, the WOMAC composite scores and individual subscores, related to pain, stiffness and physical function exhibited significant improvements during administration of Univestin™ compared to the placebo group. Further, Univestin™ exhibited a similar effectiveness on pain relieve, better effectiveness at decreasing stiffness, and marked improvement of physical function compared to the prescription drug Celebrex™. The greatest significance can be seen in comparing each dose of Univestin™ to the placebo and celecoxib in relieving pain, stiffness and functional impairment associated with osteoarthritis or rheumatoid arthritis.

Multiple post-hoc comparisons for each treatment group pairs within the Analysis of Variance models showed that Univestin™ at 500 mg/day was significantly more effective than celecoxib at 200 mg/day for the reduction of pain caused osteoarthritis during the 30 days (p=0.020) of treatment. In addition, the administration of a dose of 500 mg/day of Univestin™ was also significantly more effective than the placebo for the reduction of pain within 30 days (p=0.044), 60 days (p=0.032) and 90 days (p=0.001) of treatment. Celecoxib at 200 mg/day showed significance for the reduction of pain vs. the placebo at 60 days (p=0.009) of treatment. At 90 days, the 500 mg/day Univestin™ dose showed significantly higher effectiveness compared to the 250 mg/day dose within 90 days (p=0.038) of treatment.

Univestin™ at 250 mg/day was significantly more effective than the placebo for the reduction of stiffness caused by osteoarthritis, within 30 days (p=0.00), 60 days (p=0.027) and 90 days (p=0.015) of treatment. In addition, Univestin™ at a dose of 500 mg/day was significantly more effective than placebo for reduction of stiffness caused by osteoarthritis, within 30 days (p=0.001) and 90 days (p=0.005) of treatment. Celecoxib at 200 mg/day showed significantly more effectiveness than the placebo for the reduction of stiffness caused by osteoarthritis only at 30 days (p=0.023) of treatment.

For reduction of functional impairment caused by osteoarthritis, Univestin™ was significantly more effective than celecoxib at 200 mg/day within 30 days (p=0.010) of treatment. In addition, the 250 mg/day dose of Univestin™ was also significantly more effective than placebo for the reduction of functional impairment caused by osteoarthritis within 30 days (p=0.010), 60 days (p=0.043) and 90 days (p=0.039) of treatment. The 500 mg/day dose of Univestin™ was more effective than celecoxib at 200 mg/day within 30 days (p=0.015), 60 days (p=0.043) and 90 days (0.039) of treatment. Finally, the 500 mg/day dose of Univestin™ was also significantly more effective than placebo for the reduction of functional impairment caused by osteoarthritis within 30 days (p=0.015), 60 days (p=0.016) and 90 days (p=0.003) of treatment.

These results suggest that Univestin™, particularly at a dosage of 500 mg/day, is much more effective than the placebo and celecoxib at relieving pain, stiffness and improving functional impairment caused by osteoarthritis. Additionally, Univestin™ administered at a dosage of 250 mg/day is also very effective at relieving stiffness and improving functional impairment caused by osteoarthritis compared to the placebo and celecoxib. Celecoxib also showed only marginal improvement overall in relieving pain, stiffness and functional impairment caused by osteoarthritis.

Figure 32:
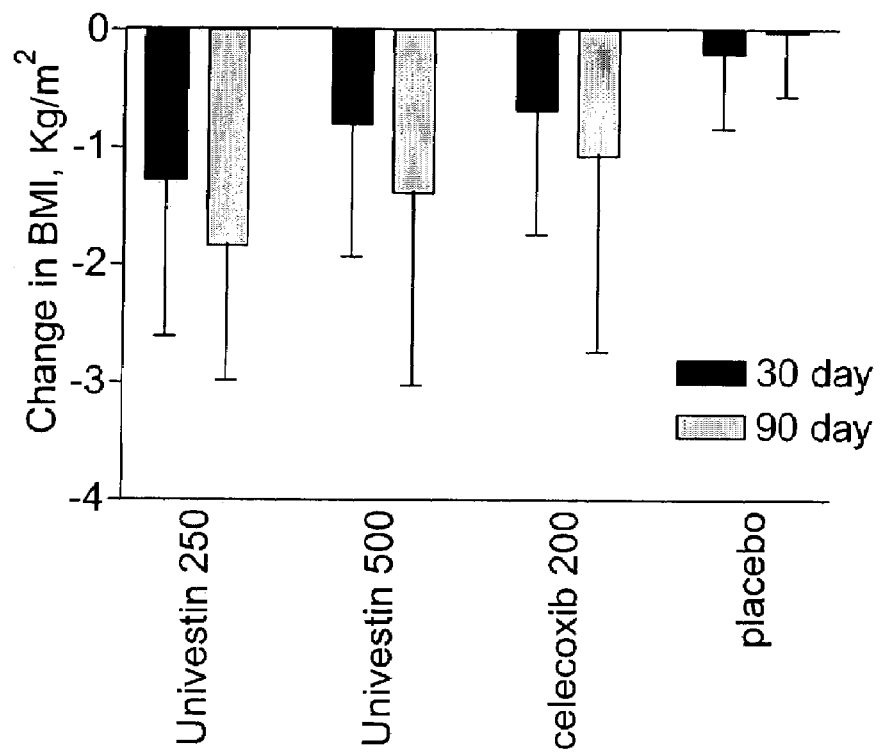
FIG. 32 shows the effect of Univestin™ at doses of 250 and 500 mg/day on decreasing BMI compared to celecoxib at 200 mg/day and the placebo.
Figure 33:
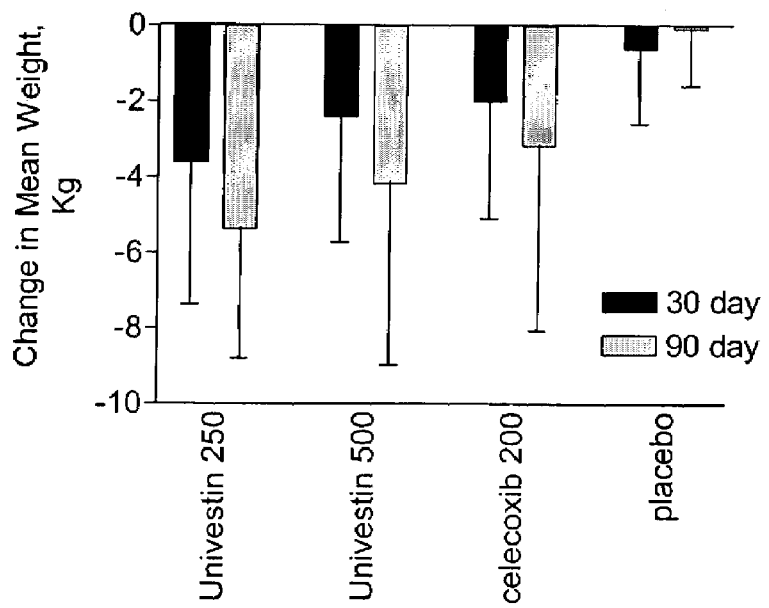
FIG. 33 shows the effect of Univestin™ at doses of 250 and 500 mg/day on decreasing weight compared to celecoxib at 200 mg/day and the placebo.

In addition to the effects of Univestin™ on pain, stiffness and functional impairment caused by osteoarthritis, Example 21 shows a measurable effect by Univestin™ on body mass index (BMI) and weight loss. While not limited by theory, this effect may be due to an increase in mobility as a result of the administration of an anti-inflammatory or may also be due to a specific mechanism that increases metabolism or reduces the utilization of fats and carbohydrates in the body. Table 14 shows the effect of Univestin™ administered at a dose of 250 and 500 mg/day as well as celecoxib and placebo on weight and BMI after 30 and 90 days of treatment. The results are illustrated graphically in FIGS. 32 and 33. With reference to FIGS. 32 and 33, it can be seen that Univestin™ administered at a dosage of both 250 and 500 mg/day resulted in a significant drop in weight and BMI after thirty days, with weight loss almost doubling after 90 days. Celecoxib had a smaller effect on weight and BMI as compared to Univestin™.

Multiple post-hoc comparisons for each treatment group pairs with the Analysis of Variance models were also performed for weight loss and BMI as described in Example 21. These analyses showed that Univestin™ at 250 mg/day and 500 mg/day doses caused statistically significant weight loss (p=0.011 vs. p=0.118) against the placebo after 30 days of treatment. Celecoxib did not cause significant weight loss against placebo at 30 days. The weight loss continued throughout 90 days of treatment with Univestin™ at 250 and 500 mg/day with statistical significance versus placebo (p=0.001 and 0.01 receptively). Celecoxib still did not show significance relative to the placebo. The decrease of BMI followed similar trends for the 250 mg/day dose of Univestin™ which was significant relative to the placebo after 30 days (p=0.008) as well as 90 days (p=0.001). The 500 mg/day dose of Univestin™ showed decreasing of BMI without statistical significance at 30 days of treatment. However, the decrease of BMI reached statistical significance 90 days of treatment (p=0.011). Again, after 90 days of treatment, the celecoxib treatment group showed no statistically significant changes in BMI versus placebo.

Figure 34:
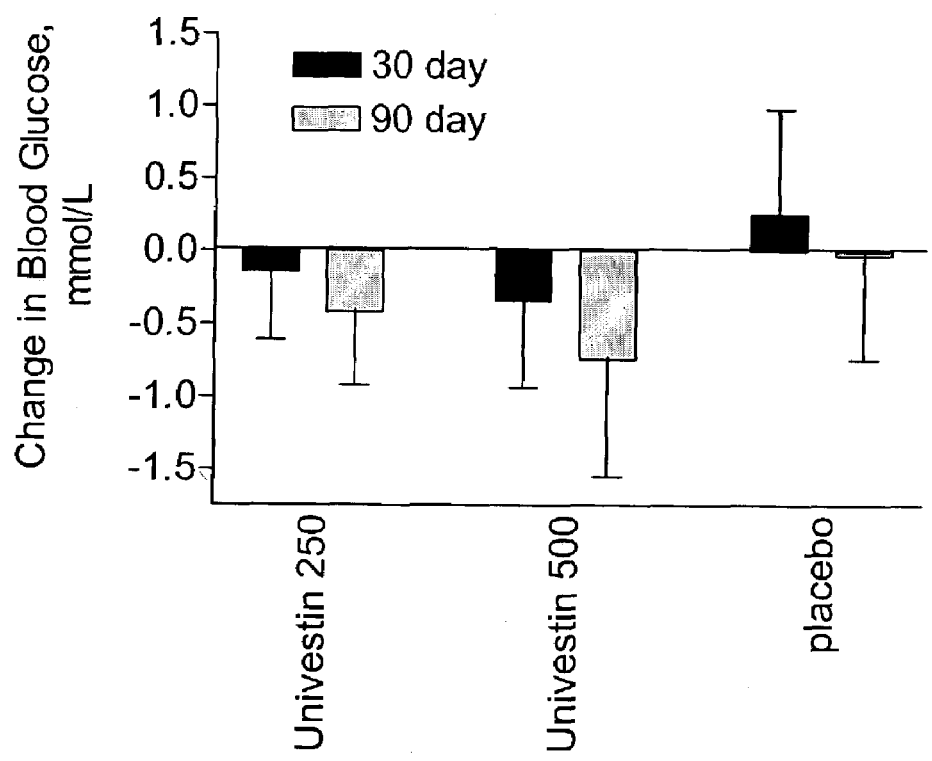
FIG. 34 shows the effect of Univestin™ at doses of 250 and 500 mg/day on lowering blood glucose compared to placebo.

Example 22 suggests that administration of Univestin™ may affect blood glucose levels as well as its effect on weight loss and BMI. Measurable differences in blood glucose levels are detected with 30 days of initiating treatment with Univestin™. At 90 days, both the 250 and 500 mg/day Univestin™ treated groups showed significant drops in blood glucose levels. The effect of celecoxib on blood glucose was less dramatic. The results are set forth in Table 15 and illustrated graphically in FIG. 34.

Once again multiple post-hoc comparisons for each treatment group pairs with the Analysis of Variance models were also performed for blood glucose as described in Example 22. Only the 500 mg/day dose of Univestin™ showed statistically relevant significance versus the placebo group (after 30 days, p=0.028; after 90 days, p=0.022). The 250 mg/day dose of Univestin™, however, showed clinically significant changes in blood glucose levels versus the placebo.

The applicant believes that U.S. application Ser. No. 10/104,477, filed Mar. 22, 2002, entitled "Isolation of a Dual COX-2 and 5-Lipoxygenase Inhibitor from Acacia," is the first report of a composition of matter isolated from the Acacia genus of plants that demonstrates dual specificity for COX-2 and 5-LO and that U.S. application Ser. No. 10/091, 362, filed Mar. 1, 2002, entitled "Identification of Free-B-ring Flavonoids as Potent COX-2 Inhibitors," is the first report of a correlation between Free-B-ring flavonoid structure and COX-2 inhibitory activity. These discoveries led to a novel blending of two classes of specific compounds—Free-B-ring flavonoids and flavans—to produce a composition of matter, referred to herein as Univestin™, which can be used for alleviating joint pain and stiffness, improving mobility and physical function and preventing and treating the pathological conditions of osteoarthritis, and rheumatoid arthritis.

While not limited by theory, the identified mechanism of action of this formulation is believed to be the direct inhibition of both the peroxidase activity of the COX-2 enzyme and the 5-LO enzyme activity, together with a decrease in the mRNA production of each of these enzymes. Univestin™ can also be utilized to prevent and treat COX-2 and 5-LO mediated diseases and conditions, including, but are not limited to osteoarthritis, rheumatoid arthritis, menstrual cramps, arteriosclerosis, heart attack, obesity, diabetes, syndrome X, Alzheimer's disease, respiratory allergic reaction, chronic venous insufficiency, hemorrhoids, Systemic Lupus Erythromatosis, psoriasis, chronic tension headache, migraine headaches, inflammatory bowel disease; topical infections caused by virus, bacteria, fungus, sunburn, thermal burns, contact dermatitis, melanoma and carcinoma. Finally, Univestin™ has been found in human clinical study that it can cause weight loss and reduce blood glucose level due to improvement of flexibility, mobility and increase physical activity.

The present invention is also directed toward therapeutic compositions comprising the therapeutic agents of the present invention. The therapeutic agents of the instant invention can be administered by any suitable means, including, for example, parenteral, topical, oral or local administration, such as intradermally, by injection, or by aerosol. The particular mode of administration will depend on the condition to be treated. It is contemplated that administration of the agents of the present invention may be via any bodily fluid, or any target or any tissue accessible through a body fluid. In the preferred embodiment of the invention, the agent is administered by injection. Such injection can be locally administered to any affected area. A therapeutic composition can be administered in a variety of unit dosage forms depending upon the method of administration. For example, unit dosage forms suitable for oral administration of an animal include powder, tablets, pills and capsules. Preferred delivery methods for a therapeutic composition of the present invention include intravenous administration and local administration by, for example, injection or topical administration. A therapeutic reagent of the present invention can be administered to any animal, preferably to mammals, and more preferably to humans.

For particular modes of delivery, a therapeutic composition of the present invention can be formulated so as to include other components such as a pharmaceutically acceptable excipient, an adjuvant, and/or a carrier. For example, compositions of the present invention can be formulated in an excipient that the animal to be treated can tolerate. Examples of such excipients, include but are not limited to cellulose, silicon dioxide, dextrates, sucrose, sodium starch glycolate, calcium phosphate, calcium sulfate, water, saline, Ringer's solution, dextrose solution, mannitol, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, Tris buffer, histidine, citrate, and glycine, or mixtures thereof, while examples of preservatives include thimerosal, m- or o-cresol, formalin and benzyl alcohol. Standard formulations can either be liquid injectables or solids, which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the composition can also include an adjuvant or a carrier. Adjuvants are typically substances that generally enhance the function of the formula in preventing and treating indications related to COX & LO pathways. Suitable adjuvants include, but are not limited to, Freund's adjuvant; other bacterial cell wall components; aluminum-based salts; calcium-based salts; silica; boron, histidine, glucosamine sulfates, Chondroitin sulfate, copper gluconate, polynucleotides; vitamin D, vitamin K, toxoids; shark and bovine cartilage; serum proteins; viral coat proteins; other bacterial-derived preparations; gamma interferon; block copolymer adjuvants, such as Hunter's Titermax adjuvant (Vaxcel.TM., Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

Once the therapeutic composition has been formulated, it may be stored in sterile vials as a solution, suspension, gel, emulsion, solid, or dehydrated or lyophilized powder; or directly capsulated and/or tableted with other inert carriers for oral administration. Such formulations may be stored either in a ready to use form or requiring reconstitution immediately prior to administration. The manner of administering formulations containing the compositions for systemic delivery may be via oral, subcutaneous, intramuscular, intravenous, intranasal or vaginal or rectal suppository.

The amount of the composition that will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curved derived from in vitro or animal model test systems. For example, an effective amount of the composition can readily be determined by administering graded doses of the composition and observing the desired effect.

The method of treatment according to this invention comprises administering internally or topically to a patient in need thereof a therapeutically effective amount of the composition comprised of a mixture of Free-B-ring flavonoids and flavans. The purity of the mixture includes, but is not limited to 0.01% to 100%, depending on the methodology used to obtain the compound(s). In a preferred embodiment, doses of the mixture of Free-B-ring flavonoids and flavans and pharmaceutical compositions containing the same are an efficacious, non-toxic quantity generally selected from the range of 0.01 to 200 mg/kg of body weight. Persons skilled in the art using routine clinical testing are able to determine optimum doses for the particular ailment being treated.

The following examples are provided for illustrative purposes only and are not intended to limit the scope of the invention.

EXAMPLES

Example 1

Preparation of Organic and Aqueous Extracts from *Acacia* and *Scutellaria* Plants Plant material from *Acacia catechu* (L) Willd. barks, *Scutellaria orthocalyx* roots, *Scutellaria baicalensis* roots or *Scutellaria lateriflora* whole plant was ground to a particle size of no larger than 2 mm. Dried ground plant material (60 g) was then transferred to an Erlenmeyer flask and methanol: dichloromethane (1:1) (600 mL) was added. The mixture was shaken for one hour, filtered and the biomass was extracted again with methanol:dichloromethane (1:1) (600 mL). The organic extracts were combined and evaporated under vacuum to provide the organic extract (see Table 1 below). After organic extraction, the biomass was air dried and extracted once with ultra pure water (600 mL). The aqueous solution was filtered and freeze-dried to provide the aqueous extract (see Table 1 below).

TABLE 1

Yield of Organic and Aqueous Extracts of Acacia and Scutellaria Species

| Plant Source | Amount | Organic Extract | Aqueous Extract |
|---|---|---|---|
| *Acacia catechu* barks | 60 g | 27.2 g | 10.8 g |
| *Scutellaria orthocalyx* roots | 60 g | 4.04 g | 8.95 g |
| *Scutellaria baicalensis* roots | 60 g | 9.18 g | 7.18 g |
| *Scutellaria lateriflora* (whole plant) | 60 g | 6.54 g | 4.08 g |

Example 2

Inhibition of COX-2 and COX-1 Peroxidase Activity by Plant Extracts from *Acacia catechu*, Various *Scutellaria* Species and Other Plants The bioassay directed screening process for the identification of specific COX-2 inhibitors was designed to assay the peroxidase activity of the enzyme as described below.

Peroxidase Assay. The assay to detect inhibitors of COX-2 was modified for a high throughput platform (Raz). Briefly, recombinant ovine COX-2 (Cayman) in peroxidase buffer (100 mM TBS, 5 mM EDTA, 1 μM Heme, 1 mg epinephrine, 0.094% phenol) was incubated with extract (1:500 dilution) for 15 minutes. Quantablu (Pierce) substrate was added and allowed to develop for 45 minutes at 25° C. Luminescence was then read using a Wallac Victor 2 plate reader. The results are presented in Table 2.

Table 2 sets forth the inhibition of enzyme by the organic and aqueous extracts obtained from five plant species, including the bark of *Acacia catechu*, roots of two *Scutellaria* species and extracts from three other plant species, which are comprised of structurally similar Free-B-ring flavonoids. Data is presented as the percent of peroxidase activity relative to the recombinant ovine COX-2 enzyme and substrate alone. The percent inhibition by the organic extract ranged from 30% to 90%.

TABLE 2

Inhibition of COX-2 Peroxidase activity by various species

| Plant Source | Inhibition of COX-2 by organic extract | Inhibition of COX-2 by aqueous extract |
|---|---|---|
| *Acacia catechu* (bark) | 75% | 30% |
| *Scutellaria orthocalyx* (root) | 55% | 77% |
| *Scutellaria baicalensis* (root) | 75% | 0% |
| *Desmodium sambuense* (whole plant) | 55% | 39% |
| *Eucaluptus globulus* (leaf) | 30% | 10% |
| *Murica nana* (leaf) | 90% | 0% |

Comparison of the relative inhibition of the COX-1 and COX-2 isoforms requires the generation of $IC_{50}$ values for each of these enzymes. The $IC_{50}$ is defined as the concentration at which 50% inhibition of enzyme activity in relation to the control is achieved by a particular inhibitor. In these experiments, $IC_{50}$ values were found to range from 6 to 50 μg/mL and 7 to 80 μg/mL for the COX-2 and COX-1 enzymes, respectively, as set forth in Table 3. Comparison of the $IC_{50}$ values of COX-2 and COX-1 demonstrates the specificity of the organic extracts from various plants for each of these enzymes. The organic extract of *Scutellaria lateriflora* for example, shows preferential inhibition of COX-2 over COX-1 with $IC_{50}$ values of 30 and 80 μg/mL, respectively. While some extracts demonstrate preferential inhibition of COX-2, others do not. Examination of the HTP fractions and purified compounds from these fractions is necessary to determine the true specificity of inhibition for these extracts and compounds.

TABLE 3

$IC_{50}$ Values of Organic Extracts for Human and Ovine COX-2 and COX-1

| Plant Source | $IC_{50}$ Human COX-2 (μg/ml) | $IC_{50}$ Ovine COX-2 (μg/ml) | $IC_{50}$ Ovine COX-1 (μg/ml) |
|---|---|---|---|
| *Acacia catechu* (bark) | 3 | 6.25 | 2.5 |
| *Scutellaria orthocalyx* (root) | Not done | 10 | 10 |
| *Scutellaria baicalensis* (root) | 30 | 20 | 20 |
| *Scutellaria lateriflora* (whole plant) | 20 | 30 | 80 |
| *Eucaluptus globulus* (leaf) | Not done | 50 | 50 |
| *Murica nana* (leaf) | 5 | 6 | 7 |

Example 3

HTP Fractionation of Active Extracts

Organic extract (400 mg) from active plant was loaded onto a prepacked flash column. (2 cm ID×8.2 cm, 10 g silica gel). The column was eluted using a Hitachi high throughput purification (HTP) system with a gradient mobile phase of (A) 50:50 EtOAc:hexane and (B) methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation. DMSO (1.5 mL) was used to dissolve the samples in each cell and a portion (100 μL was taken for the COX inhibition assay.

Aqueous extract (750 mg) from active plant was dissolved in water (5 mL), filtered through a 1 μm syringe filter and transferred to a 4 mL High Pressure Liquid Chromatography (HPLC) vial. The solution was then injected by an autosampler onto a prepacked reverse phase column (C-18, 15 μm particle size, 2.5 cm ID×10 cm with precolumn insert). The column was eluted using a Hitachi high throughput purification (HTP) system with a gradient mobile phase of (A) water and (B) methanol from 100% A to 100% B in 20 minutes, followed by 100% methanol for 5 minutes at a flow rate of 10 mL/min. The separation was monitored using a broadband wavelength UV detector and the fractions were collected in a 96-deep-well plate at 1.9 mL/well using a Gilson fraction collector. The sample plate was freeze-dried. Ultra pure water (1.5 mL) was used to dissolve samples in each cell and a portion (100 µL) was taken for the COX inhibition assay.

Example 4

Figure 2:
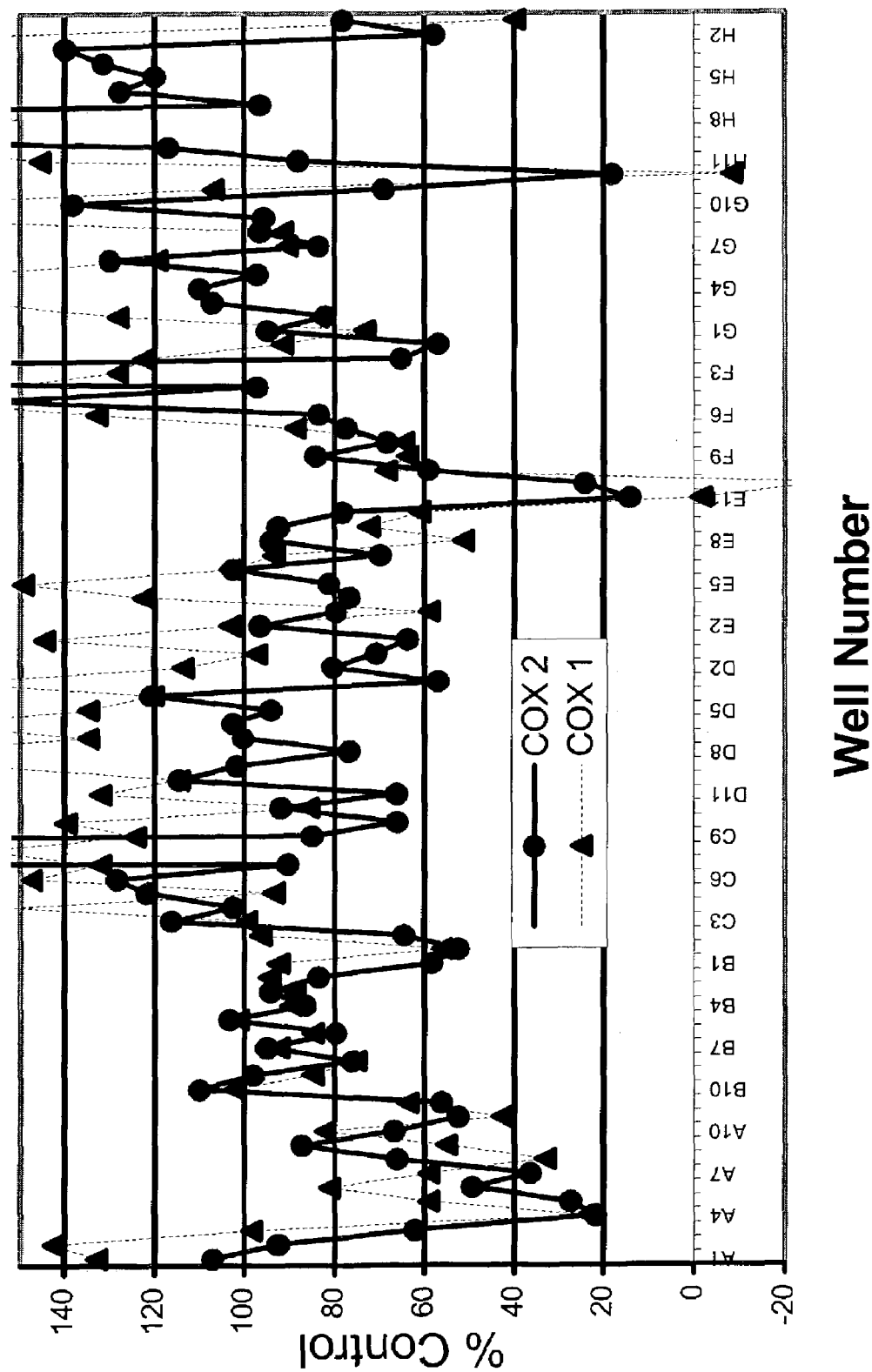
FIG. 2 depicts graphically the inhibition of COX-1 and COX-2 by HTP fractions from *Scutellaria baicalensis*. The extracts were prepared and fractionated as described in Examples 1 and 3. The extracts were examined for their inhibition of the peroxidase activity of recombinant ovine COX-1 (■) or ovine COX-2 (◆) as described in Example 2. The data is presented as percent of untreated control.

Inhibition of COX Peroxidase Activity by HTP Fractions from *Acacia* and *Scutellaria* Species Individual bioactive organic extracts were further characterized by examining each of the HTP fractions for the ability to inhibit the peroxidase activity of both COX-1 and COX-2 recombinant enzymes. The results are presented in FIGS. 1 and 2, which depict the inhibition of COX-2 and COX-1 activity by HTP fractions from organic extracts of the bark of *Acacia catechu* and the roots of *Scutellaria baicalensis* isolated as described in Examples 1 and 3 and assayed as described in Example 2. The profiles depicted in FIGS. 1 and 2 show multiple peaks of inhibition that indicate multiple active components in each extract. Several active peaks are very selective for COX-2. Other *Scutellaria* sp. including *Scutellaria orthocalyx* and *Scutellaria lateriflora* demonstrate a similar peak of inhibition (data not shown). However, both the COX-1 and COX-2 enzymes demonstrate multiple peaks of inhibition suggesting that there is more than one molecule contributing to the initial inhibition profiles.

Example 5

Isolation and Purification of the Active Free-B-ring Flavonoids from the Organic Extract of *Scutellaria*

The organic extract (5 g) from the roots of *Scutellaria orthocalyx*, isolated as described in Example 1, was loaded onto prepacked flash column (120 g silica, 40 µm particle size 32-60 µm, 25×4 cm) and eluted with a gradient mobile phase of (A) 50:50 EtOAc:hexane and (B) methanol from 100% A to 100% B in 60 minutes at a flow rate of 15 mL/min. The fractions were collected in test tubes at 10 mL/fraction. The solvent was evaporated under vacuum and the sample in each fraction was dissolved in 1 mL of DMSO and an aliquot of 20 µL was transferred to a 96 well shallow dish plate and tested for COX inhibitory activity. Based on the COX assay results, active fractions #31 to #39 were combined and evaporated. Analysis by HPLC/PDA and LC/MS showed a major compound with a retention times of 8.9 minutes and a MS peak at 272 m/e. The product was further purified on a C18 semi-preparation column (25 cm×1 cm), with a gradient mobile phase of (A) water and (B) methanol, over a period of 45 minutes at a flow rate of 5 mL/minute. Eighty-eight fractions were collected to yield 5.6 mg of light yellow solid. Purity was determined by HPLC/PDA and LC/MS, and comparison with standards and NMR data. $^1$H NMR: δ ppm. (DMSO-d6) 8.088 (2H, m, H-3',5'), 7.577 (3H, m, H-2',4',6'), 6.932 (1H, s, H-8), 6.613 (1H, s, H-3). MS: [M+1]+=271 m/e. The compound was identified as baicalein. The $IC_{50}$ of baicalein against the COX-2 enzyme was determined to be 10 µg/mL.

Figure 3:
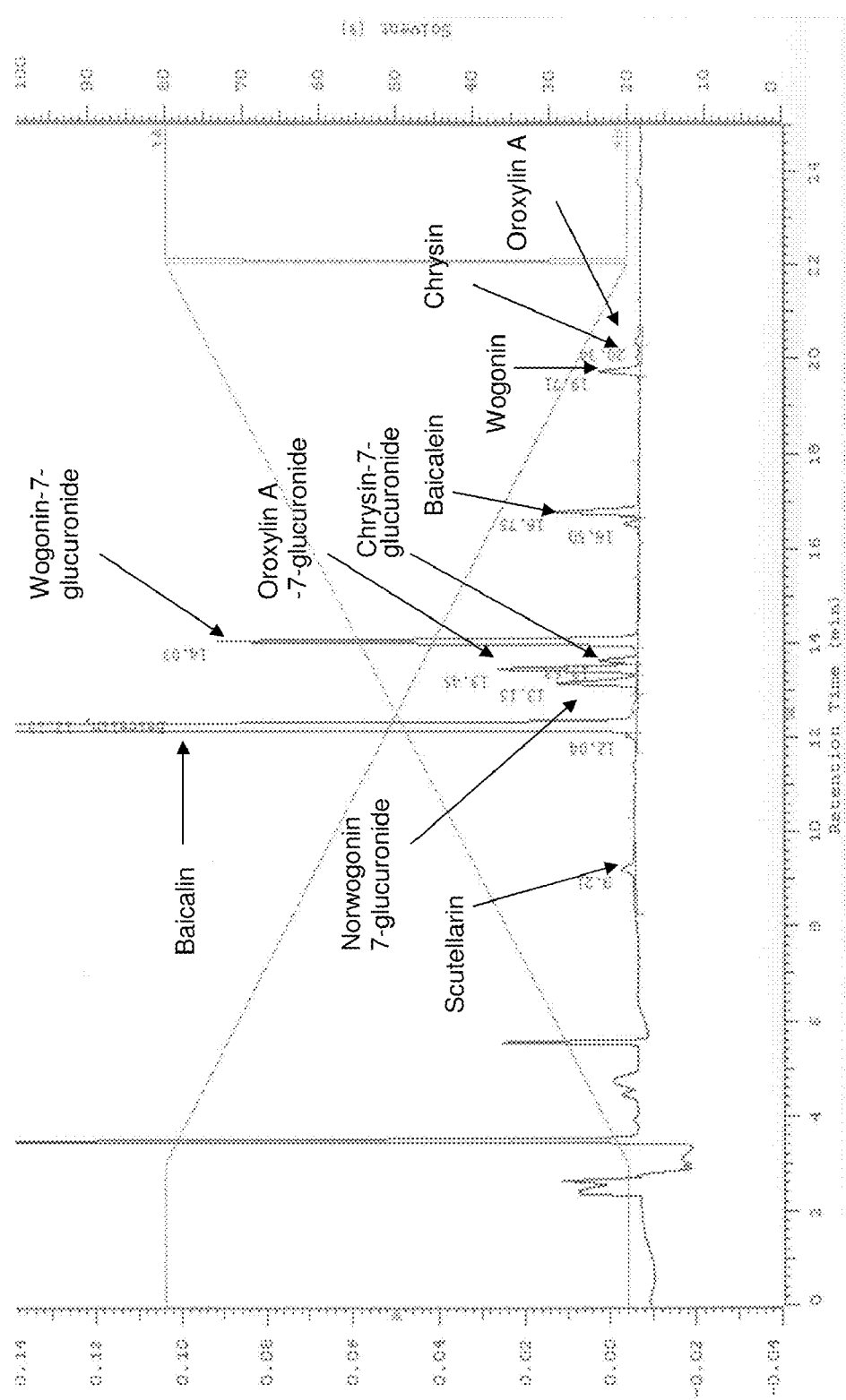
FIG. 3 depicts a HPLC chromatogram of a standardized extract isolated from the roots of *Scutellaria baicalensis* (lot #RM052302-01) having a Free-B-ring flavonoid content of 82.2%. Ten structures were elucidated using HPLC/PDA/MS as baicalin, wogonin-7-glucuronide, oroxylin A 7-glucuronide, baicalein, wogonin, chrysin-7-glucuronide, norwogonin-7-glucuronide, scutellarin, chrysin and oroxylin A.
Figure 4:
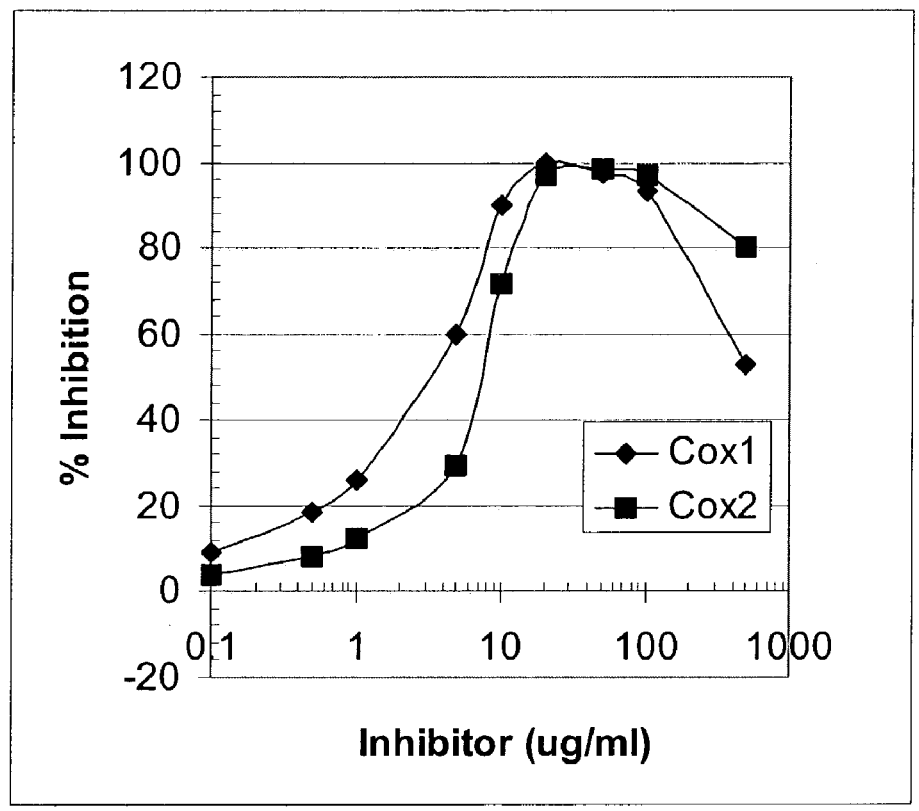
FIG. 4 depicts graphically a profile of the inhibition of COX-1 and COX-2 by the baicalein, which was isolated and purified from *Scutellaria baicalensis*. The compound was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was calculated as 0.18 μg/mL/unit of enzyme while the $IC_{50}$ for COX-2 was calculated as 0.28 μg/mL/unit.
Figure 5:
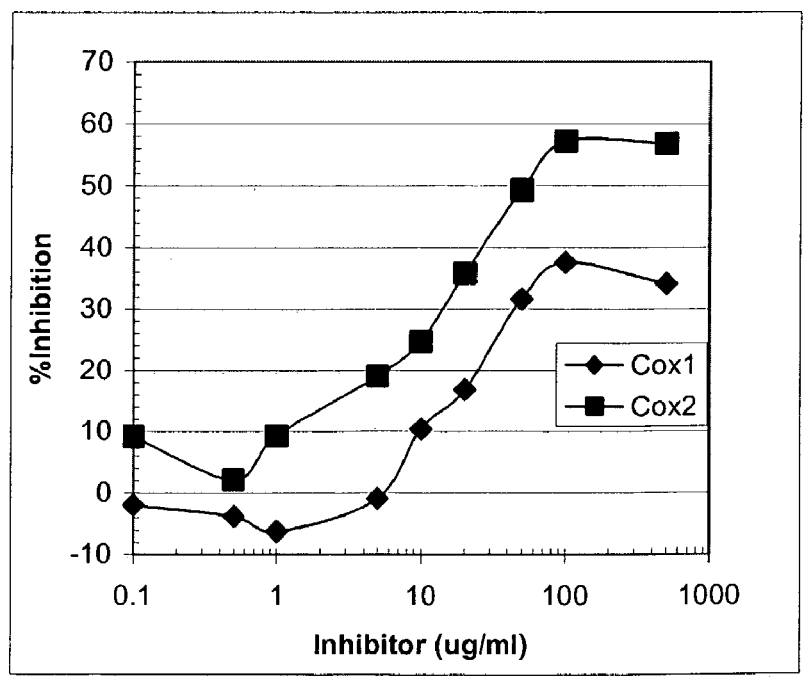
FIG. 5 depicts graphically a profile of the inhibition of COX-1 and COX-2 by the baicalin, which was isolated and purified from *Scutellaria baicalensis*. The compound was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was determined to be 0.44 μg/mL/unit of enzyme while that of COX-2 was determined to be 0.28 μg/mL/unit.
Figure 6:
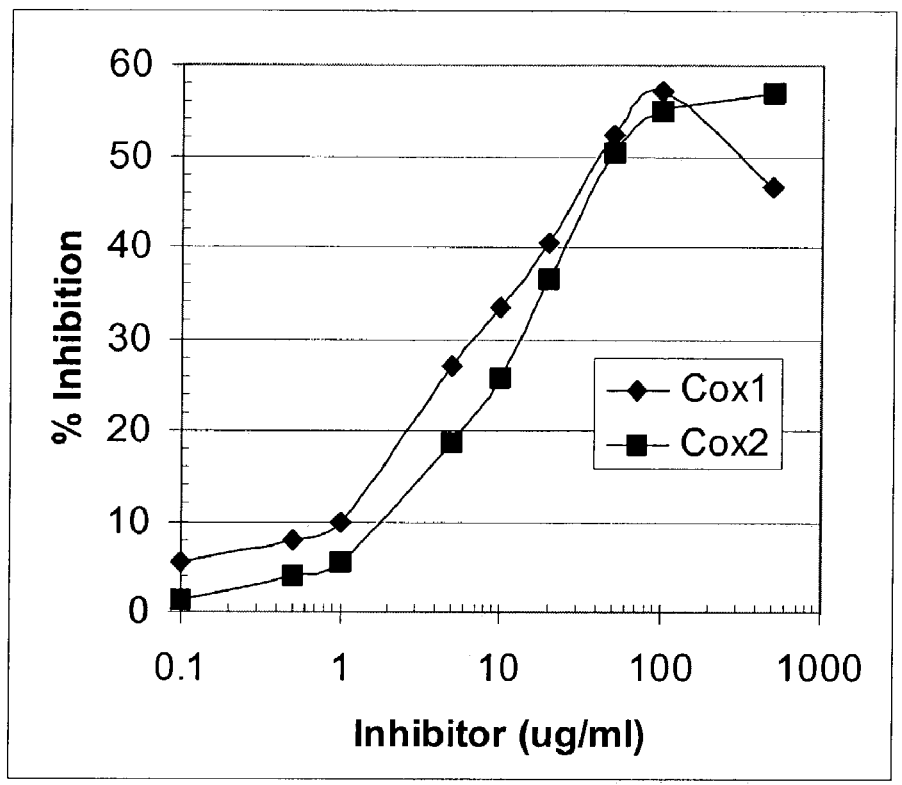
FIG. 6 depicts graphically a profile of the inhibition of COX-1 and COX-2 by a standardized Free-B-ring flavonoid extract (83% baicalin based on HPLC) isolated from *Scutellaria baicalensis*. The extract was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was calculated as 0.24 μg/mL/unit of enzyme while the $IC_{50}$ for COX-2 was calculated as 0.48 μg/mL/unit.

Using preparative C-18 column chromatography, other Free-B-ring flavonoids were isolated and identified using a standardized extract isolated from the roots of *Scutellaria baicalensis* (lot #RM052302-01), having a Free-B-ring flavonoid content of 82.2%. Eleven structures were elucidated using HPLC/PDA/MS as illustrated in FIG. 3. With reference to FIG. 3, the eleven compounds identified were baicalin, wogonin-7-glucuronide, oroxylin A 7-glucuronide, baicalein, wogonin, chrysin-7-glucuronide, 5-methyl-wogonin-7-glucuronide, scutellarin, norwogonin, chrysin and oroxylin A.

Example 6

COX Inhibition of Purified Free-B-Ring Flavonoids

Several Free-B-ring flavonoids have been obtained and tested at a concentration of 20 µg/mL for COX-2 inhibitory activity using the methods described in Example 2. The results are summarized in Table 4.

Measurement of the $IC_{50}$ of baicalein, baicalin and a standardized Free-B-ring flavonoid extract isolated from the roots of *Scutellaria baicalensis* was performed using the following method. A cleavable, peroxide chromophore was included in the assay to visualize the peroxidase activity of each enzyme in the presence of arachidonic acid as a cofactor. Typically, the assays were performed in a 96-well format. Each inhibitor, taken from a 10 mg/mL stock in 100% DMSO, was tested in triplicate at room temperature using the following range of concentrations: 0, 0.1, 1, 5, 10, 20, 50, 100, and 500 µg/mL. To each well, 150 µL of 100 mM Tris-HCl, pH 7.5 was added along with 10 µL of 22 µM Hematin diluted in tris buffer, 10 µL of inhibitor diluted in DMSO, and 25 units of either COX-1 or COX-2 enzyme. The components were mixed for 10 seconds on a rotating platform, after which 20 µL of 2 mM N,N,N'N'-Tetramethyl-p-phenylenediamine dihydrochloride (TMPD) and 20 µL of 1.1 mM AA was added to initiate the reaction. The plate was shaken for 10 seconds and then incubated for 5 minutes before reading the absorbance at 570 nm. The inhibitor concentration vs. percentage inhibition was plotted and the $IC_{50}$ determined by taking the half-maximal point along the isotherm and intersecting the concentration on the x-axis. The $IC_{50}$ was then normalized to the number of enzyme units in the assay. The dose response and $IC_{50}$ results for baicalein, baicalin and a standardized Free-B-ring flavonoid extract isolated from the roots of *Scutellaria baicalensis* are provided in FIGS. 4, 5 and 6, respectively.

TABLE 4

Inhibition of COX Enzymatic Activity by Purified Free-B-ring Flavonoids

| Free-B-ring Flavonoids | Inhibition of COX-1 | Inhibition of COX-2 |
| --- | --- | --- |
| Baicalein | 107% | 109% |
| 5,6-Dihydroxy-7-methoxyflavone | 75% | 59% |
| 7,8-Dihydroxyflavone | 74% | 63% |
| Baicalin | 95% | 97% |
| Wogonin | 16% | 12% |

Example 7

HPLC Quantification of Free-B-Ring Flavonoids in Active Extracts Isolated from *Scutellaria orthocalyx* (Roots), *Scutellaria baicalensis* (Roots) and *Oroxylum indicum* (Seeds)

The presence and quantity of Free-B-ring flavonoids in five active extracts isolated from three different plant species have been confirmed and are set forth in the Table 5. The Free-B-ring flavonoids were quantitatively analyzed by HPLC using a Luna C-18 column (250×4.5 mm, 5 µm) a using 1% phosphoric acid and acetonitrile gradient from 80% to 20% in 22 minutes. The Free-B-ring flavonoids were detected using a UV detector at 254 nm and identified based on retention time by comparison with Free-B-ring flavonoid standards.

TABLE 5

Free-B-ring Flavonoid Content in Active Plant Extracts

| Active Extracts | Weight of Extract | % Extractible from BioMass | Total amount of Free-B-ring Flavonoids | % Free-B-ring Flavonoids in Extract |
|---|---|---|---|---|
| *S. orthocalyx* (aqueous extract) | 8.95 g | 14.9% | 0.2 mg | 0.6% |
| *S. orthocalyx* (organic extract) | 3.43 g | 5.7% | 1.95 mg | 6.4% |
| *S. baicalensis* (aqueous extract) | 7.18 g | 12.0% | 0.03 mg | 0.07% |
| *S. baicalensis* (organic extract) | 9.18 g | 15.3% | 20.3 mg | 35.5% |
| *Oroxylum indicum* (organic extract) | 6.58 g | 11.0% | 0.4 mg | 2.2% |

Example 8

Isolation and Purification of Active Compounds from the Organic Extract of *Acacia catechu*

The organic extract (5 g) from the roots of *A. catechu*, isolated as described in Example 1, was loaded onto pre-packed flash column (120 g silica, 40 μm particle size 32-60 μm, 25 cm×4 cm) and eluted with a gradient mobile phase of (A) 50:50 EtOAc:hexane and (B) methanol from 100% A to 100% B in 60 minutes at a flow rate of 15 mL/min. The fractions were collected in test tubes at 10 mL/fraction. The solvent was evaporated under vacuum and the sample in each fraction was dissolved in DMSO (1 mL) and an aliquot of 20 μL was transferred to a 96 well shallow dish plate and tested for COX inhibitory activity. Based upon the COX assay results, active fractions #32 to #41 were combined and evaporated to yield 2.6 g of solid. Analysis by HPLC/PDA and LC/MS showed two major compounds with retention times of 15.8 and 16.1 minutes, respectively. The product was further purified on a C18 semi-preparatory column (25 cm×1 cm), loaded with 212.4 mg of product and eluted with a gradient mobile phase of (A) water and (B) acetonitrile (ACN), over a period of 60 minutes at a flow rate of 5 mL/minute. Eighty-eight fractions were collected and two active compounds were isolated. Compound 1 (11.5 mg) and Compound 2 (16.6 mg). Purity was determined by HPLC/PDA and LC/MS data by comparison with standards (catechin and epicatechin) and NMR data.

Compound 1. $^{13}$C NMR: δ ppm (DMSO-d6) 27.84 (C4), 66.27 (C3), 80.96 (C2), 93.78 (C9), 95.05 (C7), 99.00 (C5), 114.48 (C12), 115.01 (C15), 118.36 (C16), 130.55 (C11), 144.79 (C14), 155.31 (C6), 156.12 (C10), 156.41 (C8). $^1$H NMR: δ ppm. (DMSO-d6) 9.150 (1H, s, OH), 8.911 (1H,s, OH), 8.835 (1H, s, OH), 8.788 (1H, s, OH), 6.706 (1H, d, J=2 Hz, H2'), 6.670 (1H, d, J=8.0 Hz, H-6'), 6.578 (1H, dd, J=2, 8 Hz, H-5'), 5.873 (1H, d, J=2 Hz, H8), 5.670 (1H, d, J=2 Hz, H6), 4.839 (1H, d, J=4 Hz, OH), 4.461 (1H, d, J=7.3 Hz, H2), 3.798 (1H, m, H3), 2.625 (1H, m, H4b), 2.490 (1H, m, H4a). MS: [M+1]$^+$=291 m/e. This compound was identified as catechin.

Compound 2. $^{13}$C NMR: δ ppm. (DMSO-d6) 28.17 (C4), 64.87 (C3), 78.02 (C2), 94.03 (C9), 95.02 (C7), 98.44 (C5), 114.70 (C12), 114.85 (C15), 117.90 (C16), 130.56 (C11), 144.39 (C14), 155.72 (C6), 156.19 (C10), 156.48 (C8). $^1$H NMR: δ ppm. (DMSO-d6) 9.083 (1H, s, OH), 8.873 (1H,s, OH), 8.777 (1H, s, OH), 8.694 (1H, s, OH), 6.876 (1H, d, J=2 Hz, H2'), 6.646 (2H, s, H-5', 6'), 5.876 (1H, d, J=2 Hz, H8), 5.700 (1H, d, J=2 Hz, H6), 4.718 (1H, s, OH), 4.640 (1H, d, J=4.5 Hz, H2), 3.987 (1H, d, J=4.5 Hz, H3), 2.663 (1H, dd, J=4.6, 6.3 Hz, H4b), 2.463 (1H,dd, J=4.6, 6.3 Hz, H4a). MS: [M+1]$^+$=291 m/e. This compound was identified as epicatechin.

Figure 7:
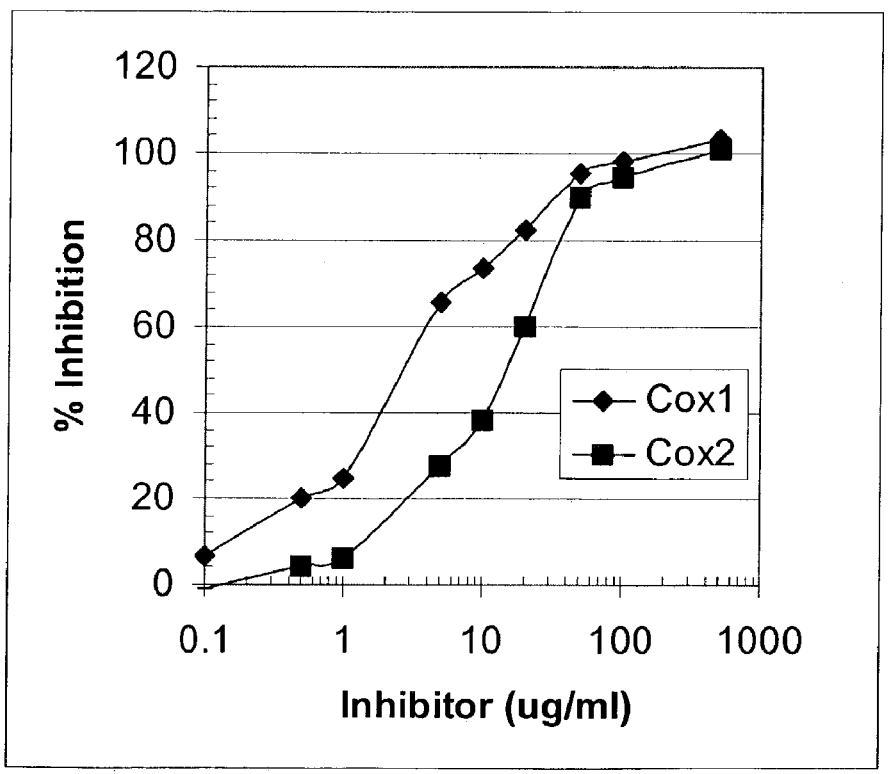
FIG. 7 depicts graphically a profile of the inhibition of COX-1 and COX-2 by catechin, which was isolated and purified from *Acacia catechu*. The compound was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was determined to be 0.11 μg/mL/unit of enzyme while the $IC_{50}$ for COX-2 was determined as 0.42 μg/mL/unit.
Figure 8:
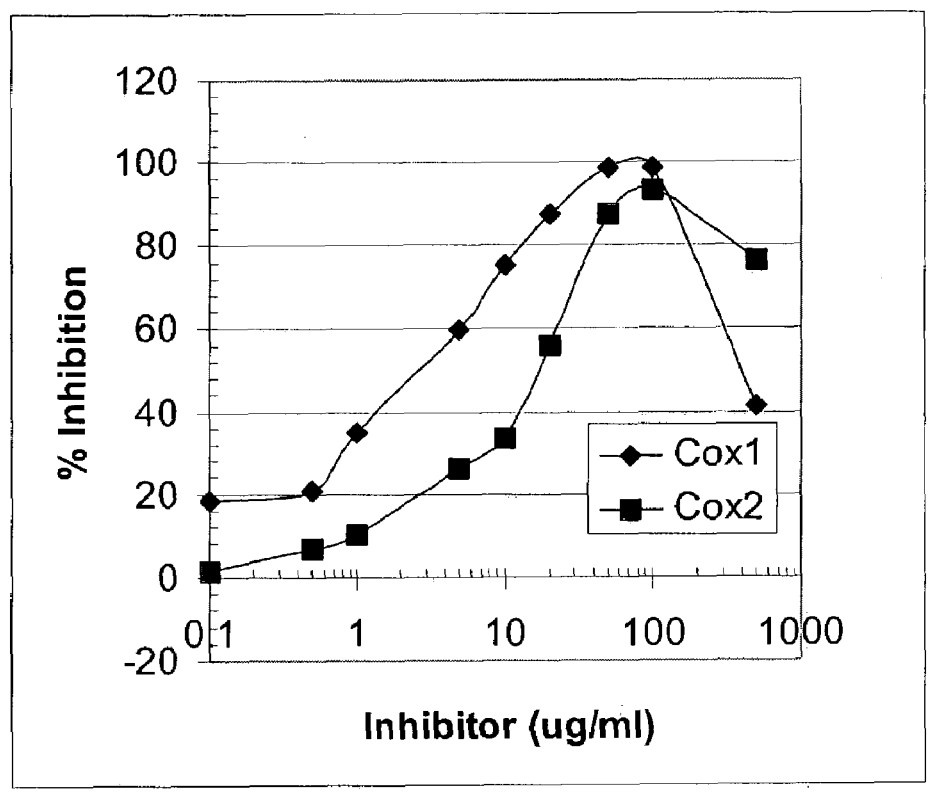
FIG. 8 depicts graphically a profile of the inhibition of COX-1 and COX-2 by a standardized flavan extract containing 50% total catechins isolated from *Acacia catechu*. The extract was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was calculated as 0.17 μg/mL/unit of enzyme while the $IC_{50}$ for COX-2 was determined to be 0.41 μg/mL/unit.

The dose response and IC$_{50}$ results for catechin and a standardized flavan extract isolated from the bark of *A. catechu* are illustrated in FIGS. 7 and 8, using the method described in Example 6. The IC$_{50}$ values of epicatechin against the COX-1 and COX-2 enzymes are 7 μg/mL and 20 μg/mL, respectively.

Example 9

HPLC Quantification of Active Extracts from *Acacia catechu*

Figure 9:
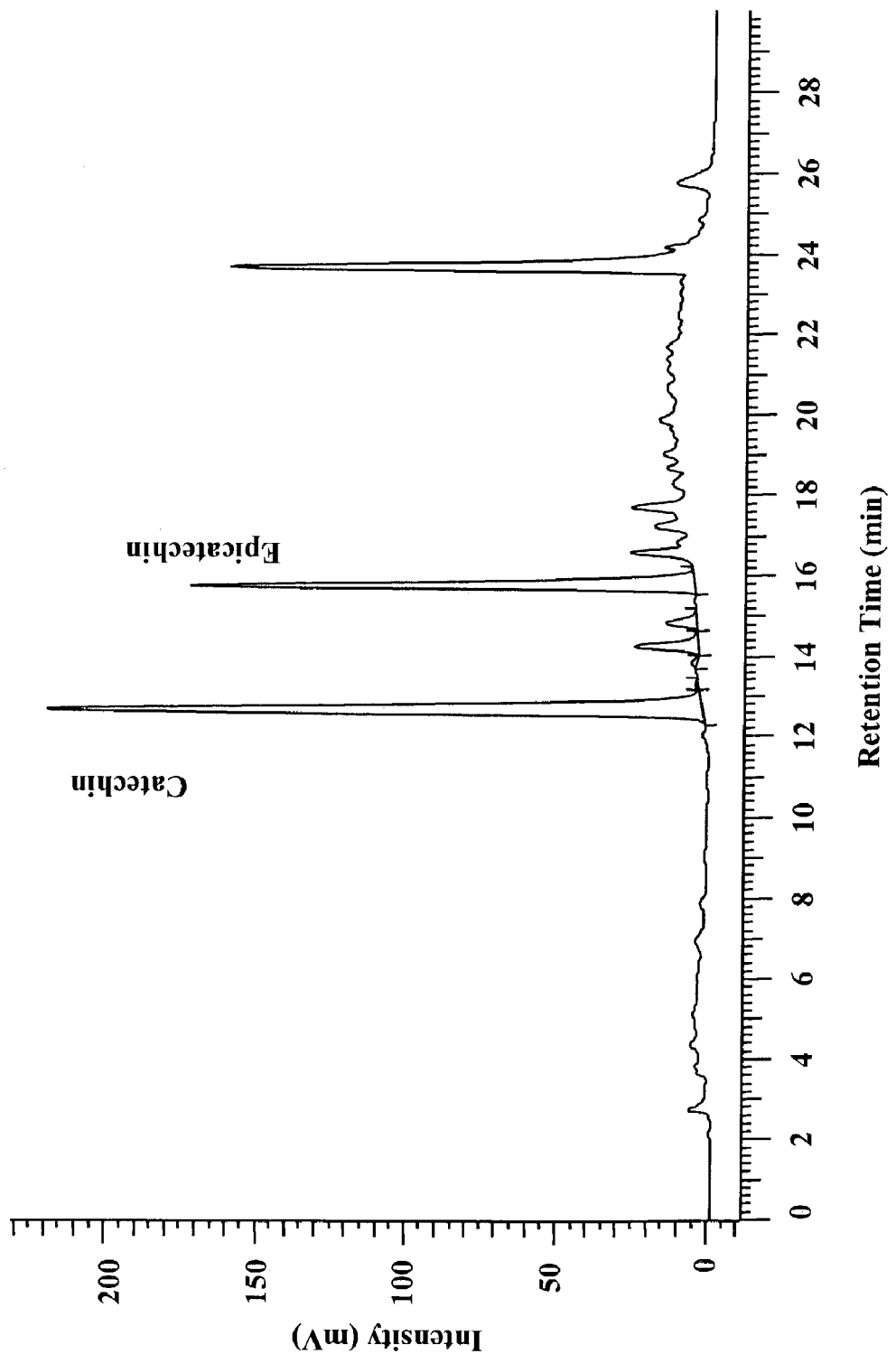
FIG. 9 depicts the HPLC chromatogram of the flavans extracted from *Acacia catechu* with 80% MeOH in water.
Figure 10:
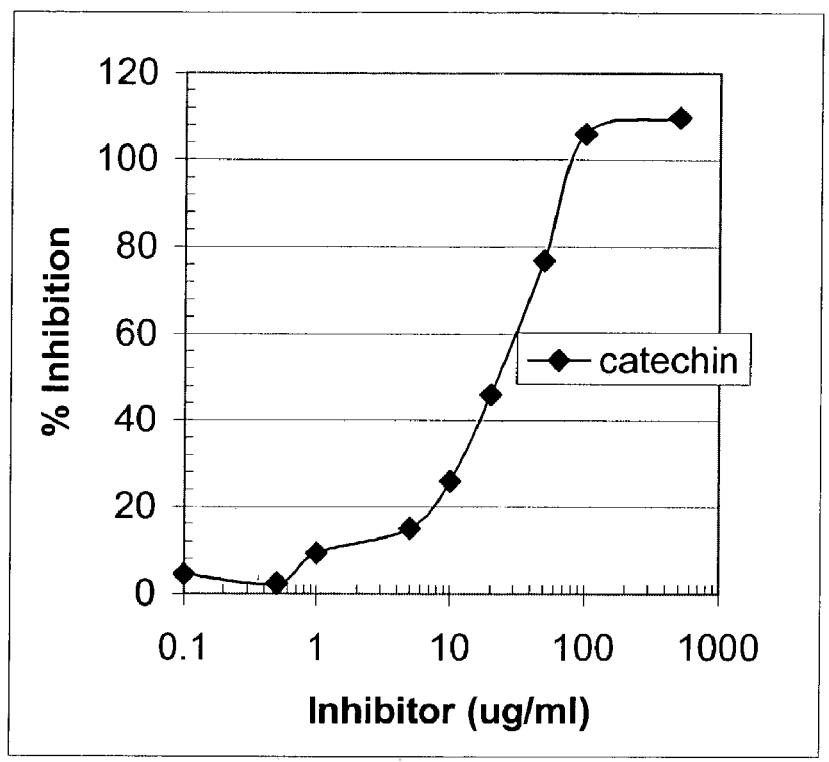
FIG. 10 depicts graphically a profile of the inhibition of 5-LO by the purified flavan catechin from *Acacia catechu*. The compound was examined for its inhibition of recombinant potato 5-lipoxygenase activity (◆). The data is presented as percent inhibition of assays without inhibitor vs. inhibitor concentration (μg/mL). The $IC_{50}$ for 5-LO was 1.38 μg/mL/unit of enzyme.

The flavan content in the organic and aqueous extracts isolated from *Acacia catechu* were quantified by HPLC using a PhotoDiode Array detector (HPLC/PDA) and a Luna C18 column (250 mm×4.6 mm). The flavans were eluted from the column using an acetonitrile gradient from 10% to 30% ACN over a period of 20 minutes, followed by 60% ACN for five minutes. The results are set forth in Table 6. A profile of the HPLC purification is shown in FIG. 9. The flavans were quantified based on retention time and PDA data using catechin and epicatechin as standards. The retention times for the two major flavans were 12.73 minutes and 15.76 minutes, respectively.

TABLE 6

Free-B-ring Flavonoid Content in Active Plant Extracts

| Active Extracts from bark of *A. catechu* | Weight of Extract | % Extractible from BioMass | % Flavans in Extract |
|---|---|---|---|
| Aqueous Extract | 10.8 g | 18.0% | 0.998% |
| Organic Extract | 27.2 g | 45.3% | 30.37% |

Example 10

In vitro Study of COX Inhibitory Activity of Organic Extracts from *Acacia catechu* and *Scutellaria* Species In vitro efficacy and COX-2 specificity of organic extracts isolated from *Acacia catechu* and various *Scutellaria* species were tested in cell-based systems for their ability to inhibit the generation of AA metabolites. Cell lines HOSC, which constitutively express COX-2 and THP-1, which express COX-1 were tested for their ability to generate PGE$_2$ in the presence of AA.

COX-2 Cell Based Assay. HOSC (ATCC#8304-CRL) cells were cultured to 80-90% confluence. The cells were trypsinized, washed and resuspended in 10 mL at 1×10$^6$ cells/mL in tissue culture media (MEM). The cell suspension (200 μL) was plated out in 96-well tissue culture plates and incubated for 2 hours at 37° C. and 5% CO$_2$. The media was then replaced with new HOSC media containing 1 ng/mL IL-1b and incubated overnight. The media was removed again and replaced with 190 mL HOSC media. Test compounds were then added in 10 µL of HOSC media and were incubated for 15 minutes at 37° C. Arachidonic acid in HOSC media (20 mL, 100 µM) was added and the mixture was incubated for 10 minutes on a shaker at room temperature. Supernatant (20 µL) was transferred to new plates containing 190 µL/well of 100 µM indomethacin in ELISA buffer. The supernatants were analyzed as described below by ELISA.

COX-1 Cell Based Assay. THP-1 cells were suspended to a volume of 30 mL ($5 \times 10^5$ cells/mL). TPA was added to a final concentration of 10 nM TPA and cultured for 48 hours to differentiate cells to macrophage (adherent). The cells were resuspended in HBSS (25 mL) and added to 96-well plates in 200 mL volumes at $5 \times 10^5$ cells/well. The test compounds in RPMI 1640 (10 µL) were then added and incubated for 15 minutes at 37° C. Arachidonic acid in RPMI (20 µL) was then added and the mixture was incubated for 10 minutes on a shaker at room temperature. Supernatant (20 µL) was added to ELISA buffer (190 µL) containing indomethacin (100 µM). The supernatants were then analyzed by ELISA, as described below.

COX-2 Whole Blood Assay. Peripheral blood from normal healthy donors was collected by venipuncture. Whole blood (500 µL) was incubated with test compounds and extracts for 15 minutes at 37° C. Lipopolysaccharide (LPS, from *E. coli* serotype 0111:B4) was added to a final concentration of 100 µg/mL and cultured overnight at 37° C. The blood was centrifuged (12,000×g) and the plasma was collected. Plasma (100 µL) was added to methanol (400 µL) to precipitate proteins. Supernatants were measured for $PGE_2$ production by ELISA. This procedure is a modification of the methods described by Brideau et al. (1996) Inflamm. Res. 45:68-74.

COX-1 Whole Blood Assay. Fresh blood was collected in tubes not containing anti-coagulants and immediately aliquoted into 500 µL aliquots in siliconized microcentrifuge tubes. Test samples were added, vortexed and allowed to clot for 1 hour at 37° C. The samples were then centrifuged (12,000×g) and the plasma was collected. The plasma (100 µL) was added to methanol (400 µL) to precipitate proteins. Supernatants were measured for $TXB_2$ production by ELISA. This procedure is a modification of the methods described by Brideau et al. (1996) Inflamm. Res. 45:68-74.

ELISA Assays. Immunolon-4 ELISA plates were coated with capture antibody 0.5-4 µg/mL in carbonate buffer (pH 9.2) overnight at 4° C. The plates were washed and incubated for 2 hours with blocking buffer (PBS+1% BSA) at room temperature. The plates were washed again and test sample (100 µL) was added and incubated for 1 hour at room temperature while shaking. Peroxidase conjugated secondary antibody was added in a 50 µL volume containing 0.5-4 mg/mL and incubated for 1 hour at room temperature while shaking. The plates were then washed three times and TMB substrate (100 µL) was added. The plates were allowed to develop for 30 minutes, after which the reaction was stopped by the addition of 1 M phosphoric acid (100 µL). The plates were then read at 450 nm using a Wallac Victor 2 plate reader.

Cytotoxicity. Cellular cytotoxicity was assessed using a colorimetric kit (Oxford Biochemical Research) that measures the release of lactate dehydrogenase in damaged cells. Assays were completed according to manufacturer's directions. Both purified flavans and standardized extract from *Acacia catechu* were tested. No cytotoxicity was observed for any of the tested compounds.

The results of the assays are set forth in Table 7. The data are presented as $IC_{50}$ values for direct comparison. With reference to Table 5, $IC_{50}$ values are generally lower for COX-1 than COX-2. Additionally, whole blood was also measured for the differential inhibition of $PGE_2$ generation (a measure of COX-2 in this system) or thromboxane B2 ($TXB_2$) (a measure of COX-1 activation). Referring to Table 7, these studies clearly demonstrate specificity for COX-2 inhibition within the assays based on whole blood cells. However, studies using the THP-1 and HOSC-based model system actually showed greater selectivity for COX-1. Possible reasons for this discrepancy are the fundamental differences between immortalized cell lines that constitutively express each of the enzymes and primary cells derived from whole blood that are induced to express COX enzymes. Primary cells are a more relevant model to study inflammation in vivo. Additionally, the compounds used to identify COX-1 vs. COX-2 activity vary in each of these systems and consequently are not directly comparable.

TABLE 7

Inhibition of COX Activity in Cell Systems by Organic Extracts

| Plant Source of the organic extracts | Cell Line Based Assay | | Whole Blood Assay | |
|---|---|---|---|---|
| | $IC_{50}$ COX-2 | $IC_{50}$ COX-1 | $IC_{50}$ COX-2 | $IC_{50}$ COX-1 |
| *A. catechu* (bark) | 78 µg/mL | 22 µg/mL | 40 µg/mL | >50 µg/mL |
| *S. orthocalyx* (root) | 50 µg/mL | 18 µg/mL | 10 µg/mL | >50 µg/mL |
| *S. baicalensis* (root) | 82 µg/mL | 40 µg/mL | 20 µg/mL | 8 µg/mL |
| *S. lateriflora* (whole plant) | 60 µg/mL | 30 µg/mL | 8 µg/mL | 20 µg/mL |

Example 11

Inhibition of 5-Lipoxygenase by the Catechin from *Acacia catechu*

As noted above, one of the most important pathways involved in the inflammatory response is produced by non-heme, iron-containing lipoxygenases (5-LO, 12-LO, and 15-LO), which catalyze the addition of molecular oxygen onto fatty acids such as AA (AA) to produce the hydroperoxides 5-, 12- and 15-HPETE, which are then converted to leukotrienes. There were early indications that the flavan extract from *A. catechu* may provide some degree of 5-LO inhibition, thereby preventing the formation of 5-HPETE. A Lipoxygenase Inhibitor Screening Assay Kit (Cayman Chemical, Inc., Cat#760700) was used to assess whether the purified flavan catechin from *Acacia catechu* directly inhibited 5-LO in vitro. The 15-LO from soybeans normally used in the kit was replaced with potato 5-LO, after a buffer change from phosphate to a tris-based buffer using microfiltration was performed. This assay detects the formation of hydroperoxides through an oxygen sensing chromagen. Briefly, the assay was performed in triplicate by adding 90 µL of 0.17 units/µL potato 5-LO, 20 µL of 1.1 mM AA, 100 µL of oxygen-sensing chromagen, and 10 µL of purified flavan inhibitor to final concentrations ranging from 0 to 500 µg/mL. The $IC_{50}$ for 5-LO inhibition from catechin was determined to be 1.38 µg/mL/unit of enzyme.

Example 12

Preparation of a Standardized Extract from *Acacia catechu*

*Acacia catechu* (500 mg of ground bark) was extracted with the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The extracts were concentrated and dried under low vacuum. The identification of the chemical components in each extract was achieved by HPLC using a PhotoDiode Array detector (HPLC/PDA) and a 250 mm×4.6 mm C18 column. The chemical components were quantified based on retention time and PDA data using catechin and epicatechin as standards. The results are set forth in Table 8 and FIG. 9. As shown in Table 6, the flavan extract generated from solvent extraction with 80% methanol/water provided the best concentration of flavan components.

TABLE 8

Solvents for Generating Standardized Flavan Extracts from *Acacia catechu*

| Extraction Solvent | Weight of Extract | % Extractible from BioMass | Total amount of Catechins | % Catechins in Extract |
|---|---|---|---|---|
| 100% water | 292.8 mg | 58.56% | 13 mg | 12.02% |
| water:methanol (80:20) | 282.9 mg | 56.58% | 13 mg | 11.19% |
| water:methanol (60:40) | 287.6 mg | 57.52% | 15 mg | 13.54% |
| water:methanol (40:60) | 264.8 mg | 52.96% | 19 mg | 13.70% |
| water:methanol (20:80) | 222.8 mg | 44.56% | 15 mg | 14.83% |
| 100% methanol | 215.0 mg | 43.00% | 15 mg | 12.73% |
| methanol:THF (80:20) | 264.4 mg | 52.88% | 11 mg | 8.81% |
| methanol:THF (60:40) | 259.9 mg | 51.98% | 15 mg | 9.05% |

Example 13

Preparation of Standardized Free-B-ring Flavonoid Extracts from Various *Scutellaria* Species

*Scutellaria orthocalyx* (500 mg of ground root) was extracted twice with 25 mL of the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The extracts were combined, concentrated and dried under low vacuum. Identification of chemical components in each extract was performed by HPLC using a PhotoDiode Array detector (HPLC/PDA) and a 250 mm×4.6 mm C18 column. The chemical components were quantified based on retention time and PDA data using baicalein, baicalin, scutellarein, and wogonin as standards. The results are set forth in Table 9.

TABLE 9

Quantification of Free-B-ring Flavonoids Extracted from *Scutellaria orthocalyx*

| Extraction Solvent | Weight of Extract | % Extractible from BioMass | Total amount of Flavonoids | % Flavonoids in Extract |
|---|---|---|---|---|
| 100% water | 96 mg | 19.2% | 0.02 mg | 0.20% |
| Water:methanol (80:20) | 138.3 mg | 27.7% | 0.38 mg | 0.38% |
| Water:methanol (60:40) | 169.5 mg | 33.9% | 0.78 mg | 8.39% |

TABLE 9-continued

Quantification of Free-B-ring Flavonoids Extracted from *Scutellaria orthocalyx*

| Extraction Solvent | Weight of Extract | % Extractible from BioMass | Total amount of Flavonoids | % Flavonoids in Extract |
|---|---|---|---|---|
| Water:methanol (40:60) | 142.2 mg | 28.4% | 1.14 mg | 11.26% |
| Water:methanol (20:80) | 104.5 mg | 20.9% | 0.94 mg | 7.99% |
| 100% methanol | 57.5 mg | 11.5% | 0.99 mg | 10.42% |
| methanol:THF (80:20) | 59.6 mg | 11.9% | 0.89 mg | 8.76% |
| methanol:THF (60:40) | 58.8 mg | 11.8% | 1.10 mg | 10.71% |

*Scutellaria baicalensis* (1000 mg of ground root) was extracted twice using 50 mL of a mixture of methanol and water as follows: (1) 100% water, (2) 70:30 water:methanol, (3) 50:50 water:methanol, (4) 30:70 water:methanol, (5) 100% methanol. The extracts were combined, concentrated and dried under low vacuum. Identification of the chemical components was performed by HPLC using a PhotoDiode Array detector (HPLC/PDA), and a 250 mm×4.6 mm C18 column. The chemical components in each extract were quantified based on retention time and PDA data using baicalein, baicalin, scutellarein, and wogonin standards. The results are set forth in Table 10.

TABLE 10

Quantification of Free-B-ring Flavonoids Extracted from *Scutellaria baicalensis*

| Extraction Solvent | Weight of Extract | % Extractible from BioMass | Total amount of Flavonoids | % Flavonoids in Extract |
|---|---|---|---|---|
| 100% water | 277.5 mg | 27.8% | 1 mg | 0.09% |
| Water:methanol (70:30) | 338.6 mg | 33.9% | 1.19 mg | 11.48% |
| Water:methanol (50:50) | 304.3 mg | 30.4% | 1.99 mg | 18.93% |
| Water:methanol (30:70) | 293.9 mg | 29.4% | 2.29 mg | 19.61% |
| 100% methanol | 204.2 mg | 20.4% | 2.73 mg | 24.51% |

Example 14

Preparation of a Formulation with a Standardized Free-B-ring Flavonoid Extract from the Roots of *Scutellaria baicalensis* and a Standardized Flavan Extract from the Bark of *Acacia* catechu A novel composition of matter, referred to herein as Univestin™ was formulated using two standardized extracts isolated from *Acacia* and *Scutellaria*, respectively, together with one or more excipients. A general example for preparing such a composition is set forth below. The *Acacia* extract used in this example contained >60% total flavans, as catechin and epicatechin, and the *Scutellaria* extract contained >70% Free-B-ring flavonoids, which was primarily baicalin. The *Scutellaria* extract contained other minor amounts of Free-B-ring flavonoids as set forth in Table 11. One or more exipients is added to the composition of matter. The ratio of flavan and Free-B-ring flavonoids can be adjusted based on the indications and the specific requirements with respect to inhibition of COX-2 vs. 5-LO and potency requirements of the product. The quantity of the excipients can be adjusted based on the actual active content of each ingredient. A blending table for each individual batch of product must be generated based on the product specification and QC results for individual batch of ingredients. Additional amounts of active ingredients in the range of 2-5% are recommended to meet the product specification. Table 11 illustrates a blending table that was generated for one batch of Univestin™ (Lot#G1702-COX-2).

Scutellaria baicalensis root extract (38.5 kg) (lot #RM052302-01) having a Free-B-ring flavonoid content of 82.2% (baicalin); Acacia catechu bark extract (6.9 kg) (lot #RM052902-01) with total flavan content of 80.4%; and excipient (5.0 kg of Candex) were combined to provide a Univestin™ formulation (50.4 kg) having a blending ratio of 85:15. Table 9 provides the quantification of the active Free-B-ring flavonoids and flavans of this specific batch of Univestin™ (Lot#G1702-COX-2), determined using the methods provided in Examples 7 and 9.

TABLE 11

Free-B-ring Flavonoid and Flavan Content of Univestin ™ Formulation

| Active Components | % Content |
| --- | --- |
| 1. Flavonoids | |
| a. Baicalin | 62.5% |
| b. Minor Flavonoids | |
| i. Wogonin-7-glucuronide | 6.7% |
| ii. Oroxylin A 7-glucuronide | 2.0% |
| iii. Baicalein | 1.5% |
| iv. Wogonin | 1.1% |
| v. Chrysin-7-glucuronide | 0.8% |
| vi. 5-Methyl-wogonin-7-glucuronide | 0.5% |
| vii. Scutellarin | 0.3% |
| viii. Norwogonin | 0.3% |
| ix. Chrysin | <0.2% |
| x. Oroxylin A | <0.2% |
| c. Total Free-B-ring Flavonoids | 75.7% |
| 2. Flavans | |
| a. Catechin | 9.9% |
| b. Epicatechin | 0.4% |
| c. Subtotal Flavans | 10.3% |
| 3. Total Active Ingredients | 86% |

With reference to Table 9, this specific batch of Univestin™ contains 86% total active ingredients, including 75.7% Free-B-ring flavonoids and 10.3% flavans. Two different dosage levels of final product in capsule form were produced from this batch of Univestin™ (50.0 kg): 125 mg per dose (60 capsules) and 250 mg per dose (60 capsules). The final product was evaluated in a human clinical trial as described in Example 15.

Using the same approach, two other batches of Univestin™ were prepared using a combination of a standardized Free-B-ring flavonoid extract from Scutellaria baicalensis roots and a standardized flavan extract from Acacia catechu bark having a blending ratio of 50:50 and 20:80, respectively.

Example 15

Measurements of Dose Response and $IC_{50}$ Values of COX Enzyme Inhibitions from Three Formulations of Univestin™

Figure 11:
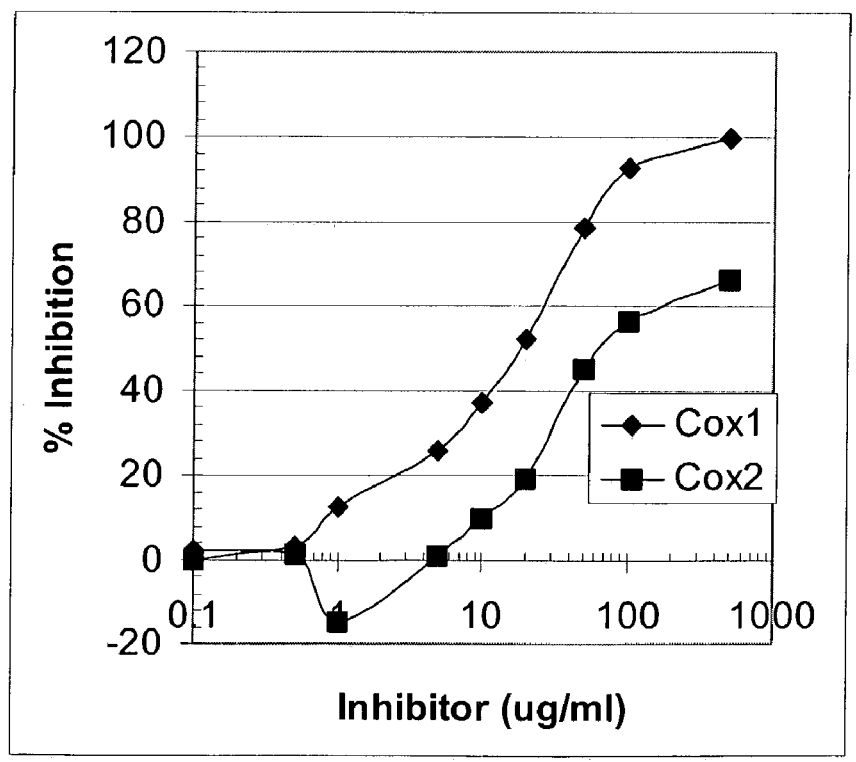
FIG. 11 depicts graphically a profile of the inhibition of COX-1 and COX-2 by the Univestin™ composition produced through combination of the extracts of Free-B-ring flavonoids and flavans in a ratio of 85:15 as described in Example 14. Univestin™ was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was 0.76 μg/mL/unit of enzyme while the $IC_{50}$ for COX-2 was 0.80 μg/mL/unit.
Figure 12:
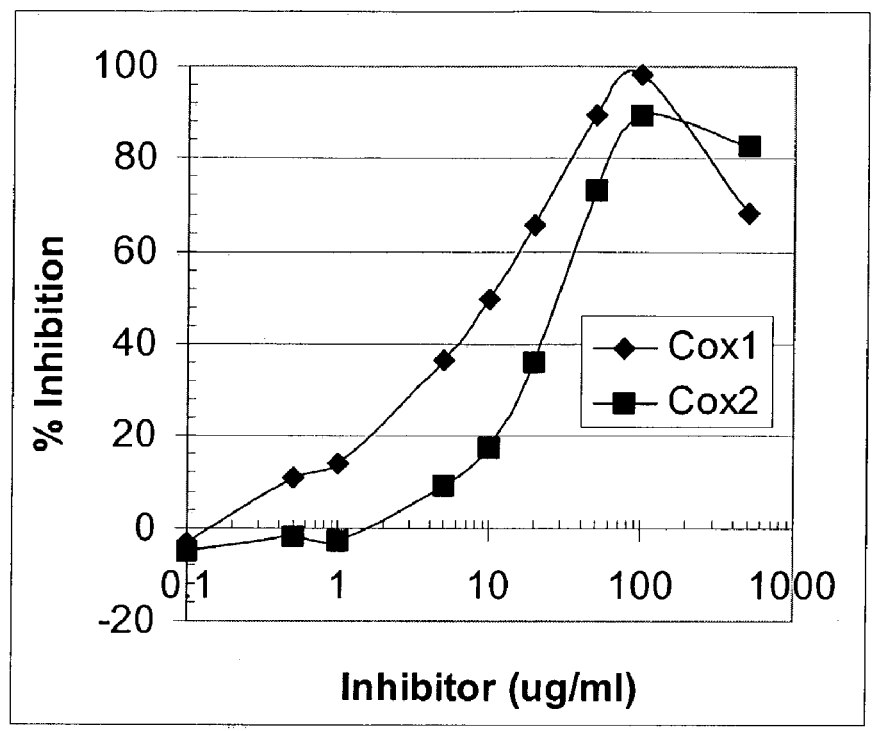
FIG. 12 depicts graphically a profile of the inhibition of COX-1 and COX-2 by the Univestin™ composition produced through combination of Free-B-ring flavonoids and flavans extracts in a ratio of 50:50 as described in Example 14. Univestin™ was examined for its inhibition of the peroxidase activity of recombinant ovine COX-1 (◆) and ovine COX-2 (■). The data is presented as percent inhibition vs. inhibitor concentration (μg/mL). The $IC_{50}$ for COX-1 was 0.38 μg/mL/unit of enzyme while the $IC_{50}$ for COX-2 was 0.84 μg/mL/unit.
Figure 13:
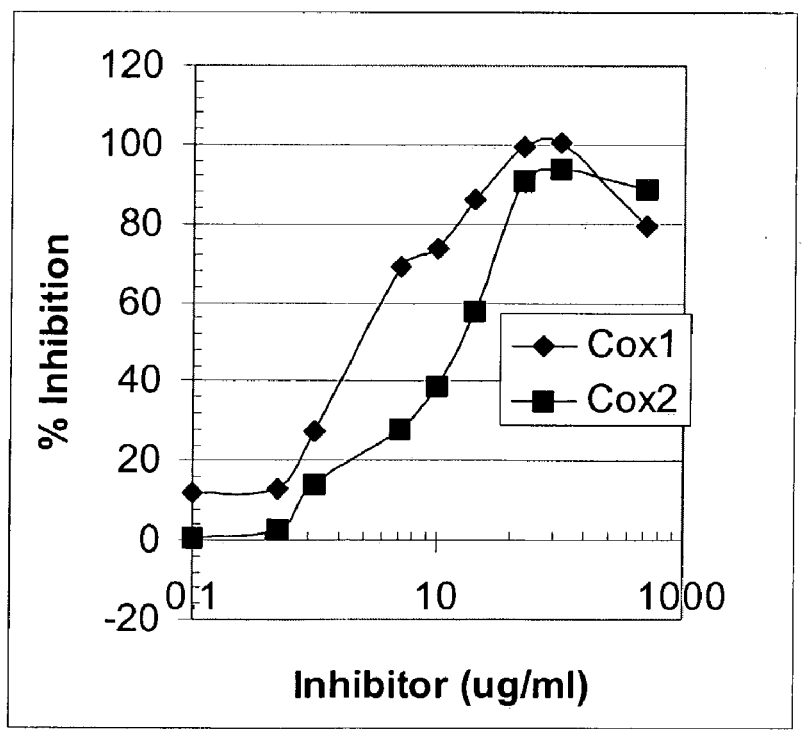
FIG. 13 depicts graphically a profile of the inhibition of COX-1 and COX-2 by the Univestin™ composition produced through combination extracts of Free-B-ring flavonoids and flavans in a ratio of 20:80 as described in Example 14. Univestin™ was examined for its inhibition of the peroxidase activity of recombinant ovine COX-1 (◆) and ovine COX-2 (■). The data is presented as percent inhibition of assays without inhibitor vs. inhibitor concentration (μg/mL). The $IC_{50}$ for COX-1 was 0.18 μg/mL/unit of enzyme while the $IC_{50}$ for COX-2 was 0.41 μg/mL/unit.

The three different formulations of Univestin™ are produced as provided in Example 14 were tested for COX-1 and COX-2 inhibitory activity as described in Example 6. All three formulation show significant dose response inhibition of COX enzyme activities as illustrated in FIGS. 11,12 and 13).

Example 16

Measurements of Dose Response and $IC_{50}$ Values of LO Enzyme Inhibition from a Formulation of Univestin™

A Univestin™ sample was produced as outlined in Example 14, using a combination of a standardized Free-B-ring flavonoid extract from Scutellaria baicalensis roots and a standardized flavan extract from Acacia catechu bark with a blending ratio of 80:20. The sample was titrated in tissue culture media containing THP-1 or HT-29 cells; monocyte cell lines that express COX-1, COX-2 and 5-LO. A competitive ELISA for $LTB_4$ ($LTB_4$; Neogen, Inc., Cat#406110) was used to assess the effect of Univestin™ on newly synthesized levels of $LTB_4$ present in each cell line as a measure of Univestin™'s inhibitory effect on the 5-LO pathway. The assay was performed in duplicate by adding 160,000 to 180,000 cells per well in 6-well plates. Univestin™ was added to the THP-1 cultures at 3, 10, 30 and 100 µg/mL and incubated overnight (~12-15 hrs) at 37° C. with 5% $CO_2$ in a humidified environment. The results are set forth in FIG. 14, which shows that the production of newly LPS-induced $LTB_4$ was almost completely inhibited by the addition of Univestin™ to the THP-1 cultures between 3 and 10 µg/mL.

Figure 15:
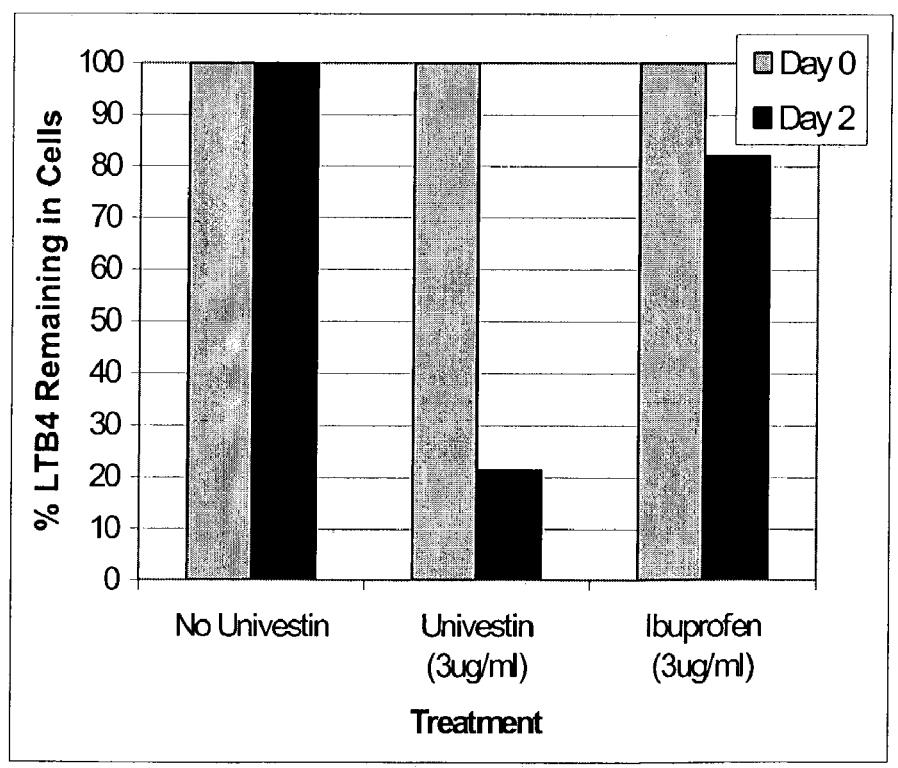
FIG. 15 compares the $LTB_4$ levels as determined by ELISA that remain in HT-29 cells after treatment with 3 μg/mL Univestin™ in non-induced cells to treatment with 3 μg/mL ibuprofen as described in Example 16.

Univestin™ and ibuprofen, another known 5-LO inhibitor, were added to the HT-29 cells at 3 µg/mL and incubated 48 hrs at 37° C. with 5% $CO_2$ in a humidified environment. Each treated cell line was then harvested by centrifugation and disrupted by gentle dounce homogenization lysis in physiological buffers. As shown in FIG. 15, Univestin™ inhibited generation of 80% of the newly synthesized $LTB_4$ in HT-29 cells. Ibuprofen only showed a 20% reduction in the amount of $LTB_4$ over the same time period.

Example 17

Differential Inhibition of cox-2 but not cox-1 Gene Expression by Univestin™ vs. Other NSAIDs To evaluate whether Univestin™ is operating on the genomic level, isolated human, peripheral blood monocytes (PBMCs) were stimulated with lipopolysaccharide (LPS), treated with Univestin™ as illustrated in Example 14, celecoxib, ibuprofen or acetaminophen, and the total RNA produced was then harvested and evaluated by semi-quantitative RT-qPCR. Specifically, the assay was constructed by adding 130,000 cells per well in 6-well plates. The cells were then stimulated with 10 ng/mL LPS and co-incubated with Univestin™ at 1, 3, 10, 30 and 100 μg/mL and celecoxib, ibuprofen and acetaminophen at 3 μg/mL for 18 hours at 37° C. with 5% $CO_2$ in a humidified environment. Each cell-treatment condition was then harvested by centrifugation and total RNA produced was isolated using TRIzol® reagent (Invitrogen™ Life Technologies, Cat#15596-026) and the recommended TRIzol® reagent protocol. Total RNA was reverse transcribed using Moloney Murine Leukemia Virus reverse transcriptase (M-MLV RT; Promega Corp., Cat#M1701) using random hexamers (Promega Corp., Cat#C1181). qPCR experiments were performed on an ABI Prism®7700 Sequence Detection System using pre-developed validated Assays-on-Demand products (AOD from Applied Biosystems, Inc., Cat#4331182) for 18S rRNA internal standard and gene specific assays. Gene specific expression values were standardized to their respective 18S rRNA gene expression values (internal control) and then the no-LPS no-drug treatment condition normalized to 100. Treatment conditions are relative to this null condition.

Univestin™ decreased normalized gene expression of cox-2 by over 100-fold, while cox-1 normalized gene expression showed little variation. When PBMCs were treated with 3 μg/mL of Univestin™, celecoxib, ibuprofen or acetaminophen, only Univestin™ did not increase gene expression of cox-2. It is believed that this is the first report of changes in gene expression levels of eicosinoids, cytokines, chemokines and other genes implicated in pain and inflammation pathways following treatment with a mixture of Free-B-ring flavonoids and flavans using semi-quantitative RT-qPCR techniques. This work has been coupled work with ELISA-based assays to evaluate changes in protein levels as well as enzyme function assays to evaluate alterations in protein function. As a result of these studies, both genomic and proteomic coupled effects following treatment with Univestin™ have been demonstrated. Other studies cited in the literature have used protein specific methods to infer gene expression rather than show it directly. The results are set forth in FIGS. 16 and 17.

Example 18

Evaluation of the Efficacy of Univestin™ with in vivo Mouse Ear Swelling Model

Figure 18:
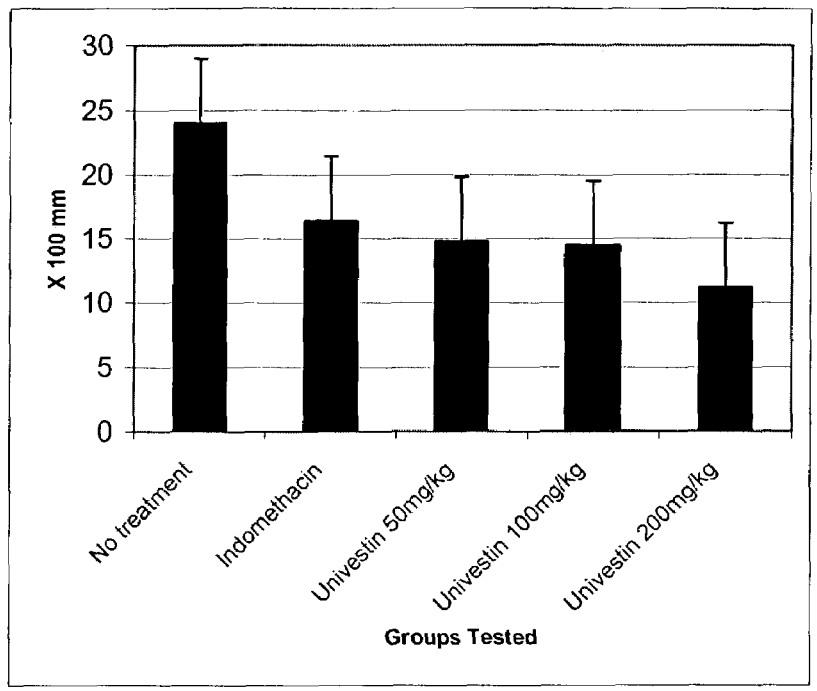
FIG. 18 illustrates graphically ear-swelling data as a measure of inhibition of inflammation. Univestin™ produced through the combination of standardized extracts of Free-B-ring flavonoids and flavans in a ratio of 80:20 was compared to untreated mice and mice given indomethacin (50 mg/kg) via oral gavage. The data is presented as the difference in micron measurement of the untreated vs. the treated ear lobe for each mouse.

In order to test whether Univestin™ could be used to treat inflammation in vivo, the composition, prepared as described in Example 14, was administered by oral gavage to 4-5 week old ICR mice (Harlan Labs) one day before treatment of their ears with AA. Test mice were fed dose equivalents of 50, 100 and 200 mg/kg of Univestin™ suspended in olive oil while control mice were fed only olive oil. The following day, 20 μL of 330 mM AA in 95% alcohol was applied to one ear of each mouse, while alcohol was applied to the other ear as a control. Mice treated with Univestin™ showed a measurable dose response that tracked with increasing doses of Univestin™, as demonstrated in FIG. 18. With reference to FIG. 18, the 200 mg/kg dose reduces swelling by over 50% as compared to the minus Univestin™ control. The 50 mg/kg dose of Univestin™ was as effective as the 50 mg/kg dose of another strong anti-inflammatory, indomethacin.

Example 19

Evaluation Efficacy of Univestin™ with in vivo Mouse Ankle Joint Swelling Model

Figure 19:
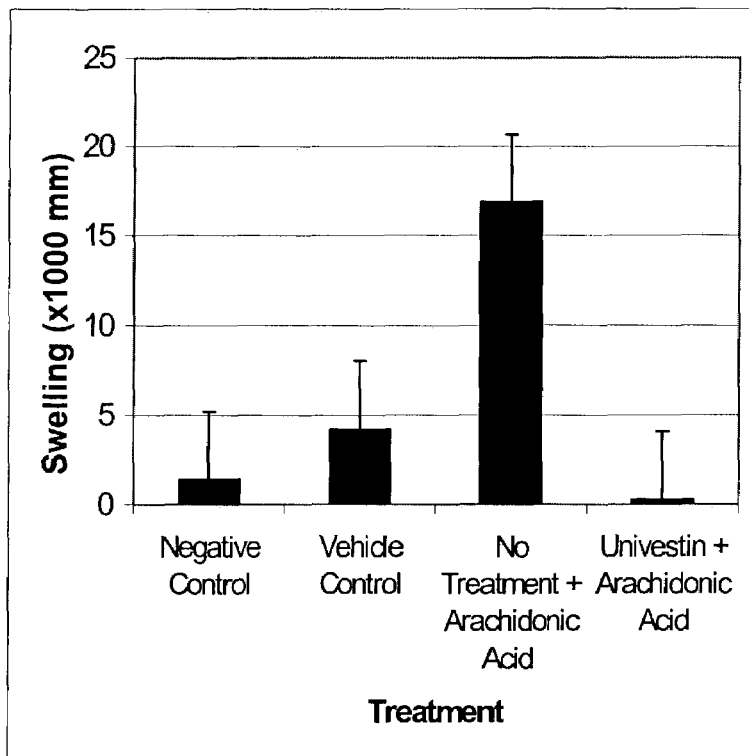
FIG. 19 shows the effect of 100 mg/kg of Univestin™ (80:20) ratio of standardized extracts of Free-B-ring flavonoids to flavans) on the AA injected ankles of mice (Univestin™+arachidonic acid) compared to non-treated mice (no treatment+arachidonic acid), mice without AA injections (negative control) or mice that were injected with the liquid carrier (vehicle control).
Figure 20:
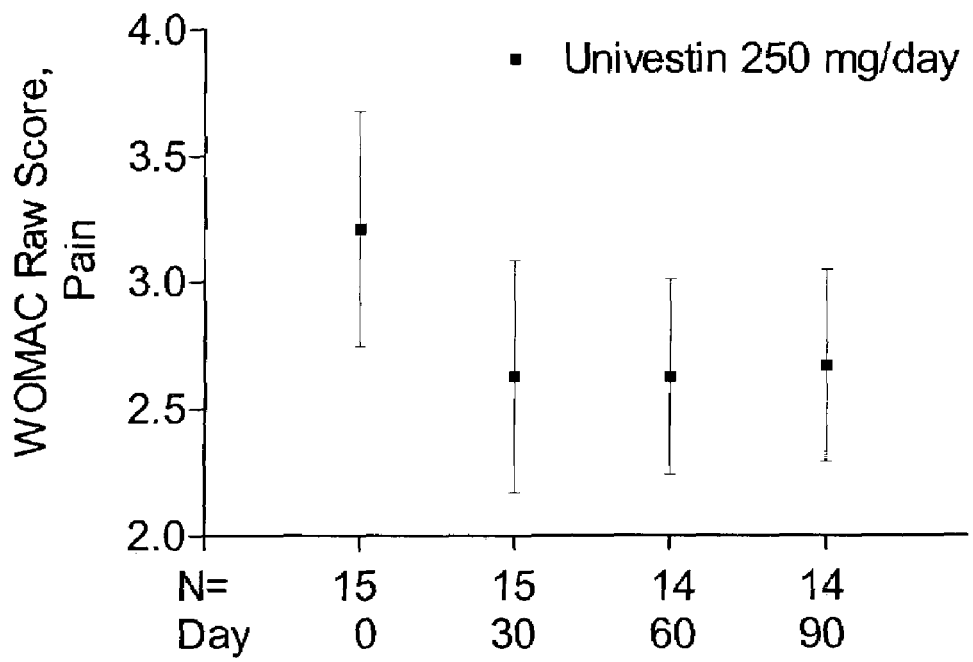
FIG. 20 illustrates graphically the 95% confidence interval for the pain index WOMAC score at baseline, 30, 60 and 90 days of treatment with Univestin™ at a dosage of 250 mg/day.
Figure 21:
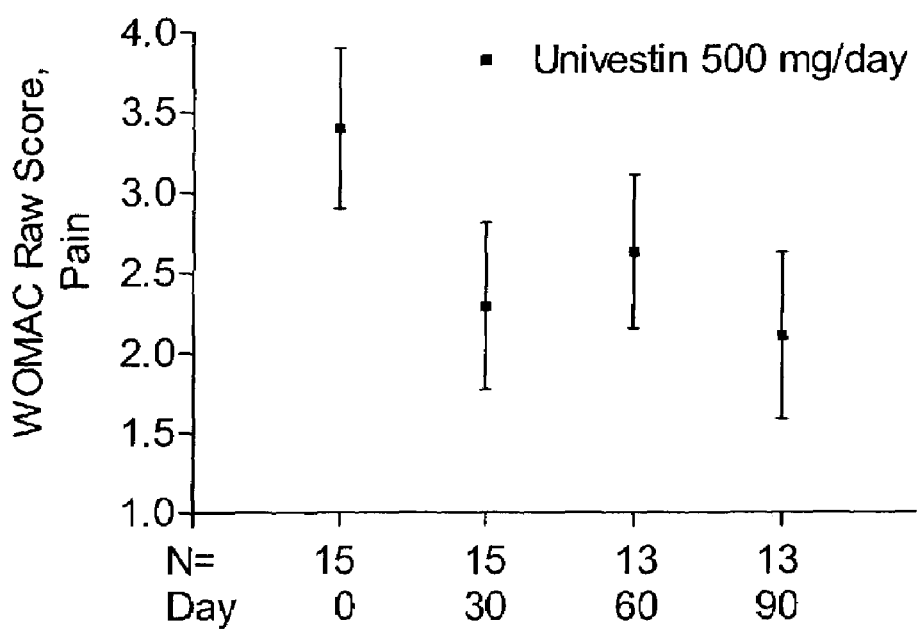
FIG. 21 illustrates graphically the 95% confidence interval for the pain index WOMAC score at baseline, 30, 60 and 90 days of treatment with Univestin™ at a dosage of 500 mg/day.
Figure 22:
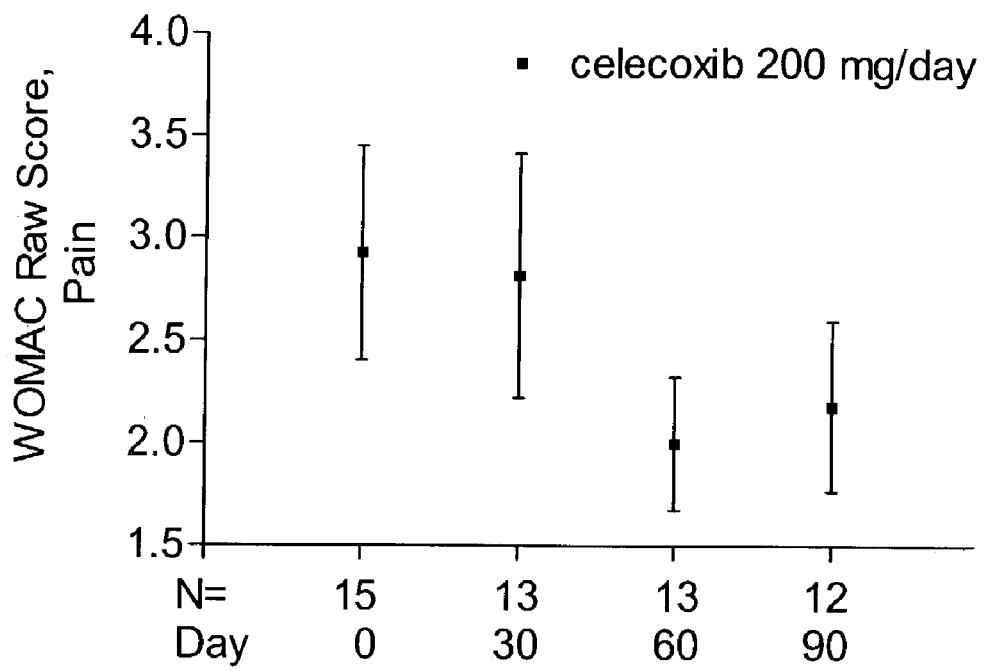
FIG. 22 illustrates graphically the 95% confidence interval for the pain index WOMAC score at baseline, 30, 60 and 90 days of treatment with celecoxib at a dosage of 200 mg/day.
Figure 23:
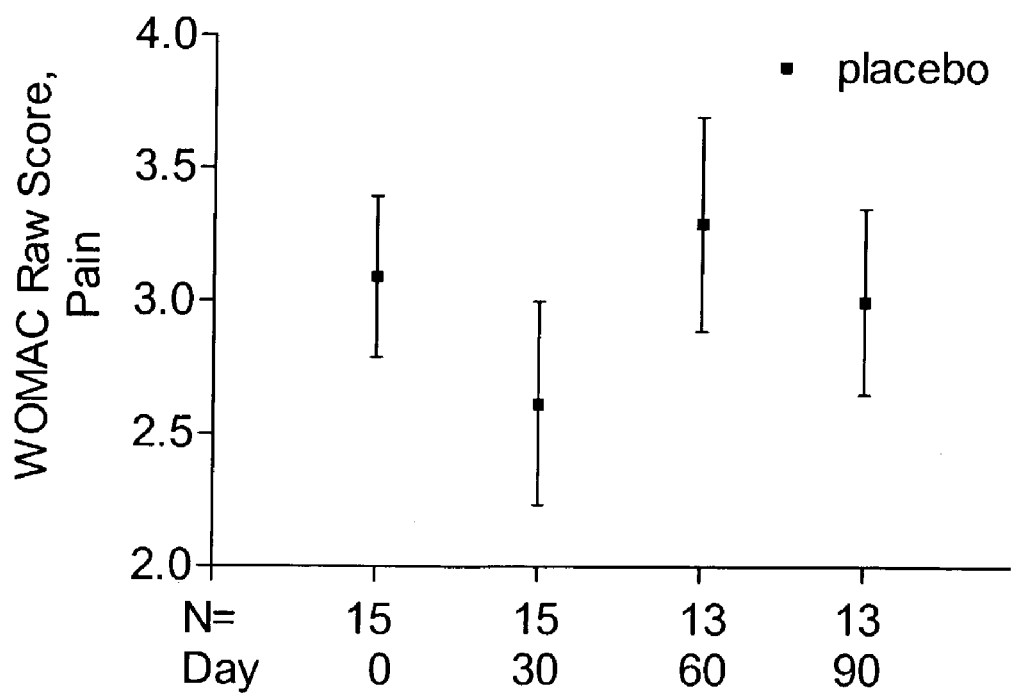
FIG. 23 illustrates graphically the 95% confidence interval for the pain index WOMAC score at baseline, 30, 60 and 90 days of treatment with the placebo.
Figure 24:
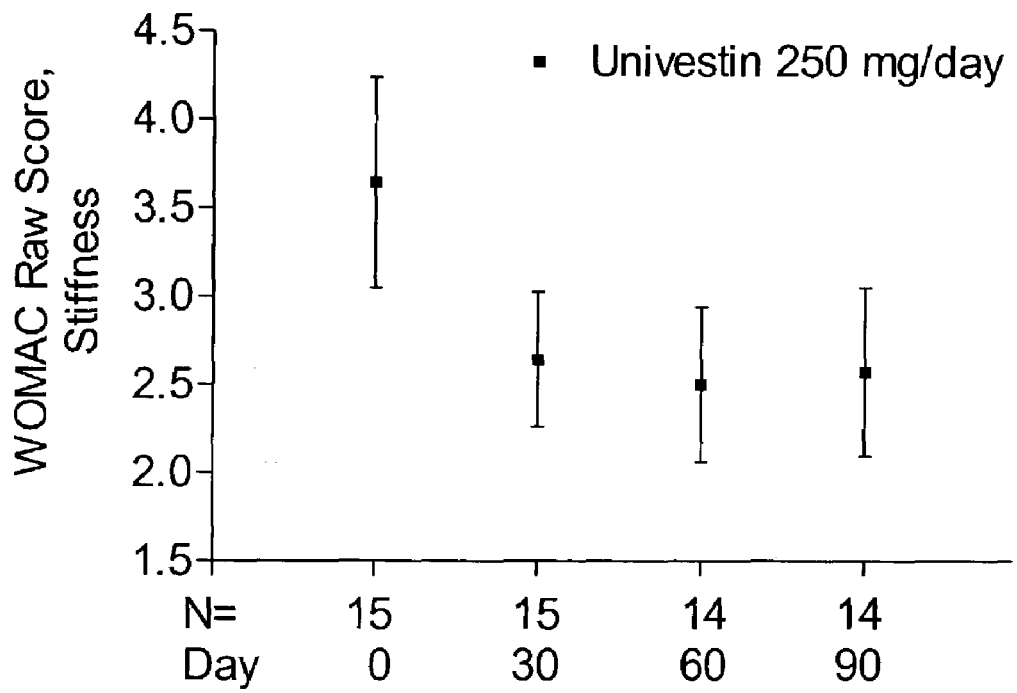
FIG. 24 illustrates graphically the 95% confidence interval for the stiffness index WOMAC score at baseline, 30, 60 and 90 days of treatment with Univestin™ at a dosage of 250 mg/day.
Figure 25:
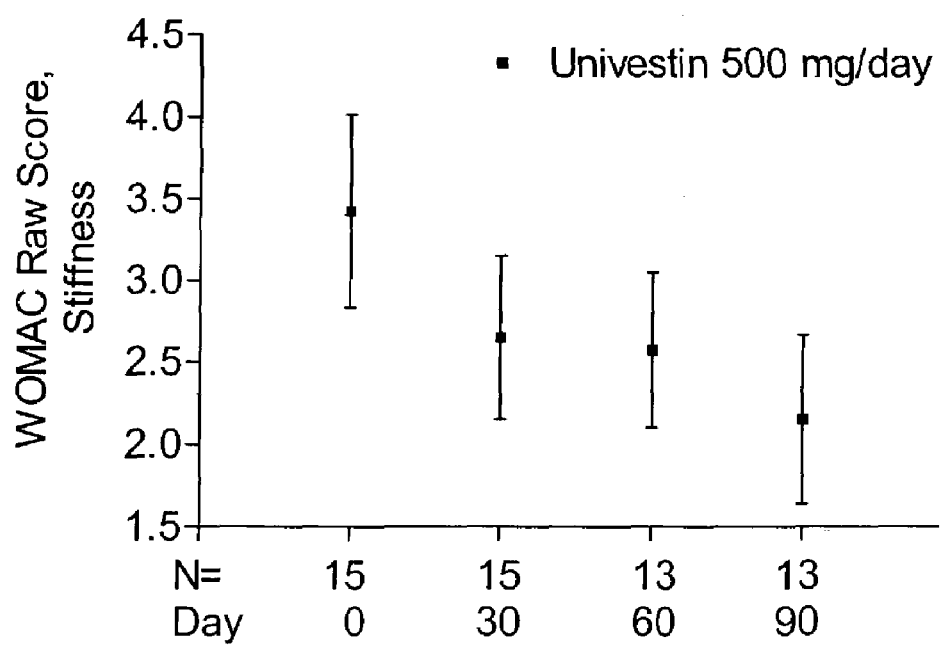
FIG. 25 illustrates graphically the 95% confidence interval for the stiffness index WOMAC score at baseline, 30, 60 and 90 days of treatment with Univestin™ at a dosage of 500 mg/day.
Figure 26:
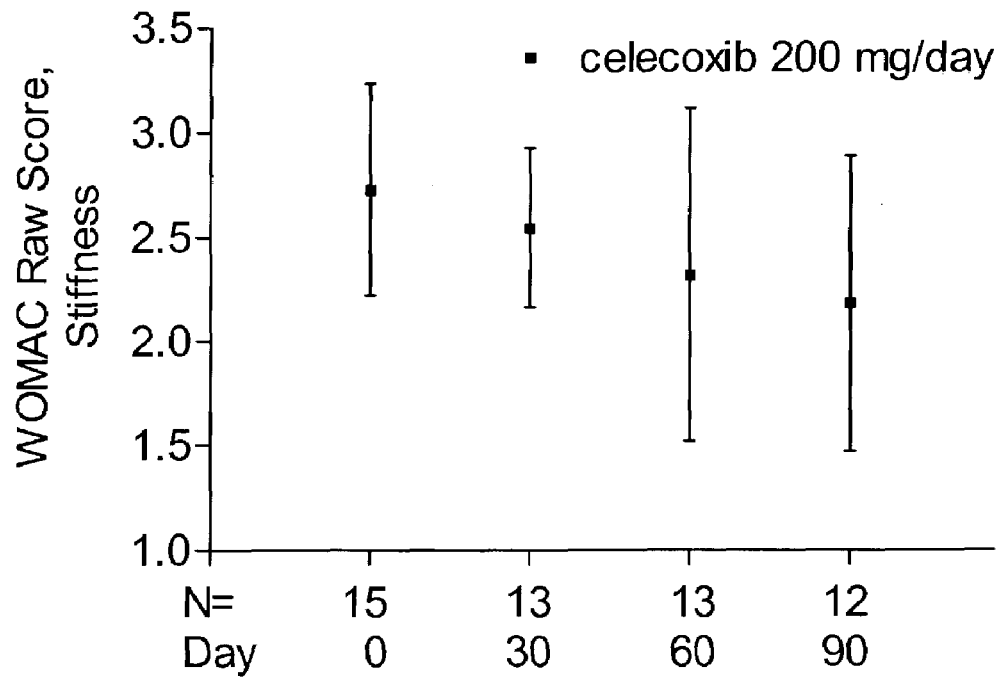
FIG. 26 illustrates graphically the 95% confidence interval for the stiffness index WOMAC score at baseline, 30, 60 and 90 days of treatment with celecoxib at a dosage of 200 mg/day.
Figure 27:
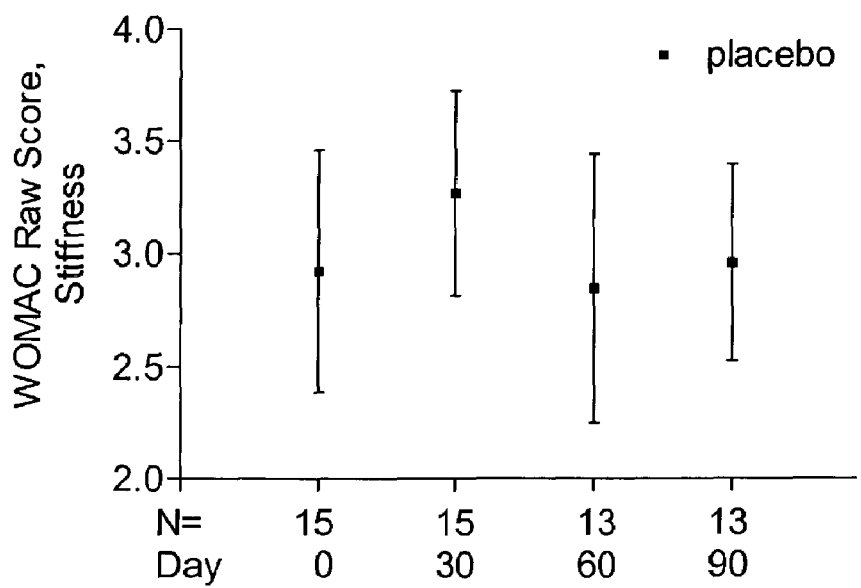
FIG. 27 illustrates graphically the 95% confidence interval for the stiffness index WOMAC score at baseline, 30, 60 and 90 days of treatment with the placebo.
Figure 28:
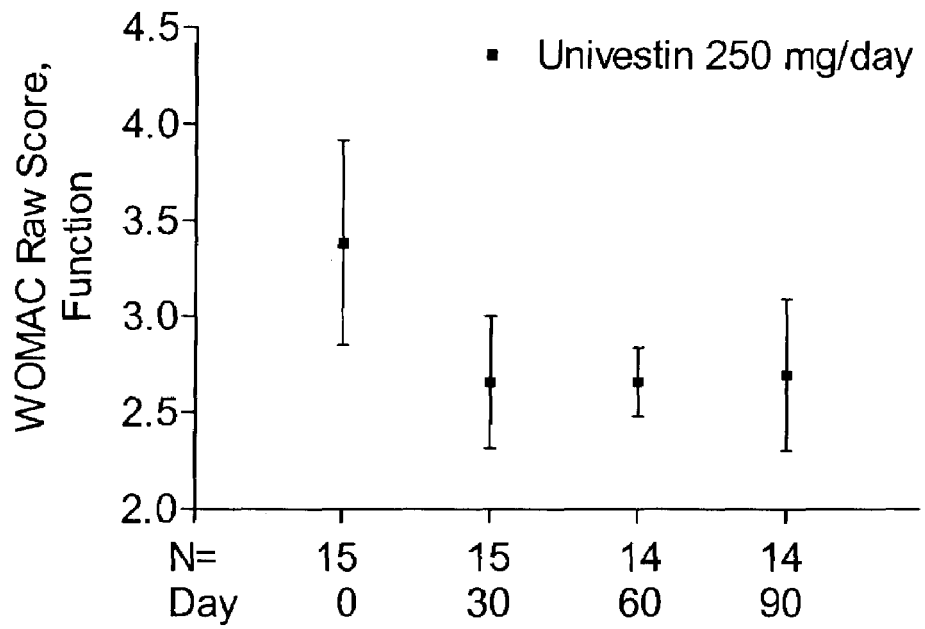
FIG. 28 illustrates graphically the 95% confidence interval for the functional impairment index WOMAC score at baseline, 30, 60 and 90 days of treatment with Univestin™ at a dosage of 250 mg/day.
Figure 29:
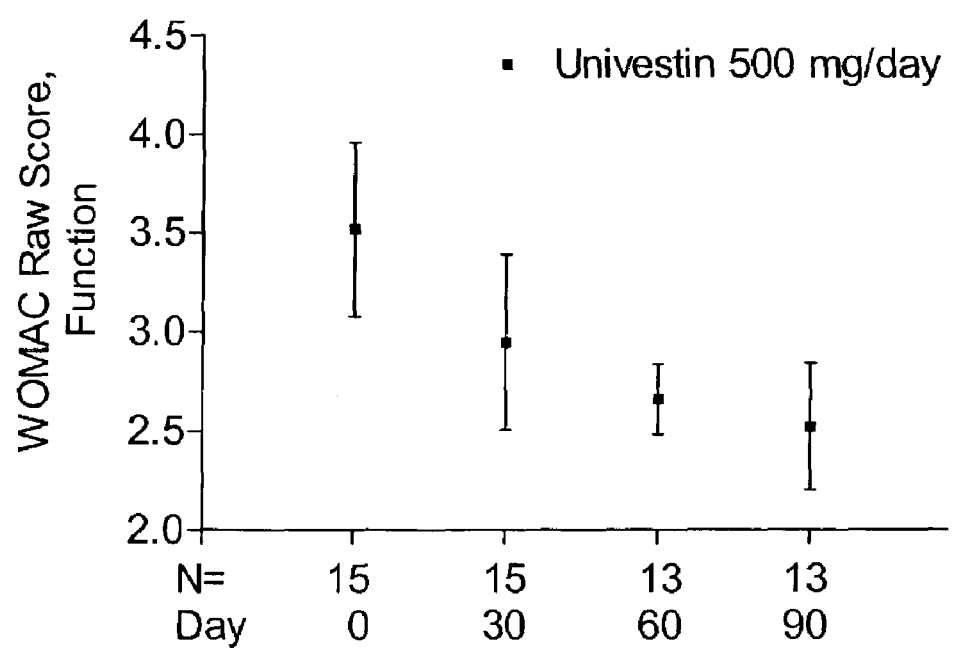
FIG. 29 illustrates graphically the 95% confidence interval for the functional impairment index WOMAC score at baseline, 30, 60 and 90 days of treatment with Univestin™ at a dosage of 500 mg/day.
Figure 30:
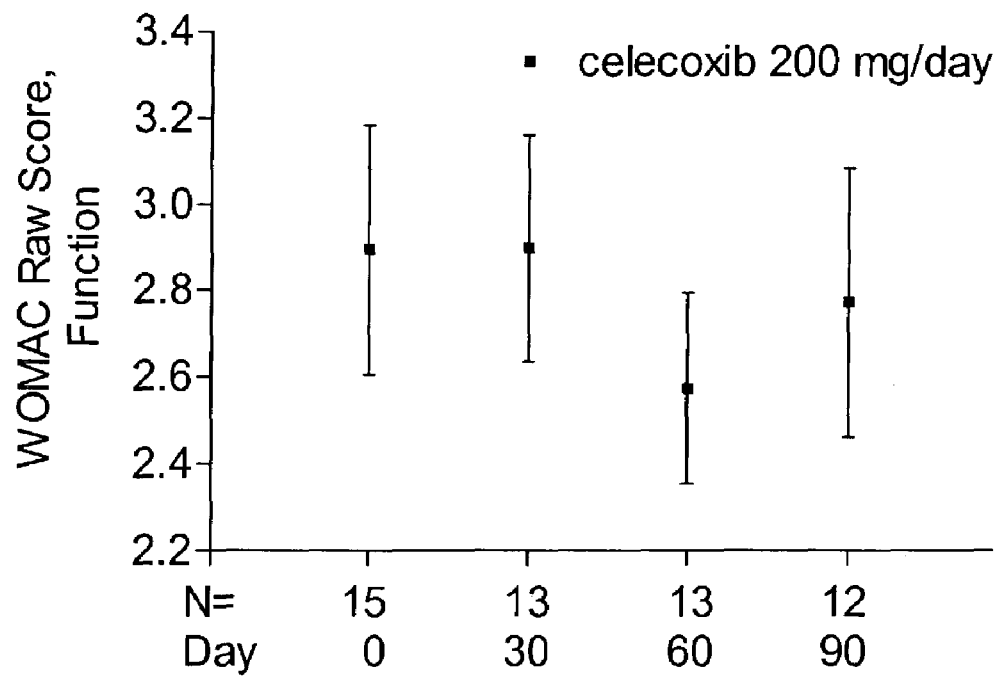
FIG. 30 illustrates graphically the 95% confidence interval for the functional impairment index WOMAC score at baseline, 30, 60 and 90 days of treatment with celecoxib at a dosage of 200 mg/day.
Figure 31:
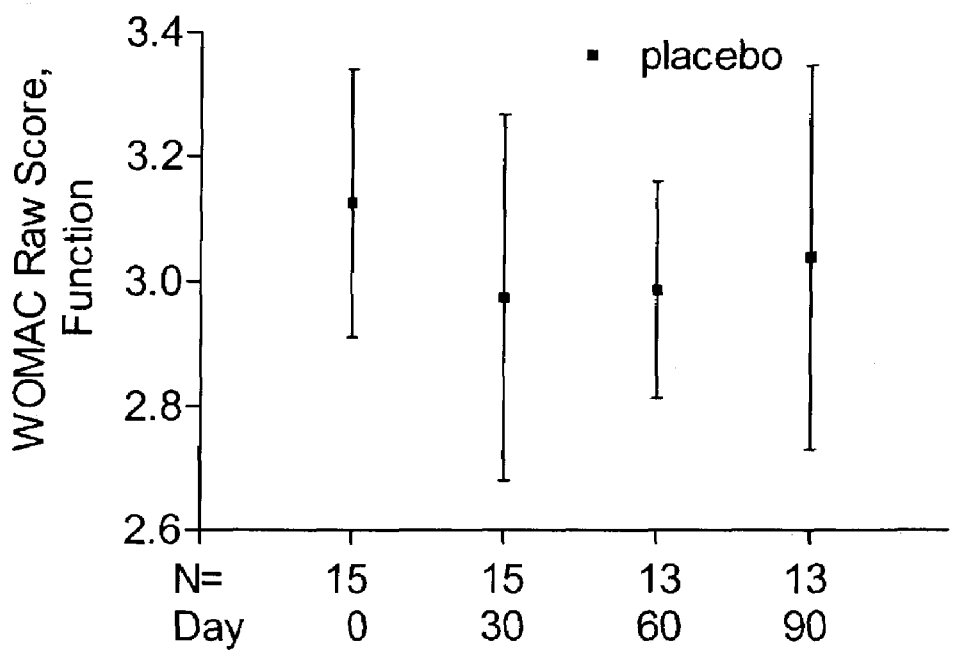
FIG. 31 illustrates graphically the 95% confidence interval for the functional impairment index WOMAC score at baseline, 30, 60 and 90 days of treatment with the placebo.

Since Univestin™ is designed to target joint pain, a solution of 20 μL of 100 mM AA in 95% ethanol was injected into the hind ankle joints of 4-5 week old ICR mice (Harlan Labs) to generate swelling. The test group was fed 100 mg/kg of Univestin™ suspended in olive oil ~12 hours before while another group was not given Univestin™. Control groups included mice that had not received arachidonic acid injections (negative control) and a group that had 95% ethanol without AA injected (vehicle control). These groups were also not given Univestin™. The results are set forth in FIG. 19. With reference to FIG. 19, the mice given Univestin™ that were injected with AA showed background levels of swelling as compared to the controls and the untreated arachidonic injected group. These results demonstrate the effectiveness of Univestin™ for reducing swelling in joints, the site of action.

Example 20

Clinical Evaluation of the Efficacy of Free-B-ring Flavonoids and Flavans on the Relief of Pain Caused by Rheumatoid Arthritis or Osteoarthritis of the Knee and/or Hip This clinical study was a single-center, randomized, double-blind, placebo-controlled study. Sixty subjects (n=60) with rheumatoid arthritis or osteoarthritis of the knee and/or hip were randomly placed into one of the following four groups:

| | | | |
|---|---|---|---|
| $A_0$ Placebo | n = 15 | Placebo | |
| $A_1$ Dose 1 | n = 15 | Univestin ™ | 250 mg/day (125 mg b.i.d.) |
| $A_2$ Dose 2 | n = 15 | Univestin ™ | 500 mg/day (250 mg b.i.d.) |
| $A_3$ Active Control | n = 15 | Celecoxib | 200 mg/day (100 mg b.i.d.) |

The Univestin™ was prepared as described in Example 14. This specific batch of Univestin™ (lot#G1702-COX-2) contains 86% total active ingredients, including 75.7% Free-B-ring flavonoids and 10.3% flavans. Celecoxib, also known as Celebrex™, is a trade name for a prescription drug that is a COX-2 selective inhibitor.

Subjects were sex-matched and recruited from ages 40 to 75. Treatment consisted of oral administration for 90 days of the placebo or active compound (Univestin™ or celecoxib) according to the above dose schedule. Subjects taking NSAIDs engaged in a two-week washout period before beginning the study. Physical activity was not restricted, nor were the subjects given any advice as to diet. Subjects were free to withdraw from the trial at any time for any reason. The efficacy of the treatments was evaluated at 30, 60 and 90 days of oral administration by physicians, using the Western Ontario and McMaster Universities (WOMAC) Osteo-Arthritis Index (See Lingard et al. (2001) J. Bone & Joint Surg. 83:1856-1864; Soderman and Malchau (2000) Acta Orthop. Scand. 71(1):39-46). This protocol was reviewed and approved by an IRB board from University of Montreal.

The WOMAC was administered to subjects preferably in the doctor's office. They were asked to read and respond to a questionnaire on their own or via proxy in the waiting room of the doctor's office or were interviewed by project personnel over the telephone and the data were transcribed in the computer database. This offered a stable environment among patients and reduced the possibility of bias due to different home environments among patients. Between groups differences for all measurements were evaluated with One-Way Analysis of Variance and Tukey's Least Significant Difference for multiple comparisons. All questions were assigned a weight from 0 to 4 depending on the severity of pain, stiffness or impaired function. These values were then converted to percentages normalized to 100 and reported as WOMAC scores. Higher values are indicative of greater impairment. Table 12 sets forth the mean WOMAC index scores for pain, stiffness and function for 250 mg and 500 mg per day Univestin™ compared to celecoxib at 200 mg per day and the placebo before treatment (baseline) and at 30, 60 and 90 days after treatment. The lower the score, the less pain and stiffness and better function a patient has.

TABLE 12

WOMAC Index Scores at Baseline and at 30, 60 and 90 Days

| WOMAC INDICE | Univestin™ 250 | | Univestin™ 500 | | Celecoxib 200 | | Placebo | |
|---|---|---|---|---|---|---|---|---|
| | Mean | Std Dev | Mean | Std Dev | Mean | Std Dev | Mean | Std Dev |
| Pain-basline | 54.33 | 19.9 | 60.33 | 23.34 | 55 | 22.28 | 49.33 | 15.1 |
| Pain-30 days | 41.33 | 19.22 | 36 | 22.93 | 50 | 23.09 | 41.67 | 15.55 |
| Pain-60 days | 40.71 | 16.62 | 40.77 | 19.77 | 30 | 16.46 | 57.31 | 16.66 |
| Pain-90 days | 41.79 | 16.36 | 27.69 | 21.57 | 31.67 | 16.42 | 50 | 14.43 |
| Stiffness-baseline | 63.33 | 26.92 | 61.67 | 23.84 | 47.5 | 21.75 | 46.67 | 21.37 |
| Stiffness-30 days | 41.67 | 16.14 | 44.17 | 21.06 | 39.42 | 18.29 | 59.17 | 20.85 |
| Stiffness-60 days | 37.5 | 18.99 | 39.42 | 19.66 | 37.5 | 29.76 | 46.15 | 24.68 |
| Stiffness-90 days | 39.29 | 20.72 | 28.85 | 21.28 | 29.17 | 25.19 | 49.04 | 18.01 |
| Function-baseline | 58.41 | 22.74 | 62.92 | 17.68 | 49.38 | 10.33 | 52.82 | 8.29 |
| Function-30 days | 42.09 | 14.51 | 47.59 | 17.18 | 48.43 | 9.29 | 51.88 | 14.8 |
| Function-60 days | 41.47 | 7.75 | 41.59 | 7.34 | 41.23 | 9.12 | 49.64 | 7.16 |
| Function-90 days | 42.44 | 17.08 | 38.12 | 13.21 | 44.41 | 11.06 | 50.95 | 12.73 |

Table 13 sets forth the mean absolute change in WOMAC scores for pain, stiffness and function. They are expressed as the difference between the baseline and the scores given at 30, 60 and 90 days. The more negative the score, the greater the improvement.

TABLE 13

Mean Absolute Change in WOMAC Scores at 30, 60 and 90 Days*

| Absolute Change | Univestin™ 250 | | Univestin™ 500 | | Celecoxib 200 | | Placebo | |
|---|---|---|---|---|---|---|---|---|
| | Mean | Std Dev | Mean | Std Dev | Mean | Std Dev | Mean | Std Dev |
| Pain-30 days | −13 | 24.41 | −24.33 | 18.7 | −4.23 | 15.92 | −7.76 | 26.98 |
| Pain-60 days | −14.64 | 26.85 | −17.31 | 35.27 | −22.31 | 22.51 | 5 | 13.54 |
| Pain-90 days | −13.57 | 22.91 | −30.38 | 21.06 | −16.67 | 21.36 | −2.31 | 15.89 |
| Stiffness-30 days | −21.67 | 24.31 | −17.5 | 18.18 | −8.65 | 20.66 | 12.5 | 29.88 |
| Stiffness-60 days | −28.57 | 27.05 | −21.15 | 33.61 | −9.62 | 29.82 | −1.92 | 30.55 |
| Stiffness-90 days | −26.79 | 27.67 | −31.73 | 20.17 | −13.54 | 37.48 | −0.96 | 26.74 |
| Function-30 days | −16.32 | 19.58 | −15.33 | 18.28 | −0.37 | 6.86 | −0.94 | 14.05 |
| Function-60 days | −18.11 | 24.36 | −21.4 | 19.79 | −6.97 | 13.66 | −3.49 | 11.81 |
| Function-90 days | −17.13 | 23.69 | −24.87 | 23.25 | −2.78 | 8.34 | −2.18 | 11.27 |

*These data contain only subjects who completed the study.

It is very difficult to ascribe a standard deviation to a group mean in a clinic trial due to the severe differences that appear in the data. Rather, confidence limits for the mean are preferred because they give a lower and upper limit for the mean and the narrower the interval, the more precise the estimate of the mean. Confidence limits are expressed in terms of a confidence coefficient. A 95% confidence interval is the most commonly used interval to describe a mean in this type of statistical analysis. This does not imply that there is a 95% probability that the interval contains the true mean. Instead, the level of confidence is associated with the method of calculating the interval. The confidence coefficient is simply the proportion of samples of a given size that may be expected to contain the true mean. That is, for a 95% confidence interval, if many samples are collected and the confidence interval computed, in the long run about 95% of these intervals would contain the true mean. With this in mind, the 95% confidence interval was computed for the WOMAC scores for pain, stiffness and function at 30, 60 and 90 days.

Raw/non standardized scores for the WOMAC scores based on a five point Likert scale with a range between 1 and 5 were chosen to represent the final pain, stiffness and impaired function indices (FIGS. 20-31). Standardization to a scale between 0 and 100 was used in other sections for uniformity (see Tables 12 and 13) and to enhance the appreciation of the magnitudes of changes. However, given that all the figures are based on the same 1-5 point scales the raw data were plotted since they more accurately reflect the methods by which these scores were obtained from the patient questionnaires. In other words, since the patients were given a choice between 1 and 5 these representations better reflect the patient's response as opposed to the standardized or transformed score of 0-100 that does not reflect the patient's perception of possible range of answers.

Clear trends exist showing that for the pain indice that Univestin™ at 250 and 500 mg/day reduced pain over the 90 day treatment period based on the patient responses. Celecoxib also reduces pain over this same period of time compared to the placebo, which does not. However, celecoxib does not seem to be as effective as Univestin™ at both dosages in reducing stiffness, since the confidence intervals heavily overlapped those of the placebo. Finally, Univestin™ at both doses clearly improved functional impairment, but celecoxib does not compared to placebo. The graphic representations contain all subjects even if they did not complete the study. Each confidence interval, however, is valid based on the number of subjects that were present at the time the WOMAC tests were taken so the trends still hold. These data are plotted in FIGS. 20 through 31.

Example 21

Clinical Evaluation of the Efficacy of Free-B-ring Flavonoids and Flavans on BMI and Weight Loss Due to an Increase in Function.

Additional measurements taken during the clinical trial were height and weight. All subjects in all groups (see Example 20) were measured for height and weight at 30 and 90 days of treatment. The subjects were given no recommendations on diet or exercise in order not to bias the results toward reduction of BMI and weight loss. Table 14 illustrates the changes in weight and BMI that occurred after treatment for 30 and 90 days.

TABLE 14

Change in Mean Weight (kg) and BMI (kg/m$^2$) at 30 and 90 Days

| | Group | | | | | | | |
|---|---|---|---|---|---|---|---|---|
| | Univestin ™ 250 | | Univestin ™ 500 | | Celecoxib 200 | | Placebo | |
| | Mean | Std Dev | Mean | Std Dev | Mean | Std Dev | Mean | Std Dev |
| Weight-30 days | −3.60 | 3.76 | −2.40 | 3.31 | −2.00 | 3.08 | −.60 | 1.99 |
| Weight-90 days | −5.36 | 3.43 | −4.15 | 4.81 | −3.17 | 4.88 | −.08 | 1.50 |
| BMI-30 days | −1.28 | 1.33 | −.80 | 1.13 | −.68 | 1.06 | −.20 | .64 |
| BMI-90 days | −1.84 | 1.14 | −1.39 | 1.64 | −1.07 | 1.67 | −.02 | .54 |

Based on these data, the 250 mg/day dose of Univestin™ gave the greatest amount of weight loss and change in BMI followed by the 500 mg/day dose of Univestin™ and then celecoxib. The placebo had no effect on weight or BMI.

It is not believed that there are any other reports in the literature of anti-inflammatory compounds being used to effect weight loss or changes in BMI. Though the subjects were given no advice on exercise, the greater functional capabilities gained after treatment, especially with Univestin™, may have allowed them to exercise more on their own accord. Alternatively, Univestin™ may be increasing thermogenesis, lipolysis, or causing an under utilization of carbohydrates or fat in the diet. FIGS. 32 and 33 illustrate the BMI and weight loss seen for Univestin™ after 30 and 90 days of treatment.

Example 22

Clinical Evaluation of the Efficacy of Free-B-ring Flavonoids and Flavans on Lowering of Blood Glucose Due to an Increase in Function.

Blood glucose was also taken at 0 (baseline), 30 days and 90 days after treatment (see Example 20). These measurements were reported in mmole per liter. The data is also shown in mg/dL. Table 15 sets forth blood glucose levels after 30 and 90 days of treatment with Univestin™ at 250 and 500 mg/day.

TABLE 15

Change in Blood Glucose after 30 and 90 days of Treatment

| | Group | | | | | | | | |
|---|---|---|---|---|---|---|---|---|---|
| | Univestin ™ 250 | | | Univestin ™ 500 | | | Placebo | | |
| | mmol/L | mg/dL | Std Dev | mmol/L | mg/dL | Std Dev | mmol/L | mg/dL | Std Dev |
| Glucose-Baseline | 5.24 | 94.32 | .74 | 5.09 | 91.62 | .67 | 4.82 | 86.76 | .80 |
| Glucose-30 days | 5.10 | 91.80 | .71 | 4.75 | 85.50 | .55 | 5.08 | 91.44 | .54 |
| Glucose-90 days | 4.88 | 87.84 | .72 | 4034 | 78.12 | .36 | 4.71 | 84.78 | .56 |
| Percent Change By 90 days | | −7.52 | | | −12.79 | | | .94 | |

These data suggest that both the 250 and the 500 mg/day doses of Univestin™ are significantly lowering blood glucose levels over time. This impact may or may not be related to the loss of weight observed above or to the presumed increase in activity as functional impairment improved. It may also be possible that Univestin™ is acting directly to improve glucose metabolism by decreasing glucose tolerance or by utilizing carbohydrates more effectively.

The invention claimed is:

1. A method for decreasing body mass index and causing weight loss said method comprising administering to a host in need thereof an effective amount of a composition consisting essentially of baicalin and catechin, wherein said composition is administered in a dosage selected from 0.01 to 200 mg/kg of body weight.

2. The method of claim 1 wherein the routes of the administration are selected from the group consisting of oral, topical, suppository, intravenous, and intradermic, intragaster, intramusclar, intraperitoneal and intravenous administration.

* * * * *